United States Patent
Napoletano et al.

(10) Patent No.: US 9,216,975 B2
(45) Date of Patent: Dec. 22, 2015

(54) TRPV1 VANILLOID RECEPTOR ANTAGONISTS WITH A BICYCLIC PORTION

(75) Inventors: Mauro Napoletano, Milan (IT); Marcello Trevisani, Gavello di Bondeno (IT); Maria Giovanna Pavani, Vigarano Mainarda (IT); Francesca Fruttarolo, Ferrara (IT)

(73) Assignee: Serentrix, LLC., Exton, PA (US)

(*) Notice: Subject to any disclaimer, the term of this patent is extended or adjusted under 35 U.S.C. 154(b) by 137 days.

(21) Appl. No.: 13/636,898

(22) PCT Filed: Dec. 22, 2010

(86) PCT No.: PCT/EP2010/070538
§ 371 (c)(1),
(2), (4) Date: Nov. 29, 2012

(87) PCT Pub. No.: WO2011/120604
PCT Pub. Date: Oct. 6, 2011

(65) Prior Publication Data
US 2013/0079339 A1    Mar. 28, 2013

(30) Foreign Application Priority Data
Mar. 30, 2010    (EP) .................................... 10158292

(51) Int. Cl.
*C07D 405/12*    (2006.01)
*C07D 401/14*    (2006.01)
(Continued)

(52) U.S. Cl.
CPC ............ *C07D 413/14* (2013.01); *C07D 209/34* (2013.01); *C07D 235/26* (2013.01);
(Continued)

(58) Field of Classification Search
CPC .. C07D 405/12; C07D 401/14; C07D 413/12; C07D 413/14; C07D 401/12; C07D 403/12
USPC ........................................ 544/105; 514/230.5
See application file for complete search history.

(56) References Cited

U.S. PATENT DOCUMENTS

| | | | |
|---|---|---|---|
| 7,691,851 B2 * | 4/2010 | Gege et al. ................. | 514/230.2 |
| 2003/0078252 A1 | 4/2003 | Sanner et al. | |

FOREIGN PATENT DOCUMENTS

| | | |
|---|---|---|
| EP | 1 632 477 A1 | 3/2006 |
| WO | 00/76501 A1 | 12/2000 |

(Continued)

OTHER PUBLICATIONS

Shridhar et al. Organic Preparations and Procedures International (1984), 16(2), 91-6.*

(Continued)

*Primary Examiner* — Kahsay Habte

(74) *Attorney, Agent, or Firm* — Blank Rome LLP

(57) ABSTRACT

The invention discloses compounds of formula I wherein Y is a group of formula A, B, C, D, or E:

and W, Q, n, R1, R2, R3, U1-U5, J and K have the meanings given in the description.

The compounds of formula I are TRPV1 antagonists and are useful as active ingredients of pharmaceutical compositions for the treatment of pain and other conditions ameliorated by the inhibition of the vanilloid receptor TRPV1.

7 Claims, No Drawings

(51) Int. Cl.
*C07D 413/12* (2006.01)
*C07D 413/14* (2006.01)
*C07D 401/12* (2006.01)
*C07D 403/12* (2006.01)
*C07D 209/34* (2006.01)
*C07D 235/26* (2006.01)
*C07D 263/58* (2006.01)
*C07D 265/36* (2006.01)

(52) U.S. Cl.
CPC ............ *C07D263/58* (2013.01); *C07D 265/36* (2013.01); *C07D 401/12* (2013.01); *C07D 401/14* (2013.01); *C07D 403/12* (2013.01); *C07D 405/12* (2013.01); *C07D 413/12* (2013.01)

(56) References Cited

FOREIGN PATENT DOCUMENTS

WO    2005/028445 A2    3/2005
WO    2010/108187 A2    9/2010

OTHER PUBLICATIONS

Kolasa, et al., "Preliminary pharmacological studies of the central action of phenyl and piperidinomethyl derivatives of 2-benzoxazolone," 6001 Chemical Abstracts, vol. 99, No. 1, p. 16, Apr. 7, 1983 (XP-002145766).

* cited by examiner

TRPV1 VANILLOID RECEPTOR ANTAGONISTS WITH A BICYCLIC PORTION

This application is a U.S. national stage of PCT/EP2010/070538 filed on Dec. 22, 2010, which claims priority to and the benefit of European Application No. 10158292.2, filed on Mar. 30, 2010, the contents of which are incorporated herein by reference.

FIELD OF THE INVENTION

The present invention concerns TRPV1 antagonists characterized by a bicyclic portion and, when possible, pharmaceutically acceptable salts thereof along with the formulations containing them. The pharmaceutical compositions of the invention are useful in the treatment of pain and other conditions ameliorated by the inhibition of the vanilloid receptor TRPV1.

BACKGROUND

The transient receptor potential vanilloid 1 (TRPV1) is a member of ion channels mainly localized on primary afferent neurons. Activation of TRPV1 on sensory neurons by chemical stimulants including capsaicin and resiniferatoxin, as well as low pH (<6), heat (>42° C.), and nucleosides such as ATP, leads to an influx of $Ca^{2+}$ and $Na^+$ ions through the channel, causing depolarization of the cell and transmission of painful stimuli. Unlike traditional analgesic drugs that either suppress inflammation (e.g. NSAIDs and COX-2 inhibitors) or block pain transmission (e.g. opiates), TRPV1 channel inhibitors aim to prevent pain by blocking a receptor where pain is generated. In patients, the expression of TRPV1 is up-regulated in a number of painful inflammatory disorders. TRPV1 as a pain target has been validated by genetic deletion and pharmacological inhibition experiments. The pungency of capsaicin and many other agonists at the vanilloid receptor clearly defines TRPV1 as a key transducer in the pain pathway. Characterization of TRPV1 mice, which lack both copies of the TRPV1 gene, shows a complete absence of thermal hyperalgesia associated with inflammation demonstrating the key role of TRPV1 in disease and providing impetus to develop selective TRPV1 antagonists as a novel pain therapy with the potential for an improved side effect profile compared to existing therapies. Many novel selective and chemically distinct TRPV1 antagonists have been identified and a number of these have been assessed in preclinical models of pain. Some of them reverse mechanical hyperalgesia in the Freund's complete adjuvant model of inflammatory pain in rodents. Others show efficacy in neuropathic pain models, in post-operative pain and in cancer pain. These data provide robust validation of this approach for the treatment of a broad range of pain conditions in humans.

In the bladder, the presence of TRPV1 was demonstrated in various cell types, including urothelium, detrusor muscle and fibroblasts. There is good evidence that TRPV1 in urothelium is functional. Capsaicin evokes an inward current similar to that seen in DRG neurons in patch-clamped human urothelial cells. Furthermore capsaicin induces calcium uptake in human urothelial cells culture which is blocked by the TRPV1 antagonists implying that the regulation of TRPV1 is similar in sensory neurons and urothelial cells. Overactive bladder (OAB) is a syndrome characterised by urgency (with or without urge incontinence), usually with frequency and nocturia, in the absence of other pathologic or metabolic conditions that might explain the symptoms. Differently from antimuscarinic compounds dominating the market of OAB that only act on the efferent components, TRPV1 antagonists, acting on sensory nerves or on urothelium, are effective in diverse experimental models of cystitis/overactive bladder without interfere with the physiological volume-induced avoiding contractions (VIVC) and distention of the urinary bladder in healthy animals.

The documented ability of citric acid as well as pungent compounds such as capsaicin to induce cough when delivered to the lungs of experimental animals and humans, combined with the contribution of TRPV1-sensitive nerves to airway hyper responsiveness and bronco constriction has led to a large degree of interest in the potential for targeting TRPV1 for the treatment of a range of respiratory diseases. These effects are thought to derive from the key contribution of TRPV1 which is highly expressed by sensory neurons and vagal afferents that innervate the airways, to the cough reflex. Preclinical studies have now demonstrated antitussive efficacy of a range of TRPV1 antagonists in rodent models.

Dry Eye is a chronic dysfunction on tear and ocular surface epithelium.

Changes in corneal osmolarity is a trigger key event in cytokine production and ocular inflammation which are main causes of Dry Eye.

There are evidences that TRPV1 signal induces pro-inflammatory cytokine secretion in the corneal epithelial cells and hyper osmolarity-induced cytokine production is prevented by TRPV1 antagonists in corneal epithelial cells.

These data provide a strong rational for the systemic and topical use of TRPV1 antagonists in the treatment of Dry Eye.

DESCRIPTION OF THE INVENTION

The present invention relates to TRPV1 inhibitors of formula (I)

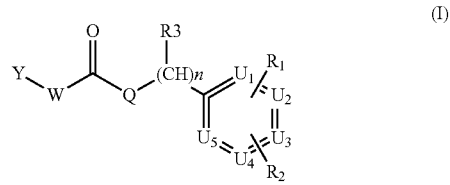

(I)

wherein:

Y is a group of formula A, B, C, D, or E:

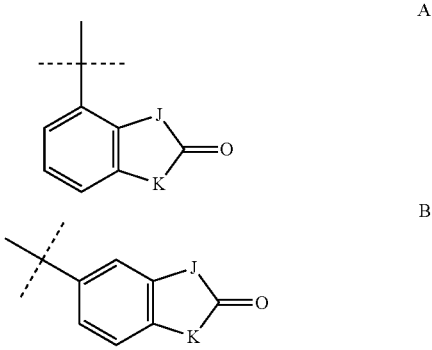

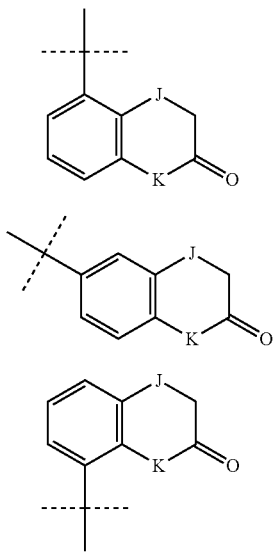

in which:
J and K are independently NH or O;
W is NH, O, a bond or $CH_2$;
Q is NH, O, a bond or $CH_2$;
n is 0 or 1;
U1, U2, U3, U4 and U5 form an aromatic ring and are independently CH, N, O, S, or one of them may be absent.

The aromatic ring is optionally substituted with one or both R1 and R2 groups.

When one of U1-U5 is absent, the general formula I also includes mono or bi-substituted five membered heterocyclic rings (e.g. furan, imidazole, thiazole, triazole, oxazole, isoxazole, thiophene, pyrazole).

R1 and R2 are independently selected from hydrogen, halogen, trifluoromethyl, ($C_1$-$C_4$)alkyl, ($C_1$-$C_4$)alkoxy, mono- or bis-($C_1$-$C_4$)alkylamino, monocyclic ring system containing 0-4 heteroatoms independently selected from N and O, which can be optionally substituted by OH, phenyl, heterocycle, and wherein the alkyl chains of said ($C_1$-$C_4$) alkyl, ($C_1$-$C_4$)alkoxy, mono- or bis($C_1$-$C_4$)alkylamino, can be optionally substituted with an amino, mono- or bis-($C_1$-$C_4$) alkylamino, morpholino, piperidino, pyrrolidino or piperazino group, provided that there are at least two carbon atoms between the nitrogen atom of said group and the oxygen atom of the ($C_1$-$C_4$)alkoxy or the nitrogen atom of said mono- or bis-($C_1$-$C_4$)alkylamino.

R3 is hydrogen or with n=1 is $CH_2$ and forms a cycle with R1=$CH_2$ or =$CH_2$—$CH_2$.

With the proviso that when n is 0, Q is NH and W is a bond, then Y is different from A or E, and with the exclusion of the compounds 3-oxo-3,4-dihydro-2H-benzo[1,4]oxazin-6-yl)-carbamic acid benzyl ester and benzyl (7-oxo)-5,6,7,8-tetrahydronaphthalen-1-yl)carbamate.

The disclaimed compounds are known from Biorganic & Medicinal Chemistry letters, 17, (2007), 1302-1306, WO2008/126024 and WO2005/040100.

When one asymmetrical carbon is present in a compound of the formula (I), such a compound may exist in optically active form or in the form of mixtures of optical isomers, e.g. in the form of racemic mixtures. The present invention refers to all optical isomers and their mixtures, including the racemic mixtures.

According to a first preferred embodiment, the invention relates to compounds of formula (IA), (IB) or (IC) wherein Y is A, C or E and W and Q are NH

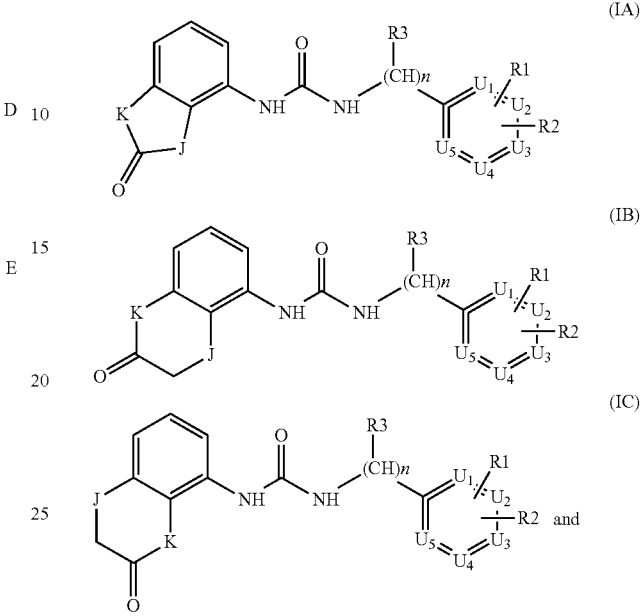

J and K are independently NH or O;
n is 0 or 1;
U1, U2, U3, U4 and U5 form an aromatic ring and are independently CH, N, O, S, or one of them may be absent.

When one of U1-U5 is absent, the general formula IA also includes mono or bi-substituted five membered heterocycle rings (e.g. furan, imidazole, thiazole, triazole, oxazole, isoxazole, pyrazole).

R1 is as defined above, more preferably hydrogen, halogen, trifluoromethyl, ($C_1$-$C_4$)alkyl, ($C_1$-$C_4$)alkoxy, mono- or bis-($C_1$-$C_4$)alkylamino, heterocycle, monocyclic ring system containing 0-4 heteroatoms independently selected from N and O, in particular pyrrolidin-1-yl, piperidin-1-yl, morpholin-4-yl, and wherein the alkyl chains of said ($C_1$-$C_4$)alkyl, ($C_1$-$C_4$)alkoxy, mono- or bis($C_1$-$C_4$)alkylamino, can be optionally substituted with an amino, mono- or bis-($C_1$-$C_4$) alkylamino, morpholino, piperidino, pyrrolidino or piperazino group, provided that there are at least two carbon atoms between the nitrogen atom of said group and the oxygen atom of the ($C_1$-$C_4$)alkoxy or the nitrogen atom of said mono- or bis-($C_1$-$C_4$)alkylamino.

R2 as defined above, is preferably halogen, trifluoromethyl, ($C_1$-$C_4$)alkyl, ($C_1$-$C_4$)alkoxy, mono- or bis-($C_1$-$C_4$) alkylamino, monocyclic ring system containing 0-4 heteroatoms independently selected from N and O, in particular pyrrolidin-1-yl, piperidin-1-yl, morpholin-4-yl, and wherein the alkyl chains of said ($C_1$-$C_4$)alkyl, ($C_1$-$C_4$)alkoxy, mono- or bis($C_1$-$C_4$)alkylamino, can be optionally substituted with an amino, mono- or bis-($C_1$-$C_4$)alkylamino, morpholino, piperidino, pyrrolidino or piperazino group, provided that there are at least two carbon atoms between the nitrogen atom of said group and the oxygen atom of the ($C_1$-$C_4$)alkoxy or the nitrogen atom of said mono- or bis-($C_1$-$C_4$)alkylamino.

R3, as defined above, is preferably hydrogen or when n=1 is $CH_2$ and forms a cycle with R1=$CH_2$.

Examples of compounds of formula IA are:

1-(4-(trifluoromethyl)benzyl)-3-(2,3-dihydro-2-oxo-1H-benzo[d]imidazol-4-yl)urea
1-(2-fluoro-4-(trifluoromethyl)benzyl)-3-(2,3-dihydro-2-oxo-1H-benzo[d]imidazol-4-yl)urea
1-(2-chloro-4-(trifluoromethyl)benzyl)-3-(2,3-dihydro-2-oxo-1H-benzo[d]imidazol-4-yl)urea
1-(2-(dimethylamino)-4-(trifluoromethyl)benzyl)-3-(2,3-dihydro-2-oxo-1H-benzo[d]imidazol-4-yl)urea
1-(4-(trifluoromethyl)-2-(pyrrolidin-1-yl)benzyl)-3-(2,3-dihydro-2-oxo-1H-benzo[d]imidazol-4-yl)urea
1-(4-(trifluoromethyl)-2-(piperidin-1-yl)benzyl)-3-(2,3-dihydro-2-oxo-1H-benzo[d]imidazol-4-yl)urea
1-(4-(trifluoromethyl)-2-morpholinobenzyl)-3-(2,3-dihydro-2-oxo-1H-benzo[d]imidazol-4-yl)urea
1-(4-(trifluoromethyl)-2-(1H-1,2,4-triazol-1-yl)benzyl)-3-(2,3-dihydro-2-oxo-1H-benzo[d]imidazol-4-yl)urea
1-(4-fluorobenzyl)-3-(2,3-dihydro-2-oxo-1H-benzo[d]imidazol-4-yl)urea
1-(4-chlorobenzyl)-3-(2,3-dihydro-2-oxo-1H-benzo[d]imidazol-4-yl)urea
1-(4-chloro-2-(dimethylamino)benzyl)-3-(2,3-dihydro-2-oxo-1H-benzo[d]imidazol-4-yl)urea
1-(4-chloro-2-(pyrrolidin-1-yl)benzyl)-3-(2,3-dihydro-2-oxo-1H-benzo[d]imidazol-4-yl)urea
1-(4-chloro-2-(piperidin-1-yl)benzyl)-3-(2,3-dihydro-2-oxo-1H-benzo[d]imidazol-4-yl)urea
1-(4-(dimethylamino)benzyl)-3-(2,3-dihydro-2-oxo-1H-benzo[d]imidazol-4-yl)urea
1-(4-(pyrrolidin-1-yl)benzyl)-3-(2,3-dihydro-2-oxo-1H-benzo[d]imidazol-4-yl)urea
1-(4-(piperidin-1-yl)benzyl)-3-(2,3-dihydro-2-oxo-1H-benzo[d]imidazol-4-yl)urea
1-(4-methylbenzyl)-3-(2,3-dihydro-2-oxo-1H-benzo[d]imidazol-4-yl)urea
1-(2-(dimethylamino)-4-methylbenzyl)-3-(2,3-dihydro-2-oxo-1H-benzo[d]imidazol-4-yl)urea
1-(4-methyl-2-(piperidin-1-yl)benzyl)-3-(2,3-dihydro-2-oxo-1H-benzo[d]imidazol-4-yl)urea
1-(2,3-dihydro-2-oxo-1H-benzo[d]imidazol-4-yl)-3-((pyridin-4-yl)methyl)urea
1-((6-chloropyridin-3-yl)methyl)-3-(2,3-dihydro-2-oxo-1H-benzo[d]imidazol-4-yl)urea
1-(4-chloro-2-(3-hydroxypyrrolidin-1-yl)benzyl)-3-(2,3-dihydro-2-oxo-1H-benzo[d]imidazol-4-yl)urea
1-(5-(trifluoromethyl-furan-2-yl)-methyl)-3-(2,3-dihydro-2-oxo-1H-benzo[d]imidazol-4-yl)urea
1-(2-oxo-1,3-dihydrobenzimidazol-4-yl)-3-[[6-(trifluoromethyl)-3-pyridyl]methyl]urea
1-(2-oxo-1,3-dihydrobenzimidazol-4-yl)-3-[[2-pyrrolidin-1-yl-6-(trifluoromethyl)-3-pyridyl]methyl]urea
1-[[6-methyl-2-(1-piperidyl)-3-pyridyl]methyl]-3-(2-oxo-1,3-dihydrobenzimidazol-4-yl)urea
1-(2-oxo-1,3-dihydrobenzimidazol-4-yl)-3-[[5-(trifluoromethyl)-2-pyridyl]methyl]urea
1-[[2-isopropoxy-4-(trifluoromethyl)phenyl]methyl]-3-(2-oxo-1,3-dihydrobenzimidazol-4-yl)urea
1-[[2-isopropoxy-6-(trifluoromethyl)-3-pyridyl]methyl]-3-(2-oxo-1,3-dihydrobenzimidazol-4-yl)urea
1-[[2-dimethylamino-6-(trifluoromethyl)-3-pyridyl]methyl]-3-(2-oxo-1,3-dihydrobenzimidazol-4-yl)urea
1-[(4-tert-butylphenyl)methyl]-3-(2-oxo-1,3-dihydrobenzimidazol-4-yl)urea
1-(2-oxo-1,3-dihydrobenzimidazol-4-yl)-3-[[2-(1-piperidyl)-6-(trifluoromethyl)-3-pyridyl]methyl]urea
1-[[2-(2-dimethylaminoethoxy)-6-(trifluoromethyl)-3-pyridyl]methyl]-3-(2-oxo-1,3-dihydrobenzimidazol-4-yl)urea
1-[[2-(2-dimethylaminoethoxy)-4-(trifluoromethyl)phenyl]methyl]-3-(2-oxo-1,3-dihydrobenzimidazol-4-yl)urea
1-[(4-tert-butyl-2-chloro-phenyl)methyl]-3-(2-oxo-1,3-dihydrobenzimidazol-4-yl)urea
1-[(4-tert-butyl-2-pyrrolidin-1-yl-phenyl)methyl]-3-(2-oxo-1,3-dihydrobenzimidazol-4-yl)urea
1-(4-(trifluoromethyl)benzyl)-3-(2,3-dihydro-2-oxobenzo[d]oxazol-4-yl)urea
1-(2-fluoro-4-(trifluoromethyl)benzyl)-3-(2,3-dihydro-2-oxobenzo[d]oxazol-4-yl)urea
1-(2-chloro-4-(trifluoromethyl)benzyl)-3-(2,3-dihydro-2-oxobenzo[d]oxazol-4-yl)urea
1-(4-fluoro-2-(trifluoromethyl)benzyl)-3-(2,3-dihydro-2-oxobenzo[d]oxazol-4-yl)urea
1-(4-chloro-2-(trifluoromethyl)benzyl)-3-(2,3-dihydro-2-oxobenzo[d]oxazol-4-yl)urea
1-(2-(dimethylamino)-4-(trifluoromethyl)benzyl)-3-(2,3-dihydro-2-oxobenzo[d]oxazol-4-yl)urea
1-(4-(trifluoromethyl)-2-(pyrrolidin-1-yl)benzyl)-3-(2,3-dihydro-2-oxobenzo[d]oxazol-4-yl)urea
1-(4-(trifluoromethyl)-2-(piperidin-1-yl)benzyl)-3-(2,3-dihydro-2-oxobenzo[d]oxazol-4-yl)urea
1-(4-(trifluoromethyl)-2-morpholinobenzyl)-3-(2,3-dihydro-2-oxobenzo[d]oxazol-4-yl)urea
1-(4-chlorobenzyl)-3-(2,3-dihydro-2-oxobenzo[d]oxazol-4-yl)urea
1-(4-(trifluoromethyl)benzyl)-3-(2,3-dihydro-2-oxobenzo[d]oxazol-7-yl)urea
1-(4-(trifluoromethyl)-2-(pyrrolidin-1-yl)benzyl)-3-(2,3-dihydro-2-oxobenzo[d]oxazol-7-yl)urea
1-(4-(trifluoromethyl)-2-(piperidin-1-yl)benzyl)-3-(2,3-dihydro-2-oxobenzo[d]oxazol-7-yl)urea
1-(2-oxo-3H-1,3-benzoxazol-7-yl)-3-[[6-(trifluoromethyl)-3-pyridyl]methyl]urea
1-(2-oxo-3H-1,3-benzoxazol-7-yl)-3-[[5-(trifluoromethyl)-2-furyl]methyl]urea.

Examples of compounds of formula IB are:

1-(4-(trifluoromethyl)benzyl)-3-(3,4-dihydro-3-oxo-2H-benzo[b][1,4]oxazin-5-yl)urea
1-(4-(trifluoromethyl)-2-(pyrrolidin-1-yl)benzyl)-3-(3,4-dihydro-3-oxo-2H-benzo[b][1,4]oxazin-5-yl)urea
1-(4-(trifluoromethyl)-2-(piperidin-1-yl)benzyl)-3-(3,4-dihydro-3-oxo-2H-benzo[b][1,4]oxazin-5-yl)urea.

Examples of compounds of formula IC are:

1-(4-(trifluoromethyl)benzyl)-3-(3,4-dihydro-3-oxo-2H-benzo[b][1,4]oxazin-8-yl)urea
1-(2-(dimethylamino)-4-(trifluoromethyl)benzyl)-3-(3,4-dihydro-3-oxo-2H-benzo[b][1,4]oxazin-8-yl)urea
1-(4-(trifluoromethyl)-2-(pyrrolidin-1-yl)benzyl)-3-(3,4-dihydro-3-oxo-2H-benzo[b][1,4]oxazin-8-yl)urea
1-(4-(trifluoromethyl)-2-(piperidin-1-yl)benzyl)-3-(3,4-dihydro-3-oxo-2H-benzo[b][1,4]oxazin-8-yl)urea
1-(4-chlorobenzyl)-3-(3,4-dihydro-3-oxo-2H-benzo[b][1,4]oxazin-8-yl)urea
1-(4-chloro-2-(dimethylamino)benzyl)-3-(3,4-dihydro-3-oxo-2H-benzo[b][1,4]oxazin-8-yl)urea
1-(4-chloro-2-(pyrrolidin-1-yl)benzyl)-3-(3,4-dihydro-3-oxo-2H-benzo[b][1,4]oxazin-8-yl)urea
1-(4-chloro-2-(piperidin-1-yl)benzyl)-3-(3,4-dihydro-3-oxo-2H-benzo[b][1,4]oxazin-8-yl)urea
1-(4-methyl-2-(piperidin-1-yl)benzyl)-3-(3,4-dihydro-3-oxo-2H-benzo[b][1,4]oxazin-8-yl)urea
1-((6-chloropyridin-3-yl)methyl)-3-(3,4-dihydro-3-oxo-2H-benzo[b][1,4]oxazin-8-yl)urea 1-(3-oxo-4H-1,4-benzoxazin-8-yl)-3-[[5-(trifluoromethyl)-2-furyl]methyl]urea
1-(3-oxo-4H-1,4-benzoxazin-8-yl)-3-[[6-(trifluoromethyl)-3-pyridyl]methyl]urea)
1-(3-oxo-4H-1,4-benzoxazin-8-yl)-3-[[2-(1-piperidyl)-6-(trifluoromethyl)-3-pyridyl]methyl]urea
1-(3-oxo-4H-1,4-benzoxazin-8-yl)-3-(p-tolylmethyl)urea
1-[[6-methyl-2-(1-piperidyl)-3-pyridyl]methyl]-3-(3-oxo-4H-1,4-benzoxazin-8-yl)urea
1-[[2-isopropoxy-4-(trifluoromethyl)phenyl]methyl]-3-(3-oxo-4H-1,4-benzoxazin-8-yl)urea
1-[[2-methoxy-6-(trifluoromethyl)-3-pyridyl]methyl]-3-(3-oxo-4H-1,4-benzoxazin-8-yl)urea
1-(3-oxo-4H-1,4-benzoxazin-8-yl)-3-[[5-(trifluoromethyl)-2-pyridyl]methyl]urea
1-[(2-isopropoxy-4-methyl-phenyl)methyl]-3-(3-oxo-4H-1,4-benzoxazin-8-yl)urea
1-[(2-isopropoxy-6-methyl-3-pyridyl)methyl]-3-(3-oxo-4H-1,4-benzoxazin-8-yl)urea
1-[[2-dimethylamino-6-(trifluoromethyl)-3-pyridyl]methyl]-3-(3-oxo-4H-1,4-benzoxazin-8-yl)urea
1-(3-oxo-4H-1,4-benzoxazin-8-yl)-3-[[2-pyrrolidin-1-yl-6-(trifluoro methyl)-3-pyridyl]methyl]urea
1-[[2-(imidazol-1-yl)-4-(trifluoromethyl)phenyl]methyl]-3-(3-oxo-4H-1,4-benzoxazin-8-yl)urea
1-[(4-tert-butylphenyl)methyl]-3-(3-oxo-4H-1,4-benzoxazin-8-yl)urea
1-[(4-methyl-2-pyrrolidin-1-yl-phenyl)methyl]-3-(3-oxo-4H-1,4-benzoxazin-8-yl)urea
1-[[2-(2-dimethylaminoethoxy)-6-(trifluoromethyl)-3-pyridyl]methyl]-3-(3-oxo-4H-1,4-benzoxazin-8-yl)urea
1-[[2-(2-dimethylaminoethoxy)-4-(trifluoromethyl)phenyl]methyl]-3-(3-oxo-4H-1,4-benzoxazin-8-yl)urea.

According to a second preferred embodiment, the invention relates to compounds of formula (ID), (1E) or (1F) wherein Y is A or B, W is NH, Q is a bond and R3 is hydrogen clic ring system containing 0-4 heteroatoms independently selected from N and O, in particular pyrrolidin-1-yl, piperidin-1-yl, morpholin-4-yl, and wherein the alkyl chains of said $(C_1-C_4)$alkyl, $(C_1-C_4)$alkoxy, mono- or bis$(C_1-C_4)$alkylamino, can be optionally substituted with an amino, mono- or bis-$(C_1-C_4)$alkylamino, morpholino, piperidino, pyrrolidino or piperazino group, provided that there are at least two carbon atoms between the nitrogen atom of said group and the oxygen atom of the $(C_1-C_4)$alkoxy or the nitrogen atom of said mono- or bis-$(C_1-C_4)$alkylamino.

R2 is halogen, trifluoromethyl, $(C_1-C_4)$alkyl, $(C_1-C_4)$alkoxy, mono- or bis-$(C_1-C_4)$alkylamino, monocyclic ring system containing 0-4 heteroatoms independently selected from N and O, in particular pyrrolidin-1-yl, piperidin-1-yl, morpholin-4-yl, and wherein the alkyl chains of said $(C_1-C_4)$alkyl, $(C_1-C_4)$alkoxy, mono- or bis$(C_1-C_4)$alkylamino, can be optionally substituted with an amino, mono- or bis-$(C_1-C_4)$alkylamino, morpholino, piperidino, pyrrolidino or piperazino group, provided that there are at least two carbon atoms between the nitrogen atom of said group and the oxygen atom of the $(C_1-C_4)$alkoxy or the nitrogen atom of said mono- or bis-$(C_1-C_4)$alkylamino.

The formula 1D and 1E substantially corresponds to formula I wherein U1=U2=U3=U4=U5 are CH.

Examples of compounds of formula ID-F are:
2-(4-(trifluoromethyl)phenyl)-N-(2,3-dihydro-2-oxo-1H-benzo[d]imidazol-4-yl)acetamide
2-(4-(trifluoromethyl)phenyl)-N-(2,3-dihydro-2-oxobenzo[d]oxazol-4-yl)acetamide
2-(4-(trifluoromethyl)phenyl)-N-(2,3-dihydro-2-oxobenzo[d]oxazol-7-yl)acetamide
2-(4-(trifluoromethyl)phenyl)-N-(3,4-dihydro-3-oxo-2H-benzo[b][1,4]oxazin-5-yl)acetamide.

According to a third preferred embodiment, the invention relates to compounds of formula (IG), (IH) or (IL) wherein Y is A, C or E, Q is NH and R3 is hydrogen

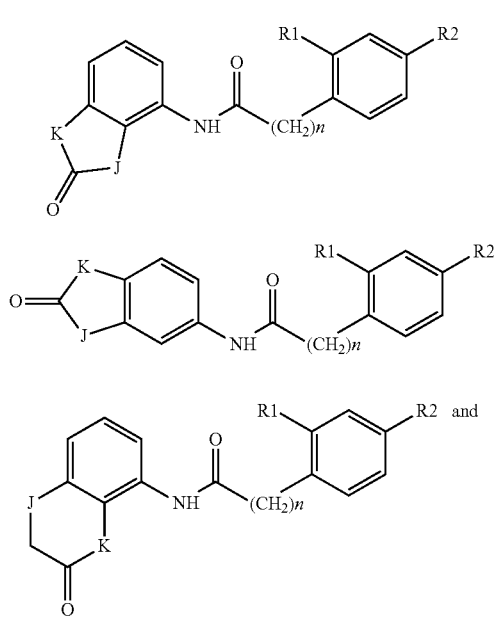

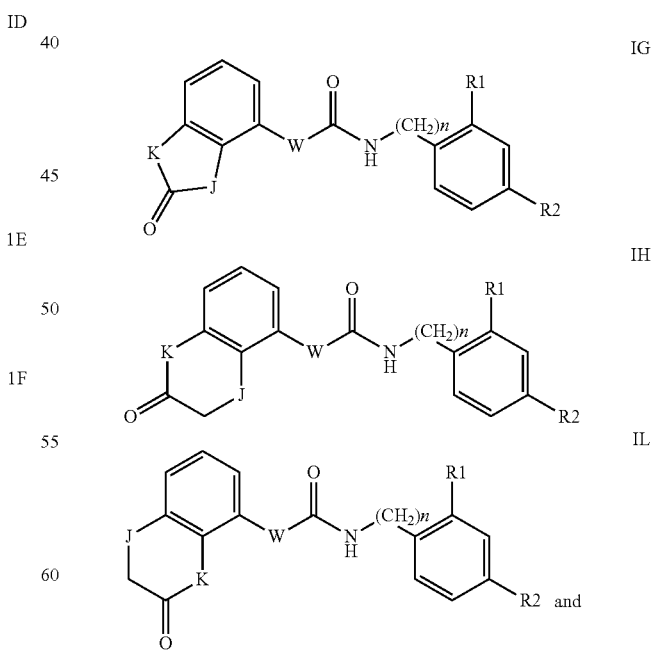

J and K are independently NH or O;
n is 0 or 1;
R1 is hydrogen, halogen, trifluoromethyl, $(C_1-C_4)$alkyl, $(C_1-C_4)$alkoxy, mono- or bis-$(C_1-C_4)$alkylamino, monocy- J and K are independently NH or O;
W is O or a bond;
n is 0 or 1.

R1 is hydrogen, halogen, trifluoromethyl, ($C_1$-$C_4$)alkyl, ($C_1$-$C_4$)alkoxy, mono- or bis-($C_1$-$C_4$)alkylamino, monocyclic ring system containing 0-4 heteroatoms independently selected from N and O, in particular pyrrolidin-1-yl, piperidin-1-yl, morpholin-4-yl, and wherein the alkyl chains of said ($C_1$-$C_4$)alkyl, ($C_1$-$C_4$)alkoxy, mono- or bis($C_1$-$C_4$)alkylamino, can be optionally substituted with an amino, mono- or bis-($C_1$-$C_4$)alkylamino, morpholino, piperidino, pyrrolidino or piperazino group, provided that there are at least two carbon atoms between the nitrogen atom of said group and the oxygen atom of the ($C_1$-$C_4$)alkoxy or the nitrogen atom of said mono- or bis-($C_1$-$C_4$)alkylamino.

R2 is halogen, trifluoromethyl, ($C_1$-$C_4$)alkyl, ($C_1$-$C_4$)alkoxy, mono- or bis-($C_1$-$C_4$)alkylamino, monocyclic ring system containing 0-4 heteroatoms independently selected from N and O, in particular pyrrolidin-1-yl, piperidin-1-yl, morpholin-4-yl, and wherein the alkyl chains of said ($C_1$-$C_4$)alkyl, ($C_1$-$C_4$)alkoxy, mono- or bis($C_1$-$C_4$)alkylamino, can be optionally substituted with an amino, mono- or bis-($C_1$-$C_4$)alkylamino, morpholino, piperidino, pyrrolidino or piperazino group, provided that there are at least two carbon atoms between the nitrogen atom of said group and the oxygen atom of the ($C_1$-$C_4$)alkoxy or the nitrogen atom of said mono- or bis-($C_1$-$C_4$)alkylamino.

With the proviso that when n is 0, Q is NH and W is a bond, then Y is different from A or E.

The formula IC substantially corresponds to formula I wherein U1=U2=U3=U4=U5 are CH.

Examples of compounds of formula IG-L are:
N-(4-(trifluoromethyl)benzyl)-2,3-dihydro-2-oxobenzo[d] oxazole-4-carboxamide
N-(4-(trifluoromethyl)-2-(piperidin-1-yl)benzyl)-2,3-dihydro-2-oxobenzo[d]oxazole-4-carboxamide
N-(4-(trifluoromethyl)-2-morpholinobenzyl)-2,3-dihydro-2-oxobenzo[d]oxazole-4-carboxamide
N-(4-(trifluoromethyl)benzyl)-3,4-dihydro-3-oxo-2H-benzo [b][1,4]oxazine-5-carboxamide
N-(4-(trifluoromethyl)-2-(piperidin-1-yl)benzyl)-3,4-dihydro-3-oxo-2H-benzo[b][1,4]oxazine-5-carboxamide
N-(4-(trifluoromethyl)-2-(piperidin-1-yl)benzyl)-3,4-dihydro-3-oxo-2H-benzo[b][1,4]oxazine-8-carboxamide
3,4-dihydro-3-oxo-2H-benzo[b][1,4]oxazin-5-yl 4-(trifluoromethyl)benzylcarbamate The compounds of formula (IA), (IB) and (IC) are ureas that can be prepared by reaction of a compound of formula 1, 1' or 1'', respectively,

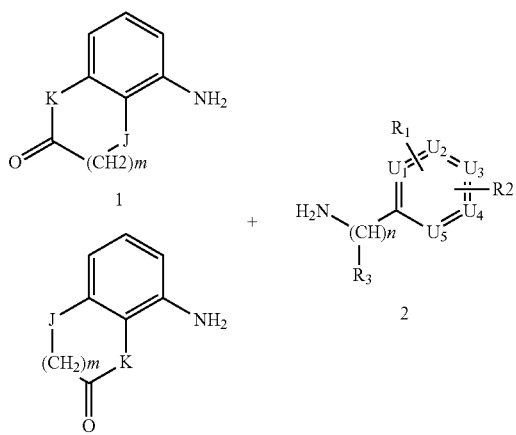

wherein K and Y are as above defined, with a compound of formula 2

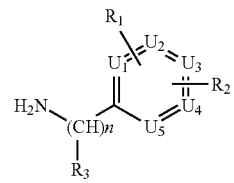

wherein $R_1$, $R_2$, $R_3$, U1, U2, U3, U4, U5 and n are as above defined and where one of 1, 1', 1'' and 2, more commonly 2, is firstly converted into isocyanate using triphosgene. Alternatively, N,N'-carbonyldiimidazole (CDI) was used to form the uredyl derivative of one of the two amines and which reacts with the other to give the desired urea. Compounds 1, 1', 1'' and 2 are prepared by standard procedures.

The compounds of formula (ID-L) are amides or carbamates that can be prepared by standard procedures.

In a further aspect of the present invention, compounds of formula I bearing a solubilizing amine may be prepared in the form of a pharmaceutically acceptable salt, especially an acid addition salt.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include addition salts which may, for example, be formed by mixing a solution of the compound according to the invention with a solution of a pharmaceutically acceptable acid such as hydrochloric acid, sulphuric acid, nitric acid, maleic acid, citric acid, tartaric acid, phosphoric acid, p-toluenesulphonic acid, benzenesulphonic acid. Preferred pharmaceutically salts of the compounds of the present invention are those with the inorganic acids.

The salts may be formed by conventional means, such as by reacting the free base form of the suitable compounds of formula I with one or more equivalents of the appropriate acid in a solvent or medium in which the salt is insoluble or in a solvent such as water which is removed under vacuum.

Compositions of the Invention

The present invention also provides pharmaceutical compositions that comprise compounds of the present invention. The pharmaceutical compositions comprise compounds of the present invention that may be formulated together with one or more non-toxic pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), buccally or as an oral or nasal spray.

Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents that delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragées, capsules, pills and granules can be prepared with coatings and shells such as enteric coatings and other coatings well-known in the pharmaceutical formulating art. They may optionally contain opacifying agents and may also be of a composition such that they release the active ingredient (s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals, which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants that may be required. Ophthalmic formulations, eye ointments, powders and solutions are also contemplated as being within the scope of this invention.

In the treatment of painful conditions such as those listed below, a suitable indicated dosage level is about 0.1 mg to 2000 mg/day, preferably from about 5 mg to 1000 mg per day. The compounds may be administered on a regimen of 1 to 3 times a day.

It will be appreciated that the amount of a compound of formula I required for use in any treatment will vary not only with the particular compounds or compositions selected but also with the route of administration, the nature of the condition being treated, and the age and condition of the patient.

The agents of invention are useful vanilloid receptor antagonists for the treatment of pain of various genesis or aetiology and as anti-inflammatory agents for the treatment of inflammatory reactions, diseases or conditions. They are useful for the treatment of inflammatory pain, for the treatment of hyperalgesia, and in particular for the treatment of severe chronic pain. They are, for example, useful for the treatment of pain, inflammation consequential to trauma, e.g. associated with burns or subsequent to surgical intervention, e.g. as post-operative analgesics, as well as for the treatment of inflammatory pain of diverse genesis, e.g. for the treatment of osteoarthritis and rheumatoid arthritis. They are suitable as analgesics for the treatment of pain associated with, e.g. angina or cancer.

Other forms of pain associated with the activity of TRPV1 are headache, dental pain, pelvic pain, migraine, mastalgia and visceral pain. The disorders in which TRPV1 is involved are not limited to pain. Such diseases include: nerve-related diseases, e.g. neuropathies, nerve injury and stroke; irritable bowel syndrome; gastrointestinal disorders, e.g. gastro-oesophageal reflux disease, Crohn's disease; respiratory diseases, e.g. asthma, chronic obstructive pulmonary disease, cough; urinary incontinence; urinary bladder hypersensitiveness; skin diseases, e.g. psoriasis, dermatitis; cardiac diseases e.g. myocardial ischemia; hair growth related disorders e.g. hirsutism, alopecia; rhinitis; pancreatitis; vulvodynia; psychiatric disorders, e.g. anxiety or fear; obesity.

The compounds of the present invention have potent analgesic effect and potential anti-inflammatory activity and their pharmaceutically formulations are thought to alleviate or to treat in particular neuropathic pain conditions such as diabetic neuropathy and post-herpetic neuralgia, urinary incontinence and cough.

The compounds of the invention are also useful as active ingredients of pharmaceutical compositions for the systemic and topical treatment of Dry Eye.

The invention will be now illustrated by means of the following examples.

EXAMPLES

All commercially available compounds were purchased from Vendors and were used without further purification. Reaction courses were monitored by thin-layer chromatography on silica gel (precoated $F_{254}$ Merck plates), the spots were examined with UV light and visualized with aqueous $KMnO_4$. Flash chromatography was performed using Merck silica gel (230-240 mesh). $^1$H-NMR spectra were recorded on Varian 400 MHz spectrometer or Varian 200 MHz using TMS as internal standard. Mass spectra were obtained with a Waters-Micromass ZMD spectrometer.

Example 1

1-(4-(trifluoromethyl)benzyl)-3-(2,3-dihydro-2-oxo-1H-benzo[d]imidazol-4-yl)urea (scheme 1)

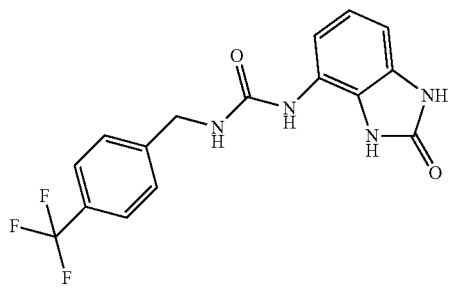 [SMILES: O=C(NCc1ccc(C(F)(F)F)cc1)Nc1cccc2[nH]c(=O)[nH]c12]

Preparation of
4-nitro-1H-benzo[d]imidazol-2(3H)-one 4a (scheme 2)

To 3-nitro-1,2-phenylenediamine 3a (2 g, 13.06 mmol) dissolved in THF (50 ml) was added in one portion DCI (1.5 equiv., 19.6 mmol, 3.176 g) and the reaction was refluxed for 2 hours. (TLC AcOEt 1/petroleum ether 1). The reaction was filtrated and the yellow solid material was washed with THF and diethyl ether obtaining 2 g of the product that was used for the following step without further purification. Yield=88% $^1$HNMR (DMSO, 200 MHz) δ 7.11 (1H, t, J=7.6 Hz), 7.31 (1H, dd, J=7.8 Hz, J'=1.2 Hz), 7.74 (1H, dd, J=8.6 Hz, J'=1 Hz), 11.45 (2H, bs)

Preparation of
4-amino-1H-benzo[d]imidazol-2(3H)-one 1a
(scheme 2)

To compound 4a (2 g, 11.6 mmol) dissolved in a mixture of 4/1 MeOH/THF (100 ml) was added C/Pd 10% (500 mg) and the reaction was hydrogenated at 60 psi overnight. (TLC AcOEt 9/MeOH 1) The reaction was filtrated through a pad of Celite and the filtrate was evaporated under vacuum. The crude solid was crystallized from ether giving 1.5 g of a white solid. Yield=88%. $^1$HNMR (DMSO, 200 MHz) δ 4.84 (2H, bs), 6.22 (2H, m), 6.65 (1H, t, J=8 Hz), 9.98 (1H, bs), 10.33 (1H, bs)

Preparation of 1-(4-(trifluoromethyl)benzyl)-3-(2,3-dihydro-2-oxo-1H-benzo[d]imidazol-4-yl)urea Commercially available 4-trifluoromethylbenzylamine (0.5 ml, 3.5 mmol) was dissolved in 20 ml of AcOEt and at 0° C. triphosgene (1 g, 3.5 mmol) was added to the solution. The mixture was warmed at 80° C. for 4 hours then evaporated and the residue was dissolved in 5 ml of DMF. The solution of the isocyanate was added dropwise to a solution in DMF (5 ml) of compound 1a (350 mg, 2.33 mmol) and the mixture was warmed at 80° C. for 8 hours. (TLC AcOEt 9.5/MeOH 0.5). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 290 mg of a white solid. Yield=36% $^1$HNMR (DMSO, 400 MHz) δ 4.40 (2H, d, J=6

Hz), 6.62 (1H, d, J=7.2 Hz), 6.84 (2H, m), 6.96 (1H, d, J=8 Hz), 7.54 (2H, d, J=8 Hz), 7.70 (2H, d, J=8.4 Hz), 8.30 (1H, s), 9.99 (1H, bs), 10.60 (1H, bs); [M$^{+1}$] 351.1 (C$_{16}$H$_{13}$F$_3$N$_4$O$_2$ requires 350.3).

Example 2

1-(2-fluoro-4-(trifluoromethyl)benzyl)-3-(2,3-dihydro-2-oxo-1H-benzo[d]imidazol-4-yl)urea (scheme 1)

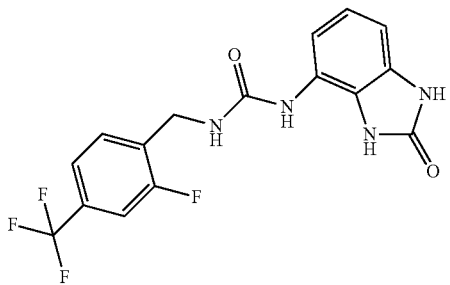 [SMILES: O=C(NCc1ccc(C(F)(F)F)cc1F)Nc1cccc2[nH]c(=O)[nH]c12]

Commercially available 2-fluoro-4-trifluoromethylbenzylamine (0.5 ml, 3.7 mmol) was dissolved in 20 ml of AcOEt and at 0° C. triphosgene (1.12 g, 3.7 mmol) was added to the solution. The mixture was warmed at 80° C. for 4 hours then evaporated and the residue was dissolved in 5 ml of DMF. The solution of the isocyanate was added dropwise to a solution in DMF (5 ml) of compound 1a (360 mg, 2.4 mmol) and the mixture was warmed at 80° C. for 8 hours. (TLC AcOEt 9.5/MeOH 0.5). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 210 mg of a white solid. Yield=28% $^1$HNMR (DMSO, 400 MHz) δ 4.42 (2H, d, J=6 Hz), 6.63 (1H, dd, J=8 Hz, J'=1.2 Hz), 6.85 (2H, m), 6.95 (1H, d, J=8 Hz), 7.62 (3H, m), 8.35 (1H, bs), 9.99 (1H, bs), 10.61 (1H, bs); [M$^{+1}$] 369.1 (C$_{16}$H$_{12}$F$_4$N$_4$O$_2$ requires 368.29).

Example 3

1-(2-chloro-4-(trifluoromethyl)benzyl)-3-(2,3-dihydro-2-oxo-1H-benzo[d]imidazol-4-yl)urea (scheme 1)

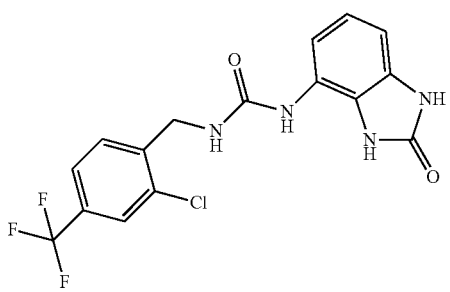 [SMILES: O=C(NCc1ccc(C(F)(F)F)cc1Cl)Nc1cccc2[nH]c(=O)[nH]c12]

Commercially available 2-chloro-4-trifluoromethylbenzylamine (700 mg, 3.3 mmol) was dissolved in 20 ml of AcOEt and at 0° C. triphosgene (989 mg, 3.3 mmol) was added to the solution. The mixture was warmed at 80° C. for 4 hours then evaporated and the residue was dissolved in 5 ml of DMF. The solution of the isocyanate was added dropwise to a solution in DMF (5 ml) of compound 1a (319 mg, 2.14 mmol) and the mixture was warmed at 80° C. for 8 hours. (TLC AcOEt 9.5/MeOH 0.5). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 140 mg of a white solid. Yield=18% $^1$HNMR (DMSO, 400 MHz) δ 4.44 (2H, d, J=5.6 Hz), 6.64 (1H, d, J=7.2 Hz), 6.84 (1H, t, J=8.4 Hz), 6.89 (1H, t), 6.96 (1H, d, J=8 Hz), 7.64 (1H, d, J=8.4 Hz), 7.74 (1H, d), 7.86 (1H, s), 8.43 (1H, bs), 9.99 (1H, bs), 10.61 (1H, bs); [M$^{+1}$] 385.0 (C$_{16}$H$_{12}$ClF$_3$N$_4$O$_2$ requires 384.74).

Example 4

1-(2-(dimethylamino)-4-(trifluoromethyl)benzyl)-3-(2,3-dihydro-2-oxo-1H-benzo[d]imidazol-4-yl)urea (scheme 1)

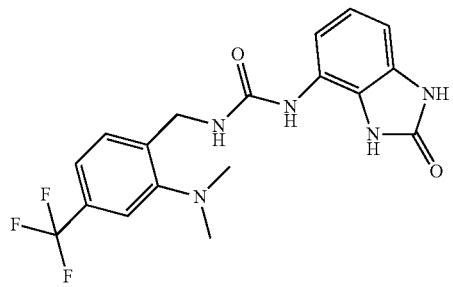 [SMILES: CN(C)c1cc(C(F)(F)F)ccc1CNC(=O)Nc1cccc2[nH]c(=O)[nH]c12]

Preparation of 2-(dimethylamino)-4-(trifluoromethyl)benzonitrile 14a (scheme 7)

To commercially available 2-chloro-4-trifluoromethylbenzonitrile 13 (0.5 ml, 3.6 mmol) dimethylamine (4 equiv., 0.95 ml) was added and the solution was heated in closed vessel at 80° C. overnight. The reaction was evaporated and the residue was dissolved in AcOEt and washed with water and brine. The organic phase was evaporated obtaining 730 mg of a pale yellow oil. Yield=94% $^1$HNMR (CDCl$_3$, 200 MHz) δ 3.13 (6H, s), 7.05 (1H, bs), 7.59 (1H, dd, J=8.4 Hz, J'=0.6 Hz), 7.99 (1H, bs)

Preparation of 2-(aminomethyl)-5-(trifluoromethyl)-N,N-dimethyl-benzenamine 2a (scheme 7)

Benzonitrile 14a (730 mg, 3.4 mmol) dissolved in 5 ml of ether was added dropwise at 0° C. to LiAlH$_4$ (2 equiv., 260 mg) suspended in diethyl ether (40 ml). The mixture was stirred at room temperature for 24 hours. The reaction was quenched by addition of water and filtrated and the salts were washed with ether. The organic phase was separated, anhydrified and evaporated giving 720 mg of a yellow oil. Yield=97% $^1$HNMR (CDCl$_3$, 200 MHz) δ 2.78 (6H, s), 3.95 (2H, s), 7.36 (2H, m), 7.49 (1H, d)

Preparation of 1-(2-(dimethylamino)-4-(trifluoromethyl)benzyl)-3-(2,3-dihydro-2-oxo-1H-benzo[d]imidazol-4-yl)urea Amine 2a (1.3 g, 5.9 mmol) was dissolved in 40 ml of AcOEt and at 0° C. triphosgene (1.75 g, 5.9 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1a (860 mg, 5.77 mmol) and the mixture was warmed at 80° C. for 8 hours. (TLC AcOEt). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 650 mg of a yellow solid. Yield=28% $^1$HNMR (DMSO, 200 MHz) δ 2.51 (6H, bs), 4.43 (2H, d, J=5.6 Hz), 6.62 (1H, dd, J=7.6 Hz, J'=1 Hz), 6.82 (2H, m), 6.97 (1H, dd, J=8 Hz, J'=1 Hz), 7.32 (1H, s), 7.39 (1H, d), 7.49 (1H, d), 8.35 (1H, bs), 9.99 (1H, bs), 10.59 (1H, bs); [M$^{+1}$] 394.1 ($C_{18}H_{18}F_3N_5O_2$ requires 393.36).

Example 5

1-(4-(trifluoromethyl)-2-(pyrrolidin-1-yl)benzyl)-3-(2,3-dihydro-2-oxo-1H-benzo[d]imidazol-4-yl)urea (scheme 1)

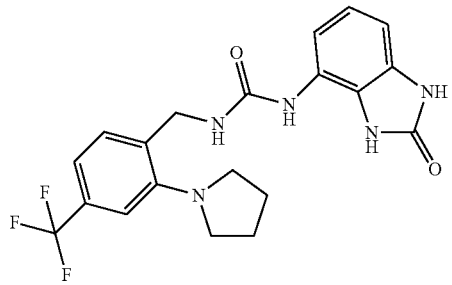 [SMILES: O=C(NCc1ccc(C(F)(F)F)cc1N1CCCC1)Nc1cccc2[nH]c(=O)[nH]c12]

Preparation of 4-(trifluoromethyl)-2-(pyrrolidin-1-yl) benzonitrile 14b (scheme 7)

To commercially available 2-chloro-4-trifluoromethylbenzonitrile 13 (1 ml, 7.2 mmol) pyrrolidine (4 equiv., 2.38 ml) was added and the solution was heated at 80° C. overnight. The reaction was evaporated and the residue was dissolved in AcOEt and washed with water and brine. The organic phase was evaporated obtaining 940 mg of a yellow solid. Yield=54% $^1$HNMR (DMSO, 200 MHz) δ 1.95 (4H, m), 3.58 (4H, m), 6.94 (2H, m), 7.73 (1H, dd, J=8 Hz, J'=0.8 Hz).

Preparation of (4-(trifluoromethyl)-2-(pyrrolidin-1-yl)phenyl)-methanamine 2b

Benzonitrile 14b (940 mg, 3.9 mmol) dissolved in 5 ml of ether was added dropwise at 0° C. to LiAlH$_4$ (2 equiv., 297 mg) suspended in diethyl ether (40 ml). The mixture was stirred at room temperature for 24 hours. The reaction was quenched by addition of water and filtrated and the salts were washed with ether. The organic phase was separated, anhydrified and evaporated giving 1 g of a yellow oil. Yield=99% $^1$HNMR (DMSO, 200 MHz) δ 1.88 (4H, m), 3.17 (4H, m), 3.76 (2H, s), 7.00 ((1H, s), 7.14 (1H, m), 7.59 (1H, d, J=8.2 Hz)

Preparation of 1-(4-(trifluoromethyl)-2-(pyrrolidin-1-yl)benzyl)-3-(2,3-dihydro-2-oxo-1H-benzo[d]imidazol-4-yl)urea Amine 2b (0.5 ml, 2 mmol) was dissolved in 20 ml of AcOEt and at 0° C. triphosgene (580 mg, 2 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1a (296 mg, 1.99 mmol) and the mixture was warmed at 80° C. for 8 hours. (TLC AcOEt 9.5/MeOH 0.5). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 170 mg of a yellow solid. Yield=20% $^1$HNMR (DMSO, 400 MHz) δ 1.91 (4H, bs), 3.22 (4H, bs), 4.38 (2H, d, J=5.2 Hz), 6.62 (1H, d, J=8 Hz), 6.72 (1H, t), 6.83 (1H, t), 6.95 (1H, d, J=8 Hz), 7.08 (1H, s), 7.18 (1H, d, J=7.6 Hz), 7.45 (1H, d, J=7.6 Hz), 8.35 (1H, bs), 9.98 (1H, bs), 10.60 (1H, bs); [M$^{+1}$] 420.18 ($C_{20}H_{20}F_3N_5O_2$ requires 419.4).

Example 6

1-(4-(trifluoromethyl)-2-(piperidin-1-yl)benzyl)-3-(2,3-dihydro-2-oxo-1H-benzo[d]imidazol-4-yl)urea (scheme 1)

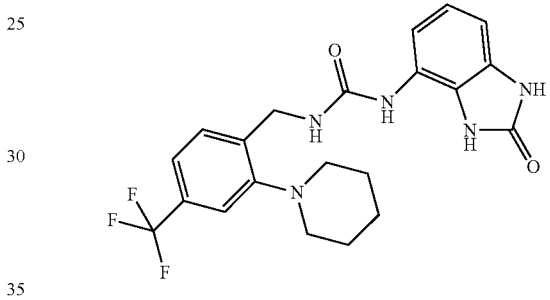

Preparation of 4-(trifluoromethyl)-2-(piperidin-1-yl) benzonitrile 14c (scheme 7)

To commercially available 2-chloro-4-trifluoromethylbenzonitrile 13 (1 ml, 7.2 mmol) was added piperidine (4 equiv., 2.8 ml) and the solution was heated at 80° C. overnight. The reaction was evaporated and the residue was dissolved in AcOEt and washed with water and brine. The organic phase was evaporated obtaining 1 g of a yellow oil. Yield=56% $^1$HNMR (DMSO, 200 MHz) δ 1.60 (6H, m), 3.20 (4H, m), 7.34 (2H, m), 7.89 (1H, dd, J=8.6 Hz, J'=0.4 Hz)

Preparation of (4-(trifluoromethyl)-2-(piperidin-1-yl) phenyl)-methanamine 2c

Benzonitrile 14c (1 g, 4 mmol) dissolved in 5 ml of ether was added dropwise at 0° C. to LiAlH$_4$ (2 equiv., 305 mg) suspended in diethyl ether (40 ml). The mixture was stirred at room temperature for 24 hours. The reaction was quenched by addition of water and filtrated and the salts were washed with ether. The organic phase was separated, anhydrified and evaporated giving 980 mg of a yellow oil. Yield=95% $^1$HNMR (DMSO, 200 MHz) δ 1.57 (6H, m), 1.80 (2H, bs), 2.81 (4H, m), 3.78 (2H, s), 7.23 (1H, s), 7.35 (1H, d, J=7.8 Hz), 7.70 (1H, d, J=8.2 Hz)

Preparation of 1-(4-(trifluoromethyl)-2-(piperidin-1-yl)benzyl)-3-(2,3-dihydro-2-oxo-1H-benzo[d]imidazol-4-yl)urea Amine 2c (500 mg, 1.9 mmol) was dissolved in 20 ml of AcOEt and at 0° C. triphosgene (580 mg, 2 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1a (265 mg, 1.78 mmol) and the mixture was warmed at 80° C. for 8 hours. (TLC AcOEt 9.5/MeOH 0.5). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 140 mg of a pale yellow solid. Yield=18% $^1$HNMR (DMSO, 400 MHz) δ 1.54 (2H, m), 1.68 (4H, m), 2.85 (4H, m), 4.42 (2H, d, J=6 Hz), 6.63 (1H, d, J=7.6 Hz), 6.76 (1H, t), 6.84 (1H, t, J=8.4 Hz), 6.95 (1H, d, J=8.4 Hz), 7.31 (1H, s), 7.41 (1H, d), 7.52 (1H, d, J=8.4 Hz), 8.33 (1H, s), 10.01 (1H, bs), 10.60 (1H, bs); [M$^{+1}$] 434.11 ($C_{21}H_{22}F_3N_5O_2$ requires 433.43).

Example 7

1-(4-(trifluoromethyl)-2-(4-morpholino)benzyl)-3-(2,3-dihydro-2-oxo-1H-benzo[d]imidazol-4-yl)urea (scheme 1)

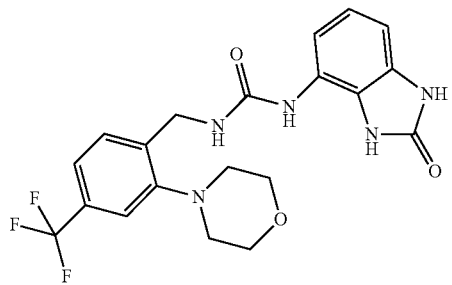 [SMILES: O=C(NCc1ccc(C(F)(F)F)cc1N1CCOCC1)Nc1cccc2[nH]c(=O)[nH]c12]

Preparation of 4-(trifluoromethyl)-2-(4-morpholino)benzonitrile 14d (scheme 7)

To commercially available 2-chloro-4-trifluoromethylbenzonitrile 13 (4 ml, 29 mmol) morpholine (4 equiv., 10 ml) was added and the solution was heated at 80° C. overnight. The reaction was evaporated and the residue was dissolved in AcOEt and washed with water and brine. The organic phase was evaporated obtaining 6.19 g of a yellow oil. Yield=83% $^1$HNMR (DMSO, 200 MHz) δ 3.24 (4H, m), 3.75 (4H, m), 7.94 (1H, m), 8.23 (1H, m).

Preparation of (4-(trifluoromethyl)-2-(4-morpholino)phenyl)methanamine 2d

Benzonitrile 14d (6.19 g, 24.2 mmol) dissolved in 15 ml of ether was added dropwise at 0° C. to LiAlH$_4$ (2 equiv., 1.83 g) suspended in diethyl ether (60 ml). The mixture was stirred at room temperature for 24 hours. The reaction was quenched by addition of water and filtrated and the salts were washed with ether. The organic phase was separated, anhydrified and evaporated giving 5.3 g of a yellow oil. Yield=84% $^1$HNMR (DMSO, 200 MHz) δ 2.88 (4H, m), 3.20 (2H, bs), 3.72 (4H, m), 3.77 (2H, s), 7.27 (1H, s), 7.38 (1H, dd, J=7.8 Hz, J'=1 Hz), 7.72 (1H, d, J=8 Hz)

Preparation of 1-(4-(trifluoromethyl)-2-(4-morpholino)benzyl)-3-(2,3-dihydro-2-oxo-1H-benzo[d]imidazol-4-yl)urea Amine 2d (300 mg, 1.15 mmol) was dissolved in 20 ml of AcOEt and at 0° C. triphosgene (350 mg, 1 equiv.) was added to the solution. The mixture was warmed at 80° C. for 4 hours then evaporated and the residue was dissolved in 5 ml of DMF. The solution of the isocyanate was added dropwise to a solution in DMF (10 ml) of compound 1a (200 mg, 1.3 mmol) and the mixture was warmed at 80° C. for 8 hours. (TLC AcOEt 9.5/MeOH 0.5). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 100 mg of a pale yellow solid. Yield=20% $^1$HNMR (DMSO, 200 MHz) δ 2.91 (4H, m), 3.76 (4H, m), 4.44 (2H, d, J=5.6 Hz), 6.63 (1H, d, J=7.6 Hz), 6.88 (3H, m), 7.64 (1H, d, J=8.2 Hz), 7.73 (1H, d), 7.85 (1H, bs), 8.44 (1H, bs), 9.99 (1H, bs), 10.60 (1H, bs); [M$^{+1}$] 436.2 ($C_{20}H_{20}F_3N_5O_3$ requires 435.4).

Example 8

1-(4-(trifluoromethyl)-2-(1H-1,2,4-triazol-1-yl)benzyl)-3-(2,3-dihydro-2-oxo-1H-benzo[d]imidazol-4-yl)urea (scheme 1)

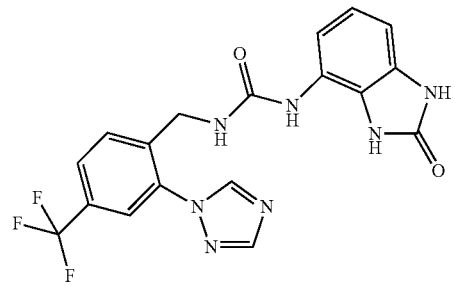 [SMILES: O=C(NCc1ccc(C(F)(F)F)cc1-n1cncn1)Nc1cccc2[nH]c(=O)[nH]c12]

Preparation of 4-(trifluoromethyl)-2-(1H-1,2,4-triazol-1-yl)benzonitrile 14e (scheme 7)

To commercially available 2-chloro-4-trifluoromethylbenzonitrile 13 (1 ml, 7.2 mmol) in DMF 1 equiv. of NaH and 1,2,4-tetrazole (4 equiv., 1.98 g) were added and the mixture was heated at 80° C. overnight. The reaction was evaporated and the residue was dissolved in AcOEt and washed with water and brine. The organic phase was evaporated obtaining 900 mg of a yellow solid. Yield=53% $^1$HNMR (DMSO, 200 MHz) δ 8.08 (1H, dd, J=7.6 Hz, J'=1 Hz), 8.33 (3H, m), 9.29 (1H, s).

Preparation of (4-(trifluoromethyl)-2-(1H-1,2,4-triazol-1-yl)phenyl)-methanamine 2e Benzonitrile 14e (860 mg, 3.6 mmol) dissolved in 5 ml of ether was added dropwise at 0° C. to LiAlH$_4$ (2 equiv., 276 mg) suspended in diethyl ether (20 ml). The mixture was stirred at room temperature for 24 hours. The reaction was quenched by addition of water and filtrated and the salts were washed with ether. The organic phase was separated, anhydrified and evaporated giving 600 mg of a red oil. Yield=70% $^1$HNMR (DMSO, 200 MHz) δ 3.31 (2H, bs), 3.64 (2H, s), 7.85 (3H, m), 8.28 (1H, s), 9.02 (1H, s).

Preparation of 1-(4-(trifluoromethyl)-2-(1H-1,2,4-triazol-1-yl)benzyl)-3-(2,3-dihydro-2-oxo-1H-benzo[d]imidazol-4-yl)urea Amine 2e (600 mg, 2.48 mmol) was dissolved in 20 ml of AcOEt and at 0° C. triphosgene (755 mg, 1 equiv.) was added to the solution. The mixture was warmed at 80° C. for 4 hours then evaporated and the residue was dissolved in 10 ml of DMF. The solution of the isocyanate was added dropwise to a solution in DMF (10 ml) of compound 1a (450 mg, 3 mmol) and the mixture was warmed at 80° C. for 8 hours. (TLC AcOEt 9.5/MeOH 0.5). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 110 mg of an orange solid. Yield=10% $^1$HNMR (DMSO, 200 MHz) δ 4.30 (2H, d, J=6 Hz), 6.64 (1H, dd, J=7.4 Hz, J'=1.2 Hz), 6.79 (2H, m), 6.91 (1H, dd), 7.83 (1H, d), 7.92 (2H, d), 8.33 (1H, bs), 8.42 (1H, bs), 9.07 (1H, bs), 9.94 (1H, bs), 10.59 (1H, bs); [M$^{+1}$] 418.2 ($C_{18}H_{14}F_3N_7O_2$ requires 417.34).

Example 9

1-(4-fluorobenzyl)-3-(2,3-dihydro-2-oxo-1H-benzo[d]imidazol-4-yl)urea (scheme 1)

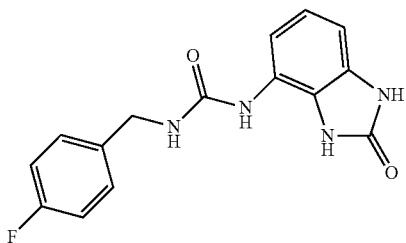 [SMILES: O=C(NCc1ccc(F)cc1)Nc1cccc2[nH]c(=O)[nH]c12]

Preparation of 1-(4-fluorobenzyl)-3-(2,3-dihydro-2-oxo-1H-benzo[d]imidazol-4-yl)urea Commercially available p-fluorobenzylamine (0.76 ml, 6.7 mmol) was dissolved in 40 ml of AcOEt and at 0° C. triphosgene (1.98 g, 1 equiv.) was added to the solution. The mixture was warmed at 80° C. for 4 hours then evaporated and the residue was dissolved in 20 ml of DMF. The solution of the isocyanate was added dropwise to a solution in DMF (10 ml) of compound 1a (900 mg, 6 mmol) and the mixture was warmed at 80° C. for 8 hours. (TLC AcOEt). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 420 mg of a white solid. Yield=23% $^1$HNMR (DMSO, 200 MHz) δ 4.29 (2H, d, J=6 Hz), 6.62 (1H, dd, J=7.6 Hz, J'=1.2 Hz), 6.80 (2H, m), 6.95 (1H, dd, J=8.2 Hz, J'=1.2 Hz), 7.15 (2H, m), 7.35 (2H, m), 8.23 (1H, bs), 9.96 (1H, bs), 10.59 (1H, bs); [M$^{+1}$] 301.1 ($C_{15}H_{13}FN_4O_2$ requires 300.29).

Example 10

1-(4-chlorobenzyl)-3-(2,3-dihydro-2-oxo-1H-benzo[d]imidazol-4-yl)urea (scheme 1)

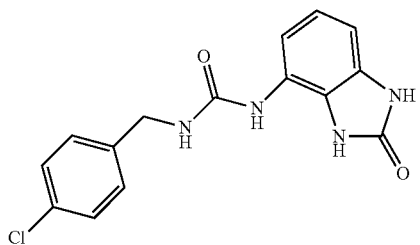 [SMILES: O=C(NCc1ccc(Cl)cc1)Nc1cccc2[nH]c(=O)[nH]c12]

Preparation of 1-(4-chlorobenzyl)-3-(2,3-dihydro-2-oxo-1H-benzo[d]imidazol-4-yl)urea Commercially available p-chlorobenzylamine (846 mg, 6 mmol) was dissolved in 40 ml of AcOEt and at 0° C. triphosgene (1.78 g, 1 equiv.) was added to the solution. The mixture was warmed at 80° C. for 4 hours then evaporated and the residue was dissolved in 20 ml of DMF. The solution of the isocyanate was added dropwise to a solution in DMF (10 ml) of compound 1a (900 mg, 6 mmol) and the mixture was warmed at 80° C. for 8 hours. (TLC AcOEt). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 300 mg of a white solid. Yield=16% $^1$HNMR (DMSO, 200 MHz) δ 4.30 (2H, d, J=6.2 Hz), 6.62 (1H, dd, J=7.6 Hz, J'=1.2 Hz), 6.83 (2H, m), 6.96 (1H, dd, J=8 Hz, J'=1 Hz), 7.35 (4H, m), 8.27 (1H, bs), 9.98 (1H, bs), 10.59 (1H, bs); [M$^{+1}$] 317.1 ($C_{15}H_{13}ClN_4O_2$ requires 316.74).

Example 11

1-(4-chloro-2-(dimethylamino)benzyl)-3-(2,3-dihydro-2-oxo-1H-benzo[d]imidazol-4-yl)urea (scheme 1)

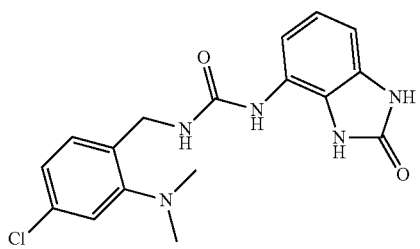 [SMILES: CN(C)c1cc(Cl)ccc1CNC(=O)Nc1cccc2[nH]c(=O)[nH]c12]

Preparation of 4-chloro-2-(dimethylamino)benzonitrile 16af (scheme 8)

To commercially available 2-fluoro-4-chlorobenzonitrile 15a (2 g, 12.8 mmol) dimethylamine (4 equiv., 3.5 ml) was added and the solution was heated in closed vessel at 80° C. overnight. The reaction was evaporated and the residue was dissolved in AcOEt and washed with water and brine. The residue was purified by chromatographic column using EtOAc 1/petroleum ether 9 as eluant obtaining 1.95 g of a transparent oil. Yield=87% $^1$HNMR (DMSO, 200 MHz) δ 3.01 (6H, s), 6.91 (1H, dd, J=8.4 Hz, J'=2 Hz), 7.02 (1H, d, J=2 Hz), 7.60 (1H, d, J=8.4 Hz)

Preparation of 2-(aminomethyl)-5-chloro-N,N-dimethylbenzenamine 2af

Benzonitrile 16af (1.95 g, 10.8 mmol) dissolved in 5 ml of ether was added dropwise at 0° C. to LiAlH$_4$ (2 equiv., 821 mg) suspended in diethyl ether (20 ml). The mixture was stirred at room temperature for 24 hours. The reaction was quenched by addition of water and filtrated and the salts were washed with ether. The organic phase was separated, anhydrified and evaporated giving 2 g of a pale yellow oil. Yield=98% $^1$HNMR (DMSO, 200 MHz) δ 1.72 (2H, bs), 2.61 (6H, s), 3.71 (2H, s), 6.99 (1H, m), 7.05 (1H, d, J=2.2 Hz), 7.46 (1H, d, J=8 Hz)

Preparation of 1-(4-chloro-2-(dimethylamino)benzyl)-3-(2,3-dihydro-2-oxo-1H-benzo[d]imidazol-4-yl)urea Amine 2af (1 g, 5.5 mmol) was dissolved in 20 ml of AcOEt and at 0° C. triphosgene (1.63 g, 1 equiv.) was added to the solution. The mixture was warmed at 80° C. for 4 hours then evaporated and the residue was dissolved in 10 ml of DMF. The solution of the isocyanate was added dropwise to a solution in DMF (10 ml) of compound 1a (820 mg, 5.5 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 550 mg of a white solid. Yield=28% $^1$HNMR (DMSO, 200 MHz) δ 2.64 (6H, s), 4.34 (2H, d, J=5.8 Hz), 6.62 (1H, dd, J=7.2 Hz, J'=1 Hz), 6.73 (1H, t), 6.83 (1H, t, J=7.6 Hz), 6.90 (1H, dd, J=8.2 Hz, J'=1 Hz), 7.06 (2H, m), 7.31 (1H, d, J=8.8 Hz), 8.33 (1H, bs), 9.98 (1H, bs), 10.59 (1H, bs); [M$^{+1}$] 360.7 (C$_{17}$H$_{18}$ClN$_5$O$_2$ requires 359.81).

Example 12

1-(4-chloro-2-(pyrrolidin-1-yl)benzyl)-3-(2,3-dihydro-2-oxo-1H-benzo[d]imidazol-4-yl)urea (scheme 1)

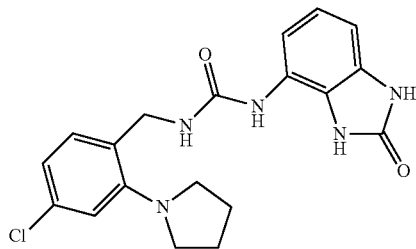 [SMILES: O=C(NCc1ccc(Cl)cc1N1CCCC1)Nc1cccc2[nH]c(=O)[nH]c12]

Preparation of 4-chloro-2-(pyrrolidin-1-yl)benzonitrile 16ag (scheme 8)

To commercially available 2-fluoro-4-chlorobenzonitrile 15a (3 g, 19.3 mmol) pyrrolidine (4 equiv., 6.38 ml) was added and the solution was heated at 80° C. overnight. The reaction was evaporated and the residue was dissolved in AcOEt and washed with water and brine. The residue was purified by crystallization from water obtaining 3.86 g of a pale yellow solid. Yield=97% $^1$HNMR (DMSO, 200 MHz) δ 1.93 (4H, m), 3.51 (4H, m), 6.69 (1H, dd, J=8.4 Hz, J'=1.8 Hz), 6.76 (1H, d, J=2 Hz), 7.49 (1H, d, J=8.4 Hz)

Preparation of (4-chloro-2-(pyrrolidin-1-yl)phenyl)methanamine 2ag

Benzonitrile 16ag (3.8 g, 18.4 mmol) dissolved in 15 ml of ether was added dropwise at 0° C. to LiAlH$_4$ (2 equiv., 1.4 g) suspended in diethyl ether (30 ml). The mixture was stirred at room temperature for 24 hours. The reaction was quenched by addition of water and filtrated and the salts were washed with ether. The organic phase was separated, anhydrified and evaporated giving 4 g of a yellow oil. Yield=98% $^1$HNMR (DMSO, 200 MHz) δ 1.72 (2H, bs), 1.86 (4H, m), 3.14 (4H, m), 3.68 (2H, s), 6.77 (1H, d, J=2 Hz), 6.80 (1H, dd, J=8.2 Hz), 7.36 (1H, d, J=8 Hz)

Preparation of 1-(4-chloro-2-(pyrrolidin-1-yl)benzyl)-3-(2,3-dihydro-2-oxo-1H-benzo[d]imidazol-4-yl)urea Amine 2ag (1 g, 4.76 mmol) was dissolved in 20 ml of AcOEt and at 0° C. triphosgene (1.4 g, 1 equiv.) was added to the solution. The mixture was warmed at 80° C. for 4 hours then evaporated and the residue was dissolved in 10 ml of DMF. The solution of the isocyanate was added dropwise to a solution in DMF (10 ml) of compound 1a (700 mg, 4.9 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 360 mg of a white solid. Yield=19% $^1$HNMR (DMSO, 200 MHz) δ 1.89 (4H, m), 3.17 (4H, m), 4.30 (2H, d, J=5.4 Hz), 6.61 (1H, dd, J=7.6 Hz, J'=1 Hz), 6.69 (1H, t), 6.87 (4H, m), 7.24 (1H, d, J=7.8 Hz), 8.38 (1H, bs), 10.00 (1H, bs), 10.59 (1H, bs); [M$^{+1}$] 386.7 (C$_{19}$H$_{20}$ClN$_5$O$_2$ requires 385.85).

Example 13

1-(4-chloro-2-(piperidin-1-yl)benzyl)-3-(2,3-dihydro-2-oxo-1H-benzo[d]imidazol-4-yl)urea

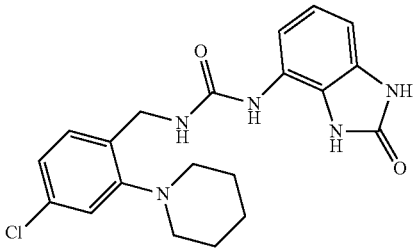 [SMILES: O=C(NCc1ccc(Cl)cc1N1CCCCC1)Nc1cccc2[nH]c(=O)[nH]c12]

Preparation of 4-chloro-2-(piperidin-1-yl)benzonitrile 16ah (scheme 8)

To commercially available 2-fluoro-4-chlorobenzonitrile 15a (2.2 g, 12.87 mmol) piperidine (4 equiv., 5.6 ml) was added and the solution was heated at 80° C. overnight. The reaction was evaporated and to the residue water was added and the solid material was filtrated, washed with water and dried obtaining 3 g of a pale yellow solid. Yield=97% $^1$HNMR (DMSO, 200 MHz) δ 1.54 (2H, m), 1.65 (4H, m), 3.14 (4H, m), 7.09 (1H, dd, J=8.2 Hz, J'=2 Hz), 7.14 (1H, m), 7.69 (1H, d, J=8.4 Hz)

Preparation of (4-chloro-2-(piperidin-1-yl)phenyl)methanamine 2ah

Benzonitrile 16ah (3 g, 13.6 mmol) dissolved in 20 ml of ether was added dropwise at 0° C. to LiAlH$_4$ (2 equiv., 1.03 g) suspended in diethyl ether (30 ml). The mixture was stirred at room temperature for 24 hours. The reaction was quenched by addition of water and filtrated and the salts were washed with ether. The organic phase was separated, anhydrified and evaporated giving 2.92 g of a yellow oil. Yield=96% $^1$HNMR (DMSO, 200 MHz) δ 1.52 (2H, m), 1.61 (4H, m), 2.23 (2H, bs), 2.76 (4H, m), 3.69 (2H, s), 6.97 (1H, d, J=2.2 Hz), 7.04 (1H, dd, J=8.2 Hz, J'=2.2 Hz), 7.46 (1H, d, J=8 Hz)

Preparation of 1-(4-chloro-2-(piperidin-1-yl)benzyl)-3-(2,3-dihydro-2-oxo-1H-benzo[d]imidazol-4-yl)urea Amine 2ah (1.34 g, 6 mmol) was dissolved in 20 ml of AcOEt and at 0° C. triphosgene (1.78 g, 1 equiv.) was added to the solution. The mixture was warmed at 80° C. for 4 hours then evaporated and the residue was dissolved in 10 ml of DMF. The solution of the isocyanate was added dropwise to a solution in DMF (10 ml) of compound 1a (900 mg, 6 mmol) and the mixture was warmed at 80° C. for 8 hours. (TLC AcOEt). The solvent was evaporated and the crude was dissolved in AcOEt (50 ml) and washed with water (1×40 ml) and brine. The organic phase was dried over sodium sulfate and concentrated under vacuum. The purification of the crude residue by chromatographic column gave 750 mg of a white solid. Yield=31% $^1$HNMR (DMSO, 200 MHz) δ 1.58 (2H, m), 1.66 (4H, m), 2.78 (4H, M), 4.32 (2H, d, J=6 Hz), 6.63 (1H, dd), 6.73 (1H, t), 6.94 (1H, t), 6.95 (1H, dd), 7.06 (2H, m), 7.29 (1H, d), 8.35 (1H, bs), 10.05 (1H, bs), 10.60 (1H, bs); [M$^{+1}$] 400.2 (C$_{20}$H$_{22}$ClN$_5$O$_2$ requires 399.87)

Example 14

1-(4-(dimethylamino)benzyl)-3-(2,3-dihydro-2-oxo-1H-benzo[d]imidazol-4-yl)urea (scheme 1)

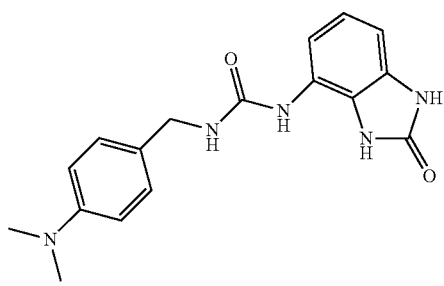 [SMILES: CN(C)c1ccc(CNC(=O)Nc2cccc3[nH]c(=O)[nH]c23)cc1]

Preparation of compound 4-(aminomethyl)-N,N-dimethylbenzenamine 2i (scheme 9)

Commercially available 4-dimethylaminobenzonitrile 18i (2 g, 13.7 mmol) dissolved in 15 ml of ether was added dropwise at 0° C. to LiAlH$_4$ (2 equiv., 1 g) suspended in diethyl ether (40 ml). The mixture was stirred at room temperature for 24 hours. The reaction was quenched by addition of water and filtrated and the salts were washed with ether. The organic phase was separated, anhydrified and evaporated giving 1.85 g of a pale yellow oil. Yield=90% $^1$HNMR (DMSO, 200 MHz) δ 1.60 (2H, bs), 2.84 (6H, s), 3.57 (2H, s), 6.67 (2H, d, J=8.8 Hz), 7.12 (2H, d, J=8.6 Hz)

Preparation of 1-(4-(dimethylamino)benzyl)-3-(2,3-dihydro-2-oxo-1H-benzo[d]imidazol-4-yl)urea 4-(aminomethyl)-N,N-dimethylbenzenamine 2i (1 g, 6.9 mmol) was dissolved in 40 ml of AcOEt and at 0° C. triphosgene (2 g, 1 equiv.) was added to the solution. The mixture was warmed at 80° C. for 4 hours then evaporated and the residue was dissolved in 20 ml of DMF. The solution of the isocyanate was added dropwise to a solution in DMF (10 ml) of compound 1a (1 g, 6.9 mmol) and the mixture was warmed at 80° C. for 8 hours. (TLC AcOEt). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 350 mg of a white solid. Yield=16% $^1$HNMR (DMSO, 200 MHz) δ 2.51 (6H, s), 4.18 (2H, d, J=5.6 Hz), 6.58 (2H, m), 6.69 (2H, d, J=8.8 Hz), 6.86 (2H, m), 7.14 (2H, d, J=8.8 Hz), 8.18 (1H, s), 9.98 (1H, bs), 10.58 (1H, bs); [M$^{+1}$] 326.5 (C$_{17}$H$_{19}$N$_5$O$_2$ requires 325.37).

Example 15

1-(4-(pyrrolidin-1-yl)benzyl)-3-(2,3-dihydro-2-oxo-1H-benzo[d]imidazol-4-yl)urea (scheme 1)

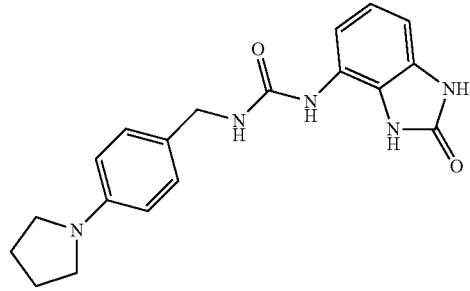 [SMILES: O=C(NCc1ccc(N2CCCC2)cc1)Nc1cccc2[nH]c(=O)[nH]c12]

Preparation of 4-(pyrrolidin-1-yl)benzonitrile 18l (scheme 9)

To commercially available 4-chlorobenzonitrile 17 (5 g, 36 mmol) 12 ml of pyrrolidine were added and the reaction was heated at 100° C. for 24 hours in closed vessel. The reaction was evaporated and the residue was dissolved in AcOEt and washed with water and brine. The purification of the crude residue by chromatographic column using AcOEt 1/Petroleum ether 9 as eluant gave 1.68 g of a pale yellow solid. Yield=33% $^1$HNMR (DMSO, 200 MHz) δ 1.96 (4H, m), 3.28 (4H, m), 6.58 (2H, d, J=9 Hz), 7.51 (2H, d, J=9 Hz)

Preparation of (4-(pyrrolidin-1-yl)phenyl)methanamine 2l

Benzonitrile 18l (1.68 g, 9.76 mmol) dissolved in 10 ml of ether was added drop wise at 0° C. to LiAlH$_4$ (2 equiv., 742 mg) suspended in diethyl ether (40 ml). The mixture was stirred at room temperature for 24 hours. The reaction was quenched by addition of water and filtrated and the salts were washed with ether. The organic phase was separated, anhydrified and evaporated giving 1.48 g of a yellow oil. Yield=86% ¹HNMR (DMSO, 200 MHz) δ 1.60 (2H, bs), 1.93 (4H, m), 3.17 (4H, m), 3.57 (2H, s), 6.46 (2H, d, J=8.6 Hz), 7.09 (2H, d, J=8.4 Hz).

Preparation of 1-(4-(pyrrolidin-1-yl)benzyl)-3-(2,3-dihydro-2-oxo-1H-benzo[d]imidazol-4-yl)urea (4-(pyrrolidin-1-yl)phenyl)methanamine 2l (774 mg, 4.4 mmol) was dissolved in 40 ml of AcOEt and at 0° C. triphosgene (1.3 g, 1 equiv.) was added to the solution. The mixture was warmed at 80° C. for 4 hours then evaporated and the residue was dissolved in 20 ml of DMF. The solution of the isocyanate was added dropwise to a solution in DMF (10 ml) of compound 1a (660 mg, 4.4 mmol) and the mixture was warmed at 80° C. for 8 hours. (TLC AcOEt 9.5/MeOH 0.5). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 250 mg of a white solid. Yield=16% ¹HNMR (DMSO, 200 MHz) δ 1.92 (4H, m), 3.17 (4H, m), 4.17 (2H, d, J=5.6 Hz), 6.58 (4H, m), 6.84 (2H, m), 7.12 (2H, d, J=8.6 Hz), 8.16 (1H, bs), 9.93 (1H, bs), 10.58 (1H, bs); [M⁺¹] 352.3 ($C_{19}H_{21}N_5O_2$ requires 351.4).

Example 16

1-(4-(piperidin-1-yl)benzyl)-3-(2,3-dihydro-2-oxo-1H-benzo[d]imidazol-4-yl)urea (scheme 1)

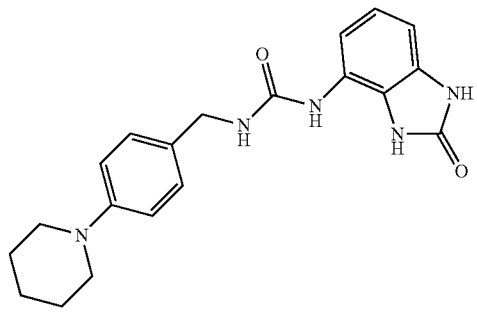 [SMILES: O=C(NCc1ccc(N2CCCCC2)cc1)Nc1cccc2[nH]c(=O)[nH]c12]

Preparation of 4-(piperidin-1-yl)benzonitrile 18m (scheme 9)

To commercially available 4-chlorobenzonitrile 17 (1 g, 7.26 mmol) 3 ml of piperidine were added and the reaction was heated at 100° C. for 72 hours in closed vessel. The reaction was evaporated and the residue was dissolved in AcOEt and washed with water and brine. The purification of the crude residue by chromatographic column using AcOEt 1/Petroleum ether 9 as eluant gave 1.2 g of a pale yellow oil. Yield=89% ¹HNMR (DMSO, 200 MHz) δ 1.57 (6H, m), 3.34 (4H, m), 6.98 (2H, d, J=9 Hz), 7.53 (2H, d, J=9 Hz)

Preparation of (4-(piperidin-1-yl)phenyl)methanamine 2m

Benzonitrile 18m (1.2 g, 6.48 mmol) dissolved in 10 ml of ether was added dropwise at 0° C. to LiAlH₄ (2 equiv., 493 mg) suspended in diethyl ether (40 ml). The mixture was stirred at room temperature for 24 hours. The reaction was quenched by addition of water and filtrated and the salts were washed with ether. The organic phase was separated, anhydrified and evaporated giving 1 g of an orange oil. Yield=82%. ¹HNMR (DMSO, 200 MHz) δ 1.57 (6H, m), 3.06 (4H, m), 3.58 (2H, s), 6.84 (2H, d, J=8.6 Hz), 7.13 (2H, d, J=8.4 Hz), 7.33 (2H, bs).

Preparation of 1-(4-(piperidin-1-yl)benzyl)-3-(2,3-dihydro-2-oxo-1H-benzo[d]imidazol-4-yl)urea (4-(piperidin-1-yl)phenyl)methanamine 2m (1.47 g, 7.8 mmol) was dissolved in 40 ml of AcOEt and at 0° C. triphosgene (2.3 g, 1 equiv.) was added to the solution. The mixture was warmed at 80° C. for 4 hours then evaporated and the residue was dissolved in 20 ml of DMF. The solution of the isocyanate was added dropwise to a solution in DMF (10 ml) of compound 1a (1.15 g, 7.8 mmol) and the mixture was warmed at 80° C. for 8 hours. (TLC AcOEt). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 520 mg of a pale yellow solid. Yield=18% ¹HNMR (DMSO, 200 MHz) δ 1.58 (6H, m), 3.08 (4H, m), 4.19 (2H, d, J=6 Hz), 6.62 (2H, m), 6.86 (4H, m), 7.15 (2H, d, J=8.8 Hz), 8.19 (1H, bs), 9.95 (1H, bs), 10.58 (1H, bs); [M⁺¹] 366.3 ($C_{20}H_{23}N_5O_2$ requires 365.43).

Example 17

1-(4-methylbenzyl)-3-(2,3-dihydro-2-oxo-1H-benzo[d]imidazol-4-yl)urea (scheme 1)

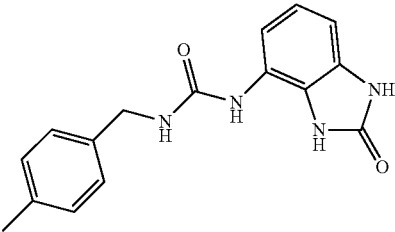 [SMILES: Cc1ccc(CNC(=O)Nc2cccc3[nH]c(=O)[nH]c23)cc1]

Preparation of 1-(4-methylbenzyl)-3-(2,3-dihydro-2-oxo-1H-benzo[d]imidazol-4-yl)urea Commercially available p-methylbenzylamine (0.88 ml, 6.97 mmol) was dissolved in 40 ml of AcOEt and at 0° C. triphosgene (2 g, 1 equiv.) was added to the solution. The mixture was warmed at 80° C. for 4 hours then evaporated and the residue was dissolved in 20 ml of DMF. The solution of the isocyanate was added drop wise to a solution in DMF (10 ml) of compound 1a (1 g, 6.97 mmol) and the mixture was warmed at 80° C. for 8 hours. (TLC AcOEt). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 350 mg of a white solid. Yield=17% ¹HNMR (DMSO, 200 MHz) δ 6.61 (1H, dd, J=7.6 Hz, J'=1.2 Hz), 6.70 (1H, t), 6.83 (1H, t, J=8 Hz), 6.92 (1H, dd, J=8 Hz, J'=1 Hz), 7.17 (4H, dd, J=15.6 Hz, J'=8.2 Hz), 8.22 (1H, bs), 9.96 (1H, bs), 10.58 (1H, bs); [M$^{+1}$] 297.1 (C$_{16}$H$_{16}$N$_4$O$_2$ requires 296.32).

Example 18

1-(2-(dimethylamino)-4-methylbenzyl)-3-(2,3-dihydro-2-oxo-1H-benzo[d]imidazol-4-yl)urea (scheme 1) ù

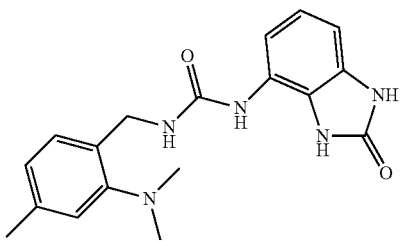 [SMILES: Cc1ccc(CNC(=O)Nc2cccc3[nH]c(=O)[nH]c23)c(N(C)C)c1]

Preparation of 4-methyl-2-dimethylaminobenzonitrile 16bf (scheme 8)

To commercially available 2-fluoro-4-methylbenzonitrile 15b (2.5 g, 18.5 mmol) was added dimethylamine (4 equiv., 4.8 ml) and the solution was heated at 80° C. overnight. The reaction was evaporated and the residue was dissolved in AcOEt and washed with water and brine. The organic phase was evaporated obtaining 2.96 g of a yellow oil. Yield=99% $^1$HNMR (DMSO, 200 MHz) δ 2.31 (3H, s), 2.93 (6H, s), 6.74 (1H, dd, J=8 Hz, J'=0.8 Hz), 6.85 (1H, s), 7.47 (1H, d, J=8 Hz)

Preparation of (4-methyl-2-dimethylaminophenyl)methanamine 2bf

Benzonitrile 16bf (2.9 g, 18.1 mmol) dissolved in 25 ml of ether was added dropwise at 0° C. to LiAlH$_4$ (2 equiv., 1.38 g) suspended in diethyl ether (40 ml). The mixture was stirred at room temperature for 24 hours. The reaction was quenched by addition of water and filtrated and the salts were washed with ether. The organic phase was separated, anhydrified and evaporated giving 2.35 g of an oil. Yield=80% $^1$HNMR (DMSO, 200 MHz) δ 2.65 (2H, bs), 2.25 (3H, s), 2.60 (6H, s), 3.70 (2H, s), 6.80 (2H, m), 7.27 (1H, d, J=7.4 Hz)

Preparation 1-(2-(dimethylamino)-4-methylbenzyl)-3-(2,3-dihydro-2-oxo-1H-benzo[d]imidazol-4-yl)urea Amine 2bf (1.1 g, 6.7 mmol) was dissolved in 40 ml of AcOEt and at 0° C. triphosgene (1.93 g, 6.7 mmol) was added to the solution. The mixture was warmed at 80° C. for 4 hours then evaporated and the residue was dissolved in 15 ml of DMF. The solution of the isocyanate was added dropwise to a solution in DMF (10 ml) of compound 1a (1 g, 6.7 mmol) and the mixture was warmed at 80° C. for 8 hours. (TLC AcOEt 9.5/MeOH 0.5). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 450 mg of a pale yellow solid. Yield=19% $^1$HNMR (DMSO, 200 MHz) δ 2.26 (3H, s), 2.59 (6H, m), 4.33 (2H, d, J=5.6 Hz), 6.60 (2H, m), 6.87 (4H, m), 7.18 (1H, d, J=7.6 Hz), 8.28 (1H, s), 9.96 (1H, bs), 10.60 (1H, bs); [M$^{+1}$] 339.56 (C$_{18}$H$_{21}$N$_5$O$_2$ requires 339.39).

Example 19

1-(4-methyl-2-(piperidin-1-yl)benzyl)-3-(2,3-dihydro-2-oxo-1H-benzo[d]imidazol-4-yl)urea (scheme 1)

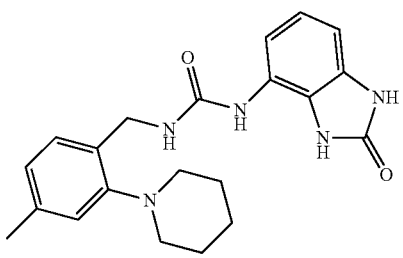 [SMILES: Cc1ccc(CNC(=O)Nc2cccc3[nH]c(=O)[nH]c23)c(N2CCCCC2)c1]

Preparation of 4-(methyl)-2-(piperidin-1-yl)benzonitrile 16bh (scheme 8)

To commercially available 2-fluoro-4-methylbenzonitrile 15b (2.5 g, 18.5 mmol) was added piperidine (4 equiv., 7.3 ml) and the solution was heated at 80° C. overnight. The reaction was evaporated and the residue was dissolved in AcOEt and washed with water and brine. The organic phase was evaporated obtaining 2.3 g of a white solid. Yield=65% $^1$HNMR (DMSO, 200 MHz) δ 1.62 (6H, m), 2.32 (3H, s), 3.07 (4H, m), 6.87 (1H, dd, J=7.8 Hz, J'=0.8 Hz), 6.95 (1H, s), 7.53 (1H, d, J=7.8 Hz)

Preparation of (4-(methyl)-2-(piperidin-1-yl)phenyl)methanamine 2bh

Benzonitrile 16bh (2.3 g, 11.5 mmol) dissolved in 15 ml of ether was added dropwise at 0° C. to LiAlH$_4$ (2 equiv., 873 mg) suspended in diethyl ether (40 ml). The mixture was stirred at room temperature for 24 hours. The reaction was quenched by addition of water and filtrated and the salts were washed with ether. The organic phase was separated, anhydrified and evaporated giving 2.25 g of an oil. Yield=96% $^1$HNMR (DMSO, 200 MHz) δ 1.59 (6H, m), 2.24 (3H, s), 2.76 (4H, m), 3.67 (2H, s), 6.80 (2H, m), 7.27 (1H, d, J=8.4 Hz)

Preparation of 1-(4-methyl-2-(piperidin-1-yl)benzyl)-3-(2,3-dihydro-2-oxo-1H-benzo[d]imidazol-4-yl)urea Amine 2bh (1.1 g, 5.4 mmol) was dissolved in 40 ml of AcOEt and at 0° C. triphosgene (1.56 g, 5.4 mmol) was added to the solution. The mixture was warmed at 80° C. for 4 hours then evaporated and the residue was dissolved in 15 ml of DMF. The solution of the isocyanate was added dropwise to a solution in DMF (10 ml) of compound 1a (1 g, 6.7 mmol) and the mixture was warmed at 80° C. for 8 hours. (TLC AcOEt 9.5/MeOH 0.5). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 450 mg of a white solid. Yield=22% $^1$HNMR (DMSO, 200 MHz) δ 1.58 (6H, m), 2.78 (4H, m), 4.34 (2H, d, J=5.8 Hz), 6.59 (2H, m), 6.90 (4H, m), 7.18 (1H, d, J=7.6 Hz), 8.26 (1H, s), 10.01 (1H, bs), 10.60 (1H, bs); [M$^{+1}$] 379.51 (C$_{21}$H$_{25}$N$_5$O$_2$ requires 379.46).

Example 20

1-(2,3-dihydro-2-oxo-1H-benzo[d]imidazol-4-yl)-3-((pyridin-4-yl)methyl)urea (scheme 1)

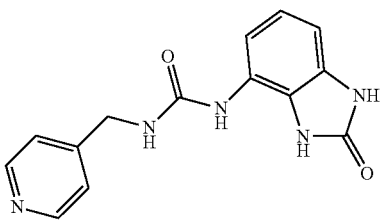 [SMILES: O=C(NCc1ccncc1)Nc1cccc2[nH]c(=O)[nH]c12]

Preparation of 1-(2,3-dihydro-2-oxo-1H-benzo[d]imidazol-4-yl)-3-((pyridin-4-yl)methyl)urea Commercially available 4-aminomethylpyridine (2 g, 20.8 mmol) was dissolved in 60 ml of AcOEt and at 0° C. triphosgene (5.8 g, 21 mmol) was added to the solution. The mixture was warmed at 80° C. for 4 hours then evaporated and the residue was dissolved in 20 ml of DMF. The solution of the isocyanate was added dropwise to a solution in DMF (10 ml) of compound 1a (3.16 g, 21 mmol) and the mixture was warmed at 80° C. for 8 hours. (TLC AcOEt 9.5/MeOH 0.5). The solvent was evaporated and the crude was dissolved in AcOEt (80 ml) and washed with water (1×40 ml) and brine. The organic phase was dried over sodium sulfate and concentrated under vacuum. The purification of the crude residue by chromatographic column gave 640 mg of a white solid. Yield=11% $^1$HNMR (DMSO, 200 MHz) δ 4.34 (2H, d, J=5.8 Hz), 6.62 (1H, dd, J=7.6 Hz, J'=1 Hz), 6.92 (3H, m), 7.31 (2H, dd, J=4.4 Hz, J'=1.4 Hz), 8.49 (3H, m), 10.03 (1H, bs), 10.59 (1H, bs); [M$^{+1}$] 284.1 (C$_{14}$H$_{13}$N$_5$O$_2$ requires 283.29).

Example 21

1-((6-chloropyridin-3-yl)methyl)-3-(2,3-dihydro-2-oxo-1H-benzo[d]imidazol-4-yl)urea (scheme 1)

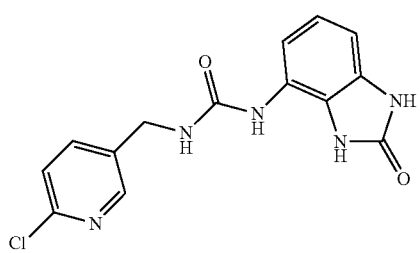 [SMILES: O=C(NCc1ccc(Cl)nc1)Nc1cccc2[nH]c(=O)[nH]c12]

Preparation of 1-(((6-chloropyridin-3-yl)methyl-3-(2,3-dihydro-2-oxo-1H-benzo[d]imidazol-4-yl)urea Commercially available (6-chloropyridin-3-yl)methanamine (1 g, 7 mmol) was dissolved in 40 ml of AcOEt and at 0° C. triphosgene (1.93 g, 7 mmol) was added to the solution. The mixture was warmed at 80° C. for 4 hours then evaporated and the residue was dissolved in 10 ml of DMF. The solution of the isocyanate was added dropwise to a solution in DMF (10 ml) of compound 1a (1 g, 6.7 mmol) and the mixture was warmed at 80° C. for 8 hours. (TLC AcOEt 9.5/MeOH 0.5). The solvent was evaporated and the crude was dissolved in AcOEt (80 ml) and washed with water (1×40 ml) and brine. The organic phase was dried over sodium sulfate and concentrated under vacuum. The purification of the crude residue by chromatographic column gave 450 mg of a pale yellow solid. Yield=21% $^1$HNMR (DMSO, 200 MHz) δ 4.32 (2H, d, J=5.8 Hz), 6.62 (1H, d, J=7.2 Hz), 6.85 (3H, m), 7.48 (1H, d, J=8.4 Hz), 7.81 (1H, dd, J=8.2 Hz, J'=2.4 Hz), 8.33 (2H, m), 10.02 (1H, bs), 10.60 (1H, bs); [M$^{+1}$] 317.8 (C$_{14}$H$_{12}$ClN$_5$O$_2$ requires 317.73).

Example 22

1-(4-chloro-2-(3-hydroxypyrrolidin-1-yl)benzyl)-3-(2,3-dihydro-2-oxo-1H-benzo[d]imidazol-4-yl)urea (scheme 1)

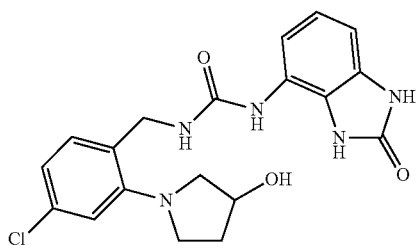 [SMILES: O=C(NCc1ccc(Cl)cc1N1CCC(O)C1)Nc1cccc2[nH]c(=O)[nH]c12]

Preparation of 4-chloro-2-(3-hydroxypyrrolidin-1-yl)benzonitrile 16ai (scheme 8)

To commercially available 2-fluoro-4-chlorobenzonitrile 15a (1 g, 6.4 mmol) was added 3-pyrrolidin 1-ol (2 equiv., 1 g) and the solution was heated at 80° C. overnight. The reaction was evaporated and the residue was dissolved in AcOEt and washed with water and brine. The organic phase was evaporated obtaining 1.2 g of a white solid. Yield=85% $^1$HNMR (DMSO, 200 MHz) δ 1.91 (2H, m), 3.54 (4H, m), 4.37 (1H, b), 5.06 (1H, bd, J=3.4 Hz), 6.72 (2H, m), 7.50 (1H, d, J=8.2 Hz)

Preparation of 1-(2-(aminomethyl)-5-chlorophenyl)pyrrolidin-3-ol 2ai

Benzonitrile 16ai (1.2 g, 5.4 mmol) dissolved in 15 ml of ether was added dropwise at 0° C. to LiAlH$_4$ (2 equiv., 410 mg) suspended in diethyl ether (40 ml). The mixture was stirred at room temperature for 24 hours. The reaction was quenched by addition of water and filtrated and the salts were washed with ether. The organic phase was separated, anhydrified and evaporated giving 1.18 g of an oil. Yield=96% $^1$HNMR (DMSO, 200 MHz) δ 1.90 (2H, m), 3.34 (4H, m), 3.67 (2H, s), 4.27 (1H, b), 4.90 (1H, b), 6.76 (2H, m), 7.34 (1H, d, J=8 Hz)

Preparation of 1-(4-chloro-2-(3-hydroxypyrrolidin-1-yl)benzyl)-3-(2,3-dihydro-2-oxo-1H-benzo[d]imidazol-4-yl)urea 1-(2-(aminomethyl)-5-chlorophenyl)pyrrolidin-3-ol 2ai (1.18 g, 5.2 mmol) was dissolved in 40 ml of AcOEt and at 0° C. triphosgene (1.4 g, 5.2 mmol) was added to the solution.

The mixture was warmed at 80° C. for 4 hours then evaporated and the residue was dissolved in 10 ml of DMF. The solution of the isocyanate was added dropwise to a solution in DMF (10 ml) of compound 1a (674 mg, 4.52 mmol) and the mixture was warmed at 80° C. for 8 hours. (TLC AcOEt 8/MeOH 2). The solvent was evaporated and the crude was dissolved in AcOEt (80 ml) and washed with water (1×40 ml) and brine. The organic phase was dried over sodium sulfate and concentrated under vacuum. The purification of the crude residue by chromatographic column gave 390 mg of a pale pink solid. Yield=21% $^1$HNMR (DMSO, 200 MHz) δ 2.20 (2H, m), 3.33 (4H, m), 3.69 (2H, s), 4.29 (1H, b), 5.20 (1H, b), 6.62 (2H, m), 6.90 (4H, m), 7.27 (1H, d, J=8 Hz), 8.29 (1H, s), 9.95 (1H, bs), 10.60 (1H, bs); [M$^{+1}$] 402.4 ($C_{19}H_{20}ClN_5O_3$ requires 401.85).

Example 23

1-(5-(trifluoromethyl-furan-2-yl)-methyl)-3-(2,3-dihydro-2-oxo-1H-benzo[d]imidazol-4-yl)urea (scheme 1)

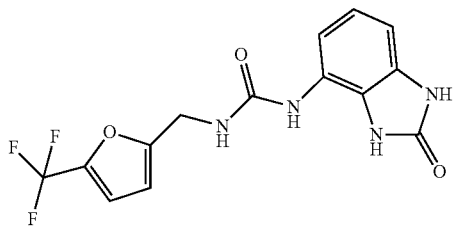 [SMILES: O=C(NCc1ccc(C(F)(F)F)o1)Nc1cccc2[nH]c(=O)[nH]c12]

Preparation of 1-(5-(trifluoromethyl-furan-2-yl)-methyl)-3-(2,3-dihydro-2-oxo-1H-benzo[d]imidazol-4-yl)urea a) Procedure Using Triphosgene Commercially available 2-(aminomethyl)-5-(trifluoromethyl)furan (1 ml, 7.7 mmol) was dissolved in 20 ml of AcOEt and at 0° C. triphosgene (2.20 g, 7.7 mmol) was added to the solution. The mixture was warmed at 80° C. for 4 hours then evaporated and the residue was dissolved in 5 ml of DMF. The solution of the isocyanate was added drop wise to a solution in DMF (5 ml) of compound 1a (720 mg, 4.8 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 780 mg of a white solid. Yield=29% $^1$HNMR (DMSO, 400 MHz) δ 4.38 (2H, d, J=6 Hz), 6.51 (d, 1H, J=2), 6.64 (d, 1H), 6.85 (m, 2H), 6.87 (m, 1H), 7.15 (m, 1H), 8.30 (s, 1H), 9.97 (s, 1H), 10.60 (s, 1H); [M$^{+1}$] 340.5 ($C_{14}H_{11}F_4N_4O_3$ requires 340.26).

b) Procedure Using CDI

To a solution of 2-aminomethyl-5-trifluoromethylfurane (1 g, 6.1 mmol) in THF (30 mL) was added CDI (2.1 mol eq) and the mixture was heated at 70° C. overnight. The reaction mixture was evaporated, water was added and the aqueous phase was extracted with EtOAc (3×20 mL). The recombined organic phases were anhydrified over $Na_2SO_4$ and evaporated at reduced pressure. The oil obtained (1.6 g, 5.9 mmol) was dissolved in DMF (30 mL) and the bicyclic amine 1a was added (0.8 mol eq), then the mixture obtained was heated at 100° C. overnight. The solvent was removed at reduced pressure and the residue was purified by crystallization from a mixture of MeOH/EtOAc to obtain the title compound as white solid (0.78 g, 2.3 mmol, 30% Yield). $^1$HNMR (DMSO, 200 MHz) δ 4.38 (d, 2H, J=6); 6.49 (d, 1H, J=4), 6.51 (dd, 1H), 6.85 (m, 2H), 6.94 (dd, 1H), 7.16 (m, 1H), 8.03 (s, 1H), 9.97 (bs, 1H), 10.60 (bs, 1H). [M$^{+1}$] 340.26 ($C_{14}H_{11}F_3N_4O_3$ requires 340.21).

Example 24

1-(4-(trifluoromethyl)benzyl)-3-(2,3-dihydro-2-oxobenzo[d]oxazol-4-yl)urea (scheme 1)

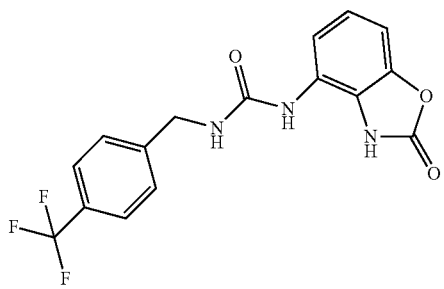 [SMILES: O=C(NCc1ccc(C(F)(F)F)cc1)Nc1cccc2oc(=O)[nH]c12]

Preparation of 4-nitrobenzo[d]oxazol-2(3H)-one 4b (scheme 2)

To 2-amino-3-nitrophenol 3b (2 g, 13.00 mmol) dissolved in THF (50 ml) was added in one portion DCI (1.5 equiv., 19.6 mmol, 3.176 g) and the reaction was refluxed for 4 hours. (TLC AcOEt 1/petroleum ether 1). The reaction was evaporated and the crude material was dissolved in HCL 2N and extracted 3 times with chloroform. The combined organic phases were washed with water, brine, dried over sodium sulfate and concentrated under vacuum. The crude solid was crystallized from ether giving 1.5 g of a beige solid. Yield=65% $^1$HNMR (DMSO, 200 MHz) δ 7.27 (1H, t, J=7.8 Hz), 7.72 (1H, dd, J=8.2 Hz, J'=1 Hz), 7.93 (1H, dd, J=8.4 Hz, J'=0.6 Hz), 12.64 (1H, bs)

Preparation of 4-aminobenzo[d]oxazol-2(3H)-one 1b (scheme 2)

To compound 4b (1 g, 5.72 mmol) dissolved in a mixture of 4/1 MeOH/THF (50 ml) C/Pd 10% (250 mg) was added and the reaction was hydrogenated at 60 psi overnight. (TLC AcOEt) The reaction was filtrated through a pad of Celite and the filtrate was evaporated under vacuum. The crude solid was crystallized from ether giving 476 mg of a white solid. Yield=55.5%. $^1$HNMR (DMSO, 200 MHz) δ 5.07 (2H, bs), 6.47 (2H, m), 6.79 (1H, t, J=8 Hz), 10.93 (1H, bs)

Preparation of 1-(4-(trifluoromethyl)benzyl)-3-(2,3-dihydro-2-oxobenzo[d]oxazol-4-yl)urea Commercially available 4-trifluoromethylbenzylamine (0.5 ml, 3.5 mmol) was dissolved in 20 ml of AcOEt and at 0° C. triphosgene (1 g, 3.5 mmol) was added to the solution. The mixture was warmed at 80° C. for 4 hours then evaporated and the residue was dissolved in 5 ml of DMF. The solution of the isocyanate was added dropwise to a solution in DMF (5 ml) of compound 1b (350 mg, 2.33 mmol) and the mixture was warmed at 80° C. for 8 hours. (TLC AcOEt 9.5/MeOH 0.5). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 200 mg of a white solid. Yield=24% $^1$HNMR (DMSO, 400 MHz) δ 4.41 (2H, d, J=6 Hz), 6.98 (3H, m), 7.05 (1H, m), 7.55 (2H, d), 7.70 (2H, d, J=8 Hz), 8.49 (1H, bs), 11.00 (1H, bs); [M$^{+1}$] 352.1 ($C_{16}H_{12}F_3N_3O_3$ requires 351.28).

Example 25

1-(2-fluoro-4-(trifluoromethyl)benzyl)-3-(2,3-dihydro-2-oxobenzo[d]oxazol-4-yl)urea (scheme 1)

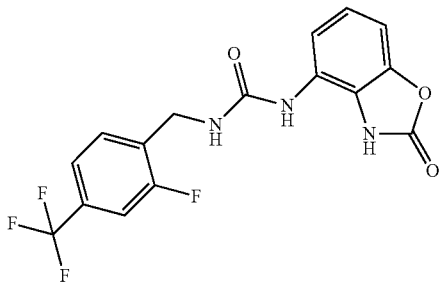 [SMILES: O=C(NCc1ccc(C(F)(F)F)cc1F)Nc1cccc2oc(=O)[nH]c12]

Preparation of 1-(2-fluoro-4-(trifluoromethyl)benzyl)-3-(2,3-dihydro-2-oxobenzo[d]oxazol-4-yl)urea Commercially available 2-fluoro-4-trifluoromethylbenzylamine (0.5 ml, 3.7 mmol) was dissolved in 20 ml of AcOEt and at 0° C. triphosgene (1.12 g, 3.7 mmol) was added to the solution. The mixture was warmed at 80° C. for 4 hours then evaporated and the residue was dissolved in 5 ml of DMF. The solution of the isocyanate was added drop wise to a solution in DMF (5 ml) of compound 1b (360 mg, 2.4 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 100 mg of a white solid. Yield=11% $^1$HNMR (DMSO, 400 MHz) δ 4.43 (2H, d, J=6 Hz), 6.99 (3H, m), 7.05 (1H, m), 7.62 (3H, m), 8.53 (1H, bs), 10.98 (1H, bs); [M$^{+1}$] 370.1 ($C_{16}H_{11}F_4N_3O_3$ requires 369.27).

Example 26

1-(2-chloro-4-(trifluoromethyl)benzyl)-3-(2,3-dihydro-2-oxobenzo[d]oxazol-4-yl)urea (scheme 1)

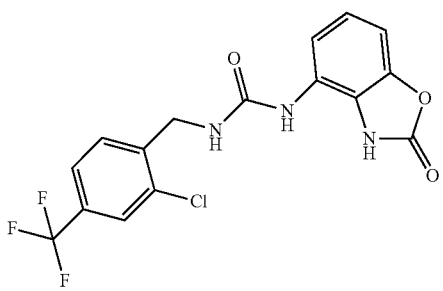 [SMILES: O=C(NCc1ccc(C(F)(F)F)cc1Cl)Nc1cccc2oc(=O)[nH]c12]

Preparation of 1-(2-chloro-4-(trifluoromethyl)benzyl)-3-(2,3-dihydro-2-oxobenzo[d]oxazol-4-yl)urea Commercially available 2-chloro-4-trifluoromethylbenzylamine (572 mg, 2.7 mmol) was dissolved in 20 ml of AcOEt and at 0° C. triphosgene (809 mg, 2.7 mmol) was added to the solution. The mixture was warmed at 80° C. for 4 hours then evaporated and dissolved in 5 ml of DMF. The solution of the isocyanate was added dropwise to a solution in DMF (5 ml) of compound 1b (270 mg, 1.8 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 70 mg of a white solid. Yield=10% $^1$HNMR (DMSO, 400 MHz) δ 4.45 (2H, d, J=6 Hz), 6.97 (2H, d, J=4.4 Hz), 7.07 (2H, m), 7.63 (1H, d, J=8 Hz), 7.74 (2H, d), 7.86 (1H, s), 8.61 (1H, bs), 10.90 (1H, bs); [M$^{+1}$] 386.6 ($C_{16}H_{11}ClF_3N_3O_3$ requires 385.7).

Example 27

1-(4-fluoro-2-(trifluoromethyl)benzyl)-3-(2,3-dihydro-2-oxobenzo[d]oxazol-4-yl)urea (scheme 1)

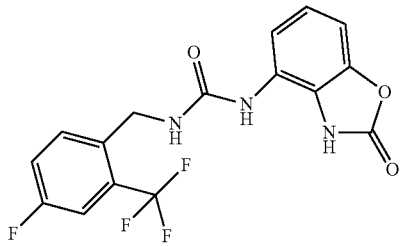 [SMILES: O=C(NCc1ccc(F)cc1C(F)(F)F)Nc1cccc2oc(=O)[nH]c12]

Preparation of 1-(4-fluoro-2-(trifluoromethyl)benzyl)-3-(2,3-dihydro-2-oxobenzo[d]oxazol-4-yl)urea Commercially available 4-fluoro-2-trifluoromethylbenzylamine (0.5 ml, 3.7 mmol) was dissolved in 20 ml of AcOEt and at 0° C. triphosgene (1.12 g, 3.7 mmol) was added to the solution. The mixture was warmed at 80° C. for 4 hours then evaporated and the residue was dissolved in 5 ml of DMF. The solution of the isocyanate was added dropwise to a solution in DMF (5 ml) of compound 1b (360 mg, 2.4 mmol) and the mixture was warmed at 80° C. for 8 hours. (TLC AcOEt 4/petroleum ether 6). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 90 mg of a white solid. Yield=10% $^1$HNMR (DMSO, 200 MHz) δ 4.36 (2H, d, J=5.6 Hz), 6.71 (1H, t, J=6 Hz), 6.98 (2H, m), 7.56 (4H, m), 8.55 (1H, bs), 11.09 (1H, bs); [M$^{+1}$] 370.2 ($C_{16}H_{11}F_4N_3O_3$ requires 369.27).

Example 28

1-(4-chloro-2-(trifluoromethyl)benzyl)-3-(2,3-dihydro-2-oxobenzo[d]oxazol-4-yl)urea scheme 1)

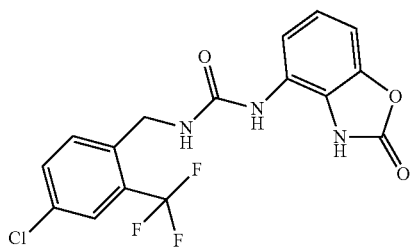 [SMILES: O=C(NCc1ccc(Cl)cc1C(F)(F)F)Nc1cccc2oc(=O)[nH]c12]

Preparation of 1-(4-chloro-2-(trifluoromethyl)benzyl)-3-(2,3-dihydro-2-oxobenzo[d]oxazol-4-yl)urea Commercially available 4-chloro-2-trifluoromethylbenzylamine (1 g, 4.77 mmol) was dissolved in 20 ml of AcOEt and at 0° C. triphosgene (1.41 g, 4.77 mmol) was added to the solution. The mixture was warmed at 80° C. for 4 hours then evaporated and the residue was dissolved in 5 ml of DMF. The solution of the isocyanate was added dropwise to a solution in DMF (5 ml) of compound 1b (475 mg, 3.2 mmol) and the mixture was warmed at 80° C. for 8 hours. (TLC AcOEt 4/petroleum ether 6). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 120 mg of a white solid. Yield=9.7% $^1$HNMR (DMSO, 200 MHz) δ 4.45 (2H, d, J=5.6 Hz), 6.99 (4H, m), 7.65 (1H, d), 7.73 (1H, d), 7.85 (1H, bs), 8.62 (1H, bs), 11.04 (1H, bs); [M$^{+1}$] 386.6 ($C_{16}H_{11}ClF_3N_3O_3$ requires 385.73).

Example 29

1-(2-(dimethylamino)-4-(trifluoromethyl)benzyl)-3-(2,3-dihydro-2-oxobenzo[d]oxazol-4-yl)urea scheme 1)

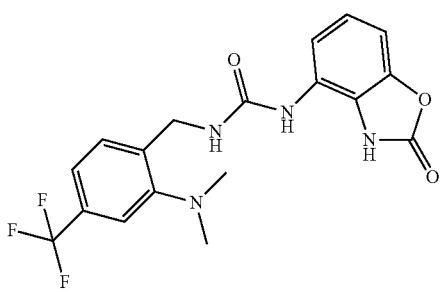 [SMILES: CN(C)c1cc(C(F)(F)F)ccc1CNC(=O)Nc1cccc2oc(=O)[nH]c12]

Preparation of 1-(2-(dimethylamino)-4-(trifluoromethyl)benzyl)-3-(2,3-dihydro-2-oxobenzo[d]oxazol-4-yl)urea Amine 2a (1.2 g, 5.5 mmol) (Scheme 7) was dissolved in 40 ml of AcOEt and at 0° C. triphosgene (1.63 g, 5.5 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1b (820 mg, 5.5 mmol) and the mixture was warmed at 80° C. for 8 hours. (TLC AcOEt 7/petroleum ether 3). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 300 mg of a white solid. Yield=14% $^1$HNMR (DMSO, 200 MHz) δ 2.51 (6H, s), 4.71 (2H, d, J=5.6 Hz), 6.55 (2H, d, J=8.2 Hz), 7.05 (1H, t, J=7.6 Hz), 7.40 (1H, m), 7.51 (1H, d), 10.06 (1H, bt), 11.53 (1H, bs), 11.80 (1H, bs); [M$^{+1}$] 395.1 ($C_{18}H_{17}F_3N_4O_3$ requires 394.35).

Example 30

1-(4-(trifluoromethyl)-2-(pyrrolidin-1-yl)benzyl)-3-(2,3-dihydro-2-oxobenzo[d]oxazol-4-yl)urea (scheme 1)

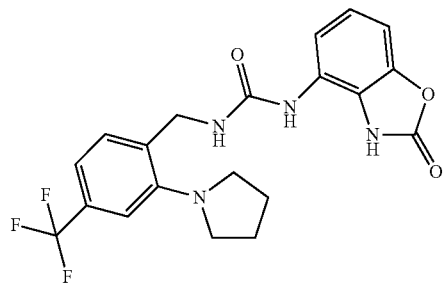 [SMILES: O=C(NCc1ccc(C(F)(F)F)cc1N1CCCC1)Nc1cccc2oc(=O)[nH]c12]

Preparation of 1-(4-(trifluoromethyl)-2-(pyrrolidin-1-yl)benzyl)-3-(2,3-dihydro-2-oxobenzo[d]oxazol-4-yl)urea Amine 2b (289 mg, 1.2 mmol) (Scheme 7) was dissolved in 20 ml of AcOEt and at 0° C. triphosgene (356 mg, 1.2 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1b (180 mg, 1.2 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 100 mg of a white solid. Yield=20% $^1$HNMR (DMSO, 200 MHz) δ 1.94 (4H, m), 3.23 (4H, m), 4.67 (2H, d, J=5.6 Hz), 6.55 (2H, dd, J=8.8 Hz, J'=1.2 Hz), 7.05 (1H, t, J=8.2 Hz), 7.17 (2H, d, J=7.2 Hz), 7.46 (1H, d), 9.98 (1H, t), 11.53 (1H, bs), 11.80 (1H, bs); [M$^{+1}$] 421.2 ($C_{20}H_{19}F_3N_4O_3$ requires 420.39).

Example 31

1-(4-(trifluoromethyl)-2-(piperidin-1-yl)benzyl)-3-(2,3-dihydro-2-oxobenzo[d]oxazol-4-yl)urea (scheme 1)

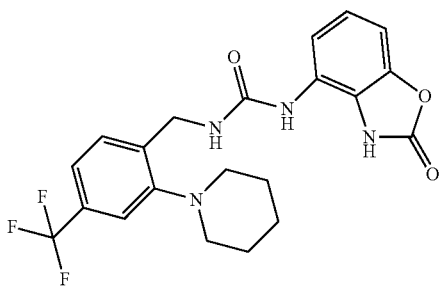 [SMILES: O=C(NCc1ccc(C(F)(F)F)cc1N1CCCCC1)Nc1cccc2oc(=O)[nH]c12]

Preparation of 1-(4-(trifluoromethyl)-2-(piperidin-1-yl)benzyl)-3-(2,3-dihydro-2-oxobenzo[d]oxazol-4-yl)urea Amine 2c (350 mg, 1.33 mmol) (Scheme 7) was dissolved in 20 ml of AcOEt and at 0° C. triphosgene (395 mg, 1.33 mmol) was added to the solution. The mixture was warmed at 80° C. for 4 hours then evaporated and dissolved in 5 ml of DMF. The solution of the isocyanate was added dropwise to a solution in DMF (10 ml) of compound 1b (100 mg, 0.66 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 40 mg of a white solid. Yield=14% $^1$HNMR (DMSO, 400 MHz) δ 1.55 (2H, m), 1.68 (4H, m), 2.85 (4H, m), 4.43 (2H, d, J=5.6 Hz), 6.88 (1H, t), 6.98 (2H, m), 7.05 (1H, m), 7.31 (1H, s), 7.42 (1H, d), 7.52 (1H, d, J=8 Hz), 8.52 (1H, s), 11.00 (1H, bs); [M$^{+1}$] 435.3 ($C_{21}H_{21}F_3N_4O_3$ requires 434.41).

Example 32

1-(4-(trifluoromethyl)-2-(4-morpholino)benzyl)-3-(2,3-dihydro-2-oxobenzo[d]oxazol-4-yl)urea (scheme 1)

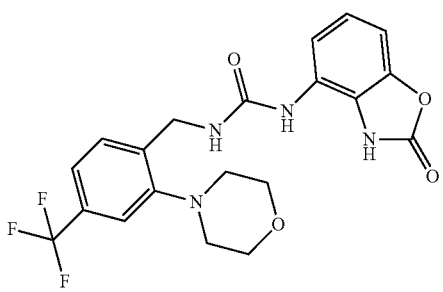 [SMILES: O=C(NCc1ccc(C(F)(F)F)cc1N1CCOCC1)Nc1cccc2oc(=O)[nH]c12]

Preparation of 1-(4-(trifluoromethyl)-2-(4-morpholino)benzyl)-3-(2,3-dihydro-2-oxobenzo[d]oxazol-4-yl)urea Amine 2d (362 mg, 3.8 mmol) (Scheme 7) was dissolved in 20 ml of AcOEt and at 0° C. triphosgene (1.12 g, 1 equiv.) was added to the solution. The mixture was warmed at 80° C. for 4 hours then evaporated and the residue was dissolved in 5 ml of DMF. The solution of the isocyanate was added dropwise to a solution in DMF (10 ml) of compound 1b (384 mg, 2.56 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 200 mg of a pale rose solid. Yield=18% $^1$HNMR (DMSO, 400 MHz) δ 2.91 (4H, m), 3.76 (4H, m), 4.46 (2H, d, J=5.6 Hz), 6.97 (3H, m), 7.05 (1H, m), 7.36 (1H, s), 7.46 (1H, d), 7.54 (1H, d), 8.53 (1H, s), 11.00 (1H, bs); [M$^{+1}$] 437.1 ($C_{20}H_{19}F_3N_4O_4$ requires 436.4).

Example 33

1-(4-chlorobenzyl)-3-(2,3-dihydro-2-oxobenzo[d]oxazol-4-yl)urea (scheme 1)

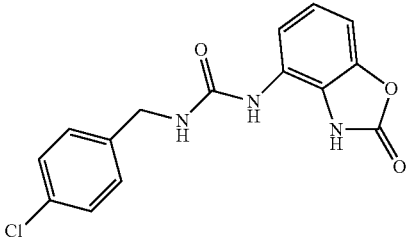 [SMILES: O=C(NCc1ccc(Cl)cc1)Nc1cccc2oc(=O)[nH]c12]

Preparation of 1-(4-chlorobenzyl)-3-(2,3-dihydro-2-oxobenzo[d]oxazol-4-yl)urea Commercially available p-chlorobenzylamine (1.6 g, 11.4 mmol) was dissolved in 60 ml of AcOEt and at 0° C. triphosgene (3.38 g, 1 equiv.) was added to the solution. The mixture was warmed at 80° C. for 4 hours then evaporated and the residue was dissolved in 30 ml of DMF. The solution of the isocyanate was added dropwise to a solution in DMF (10 ml) of compound 1b (1.7 g, 11.4 mmol) and the mixture was warmed at 80° C. for 8 hours. (TLC AcOEt 7/petroleum ether 3). The solvent was evaporated and the crude was dissolved in AcOEt (80 ml) and washed with water (1×50 ml) and brine. The organic phase was dried over sodium sulfate and concentrated under vacuum. The purification of the crude residue by chromatographic column gave 500 mg of a white solid. Yield=14% $^1$HNMR (DMSO, 200 MHz) δ 4.57 (2H, d, J=5.8 Hz), 6.53 (2H, m), 7.04 (1H, m), 7.41 (4H, s), 9.88 (1H, t), 11.53 (1H, s), 11.80 (1H, bs); [M$^{+1}$] 318.5 ($C_{15}H_{12}ClN_3O_3$ requires 317.73).

Example 34

1-(4-(trifluoromethyl)benzyl)-3-(2,3-dihydro-2-oxobenzo[d]oxazol-7-yl)urea (scheme 1)

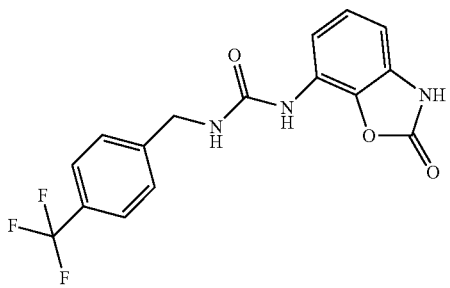 [SMILES: O=C(NCc1ccc(C(F)(F)F)cc1)Nc1cccc2[nH]c(=O)oc12]

Preparation of 5-chloro-7-nitrobenzo[d]oxazol-2(3H)-one 6 (Scheme 3)

DCI (36.4 mmol, 5.9 g) was added in one portion to 2-amino-4-chloro-6-nitrophenol 5 (5 g, 26.5 mmol) suspended in AcOEt (150 ml) and the reaction was stirred vigorously for 2 hours. 100 ml of water were added to the reaction and then the organic phase was eliminated by evaporation. HCl 20% was added (20 ml) and the resulting solid material was filtered and washed with HCl 1N, cold water, MeOH and ether obtaining 5.6 g of a beige solid. Yield=98% $^1$HNMR (DMSO, 200 MHz) δ 7.59 (1H, d, J=2.2 Hz), 7.86 (1H, d, J=2.2 Hz), 12.56 (1H, bs)

Preparation of 7-aminobenzo[d]oxazol-2(3H)-one 1c (Scheme 3)

To compound 6 (4 g, 18.56 mmol) dissolved in a mixture of 4/1 MeOH/DMF (50 ml) C/Pd 10% (500 mg) was added and the reaction was hydrogenated at 60 psi overnight. (TLC AcOEt 3/petroleum ether 7) The reaction was filtrated through a pad of Celite and the filtrate was evaporated under vacuum. The crude solid was crystallized from ether giving 2.8 g of a beige solid. Yield=99%. $^1$HNMR (DMSO, 200 MHz) δ 5.31 (2H, bs), 6.26 (1H, dd, J=7.6 Hz, J'=1 Hz), 6.38 (1H, dd, J=8.4 Hz, J'=1.2 Hz), 6.80 (1H, t, J=8 Hz), 11.32 (1H, bs)

Preparation of 1-(4-(trifluoromethyl)benzyl)-3-(2,3-dihydro-2-oxobenzo[d]oxazol-7-yl)urea Commercially available 4-trifluoromethylbenzylamine (1 ml, 7 mmol) was dissolved in 20 ml of AcOEt and at 0° C. triphosgene (2 g, 7 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1c (700 mg, 4.66 mmol) and the mixture was warmed at 80° C. for 8 hours. (TLC AcOEt 4/petroleum ether 6). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 320 mg of a white solid. Yield=19.5% $^1$HNMR (DMSO, 400 MHz) δ 4.41 (2H, d, J=6 Hz), 6.67 (1H, dd, J=7.6 Hz, J'=1.2 Hz), 7.00 (1H, t, J=8 Hz), 7.09 (1H, t), 7.51 (2H, d, J=8 Hz), 7.70 (3H, m), 8.73 (1H, s), 10.60 (1H, bs); [M$^{+1}$] 352.1 (C$_{16}$H$_{12}$F$_3$N$_3$O$_3$ requires 351.3).

Example 35

1-(4-(trifluoromethyl)-2-(pyrrolidin-1-yl)benzyl)-3-(2,3-dihydro-2-oxobenzo[d]oxazol-7-yl)urea (scheme 1)

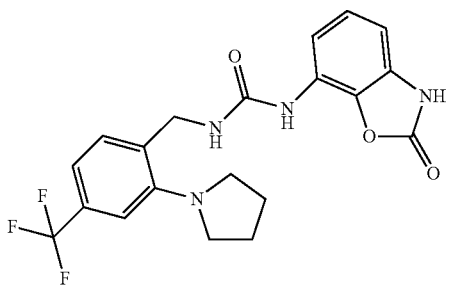 [SMILES: O=C(NCc1ccc(C(F)(F)F)cc1N1CCCC1)Nc1cccc2[nH]c(=O)oc12]

Preparation of 1-(4-(trifluoromethyl)-2-(pyrrolidin-1-yl)benzyl)-3-(2,3-dihydro-2-oxobenzo[d]oxazol-7-yl)urea Amine 2b (795 mg, 3.3 mmol) (Scheme 7) was dissolved in 20 ml of AcOEt and at 0° C. triphosgene (979 mg, 3.3 mmol) was added to the solution.

The mixture was warmed at 80° C. for 4 hours then evaporated and the residue was dissolved in 5 ml of DMF. The solution of the isocyanate was added dropwise to a solution in DMF (10 ml) of compound 1c (330 mg, 2.2 mmol) and the mixture was warmed at 80° C. for 8 hours. (TLC AcOEt 1/petroleum ether 1). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 240 mg of a white solid. Yield=26% $^1$HNMR (DMSO, 200 MHz) δ 1.91 (4H, m), 3.22 (4H, m), 4.38 (2H, d, J=5.4 Hz), 6.66 (1H, dd, J=7.6 Hz, J'=1.2 Hz), 7.00 (3H, m), 7.19 (1H, d, J=8 Hz), 7.39 (1H, d), 7.72 (1H, dd, J=8.6 Hz, J'=1), 8.72 (1H, bs), 11.63 (1H, bs); [M$^{+1}$] 421.3 (C$_{20}$H$_{19}$F$_3$N$_4$O$_3$ requires 420.4).

Example 36

1-(4-(trifluoromethyl)-2-(piperidin-1-yl)benzyl)-3-(2,3-dihydro-2-oxobenzo[d]oxazol-7-yl)urea (scheme 1)

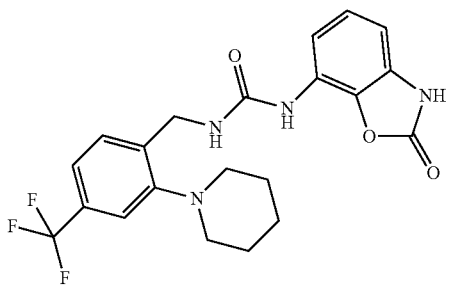 [SMILES: O=C(NCc1ccc(C(F)(F)F)cc1N1CCCCC1)Nc1cccc2[nH]c(=O)oc12]

Preparation of 1-(4-(trifluoromethyl)-2-(piperidin-1-yl)benzyl)-3-(2,3-dihydro-2-oxobenzo[d]oxazol-7-yl)urea Amine 2c (1 g, 3.8 mmol) (Scheme 7) was dissolved in 20 ml of AcOEt and at 0° C. triphosgene (1.13 g, 3.8 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1c (390 mg, 2.6 mmol) and the mixture was warmed at 80° C. for 8 hours. (TLC AcOEt1/petroleum ether 1). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 160 mg of a white solid. Yield=14% $^1$HNMR (DMSO, 200 MHz) δ 1.56 (2H, bs), 1.69 (4H, bs), 2.85 (4H, m), 4.42 (2H, d, J=5.6 Hz), 6.66 (1H, dd, J=8 Hz, J'=0.8 Hz), 7.01 (2H, m), 7.32 (1H, s), 7.44 (2H, dd, J=7.6 Hz), 7.72 (1H, dd, J=8.6 Hz, J'=1 Hz), 8.73 (1H, bs), 11.68 (1H, bs); [M$^{+1}$] 435.2 ($C_{21}H_{21}F_3N_4O_3$ requires 434.4).

Example 37

1-(2-oxo-3H-1,3-benzoxazol-7-yl)-3-[[6-(trifluoromethyl)-3-pyridyl]methyl]urea

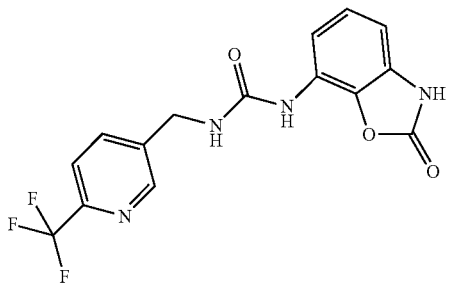 [SMILES: O=C(NCc1ccc(C(F)(F)F)nc1)Nc1cccc2[nH]c(=O)oc12]

Preparation of 1-(2-oxo-3H-1,3-benzoxazol-7-yl)-3-[[6-(trifluoromethyl)-3-pyridyl]methyl]urea To a solution of [6-(trifluoromethyl)-3-pyridyl)]-methanamine (1 g, 4.7 mmol) in THF (30 mL) was added CDI (2.1 mol eq) and the mixture was heated at 70° C. overnight. The reaction mixture was evaporated, water was added and the aqueous phase was extracted with EtOAc (3×20 mL). The recombined organic phases were anhydrified over $Na_2SO_4$ and evaporated at reduced pressure (quantitative yield). The oil obtained (0.34 g, 1.2 mmol) was dissolved in DMF (15 mL) and the bicyclic amine 1c (Scheme 3) was added (0.8 mol eq), then the mixture obtained was heated at 100° C. overnight. The solvent was removed at reduced pressure and the residue was purified by chromatography (1:1 EtOAc:petroleum ether) to obtain the product as a white solid (0.064 g, 20% Yield). $^1$HNMR (DMSO, 200 MHz) δ 4.46 (d, 2H, J=6), 6.66 (d, 1H, J=8), 6.96 (t, 1H), 7.04 (bt, 1H), 7.64 (d, 1H, J=8), 7.86 (m, 2H), 8.70 (s, 1H), 8.77 (s, 1H), 11.60 (bs, 1H). [M$^{+1}$] 358.02 ($C_{15}H_{11}F_3N_4O_3$ requires 357.27).

Example 38

1-(2-oxo-3H-1,3-benzoxazol-7-yl)-3-[[5-(trifluoromethyl)-2-furyl]methyl]urea

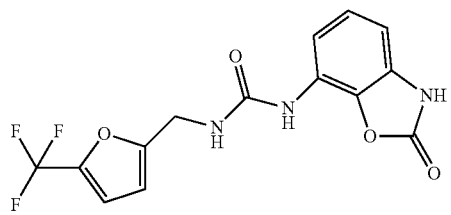 [SMILES: O=C(NCc1ccc(C(F)(F)F)o1)Nc1cccc2[nH]c(=O)oc12]

Preparation of 1-(2-oxo-3H-1,3-benzoxazol-7-yl)-3-[[5-(trifluoromethyl)-2-furyl]methyl]urea To a solution of 2-aminomethyl-5-trifluoromethylfurane (1 g, 6.1 mmol) in THF (30 mL) was added CDI (2.1 mol eq) and the mixture was heated at 70° C. overnight. The reaction mixture was evaporated, water was added and the aqueous phase was extracted with EtOAc (3×20 mL). The recombined organic phases were anhydrified over $Na_2SO_4$ and evaporated at reduced pressure (1.6 g, 5.9 mmol). The oil obtained (0.31 g, 1.19 mmol) was dissolved in DMF (20 mL) and the bicyclic amine 1c (Scheme 3) was added (0.8 mol eq, 0.15 g), then the mixture obtained was heated at 100° C. overnight. The solvent was removed at reduced pressure and the residue was purified by chromatography (100% EtOAc) to obtain the product as white solid (0.05 g, 13% Yield). $^1$HNMR (DMSO, 200 MHz) δ 4.37 (d, 2H, J=6), 6.48 (d, 1H, J=2), 6.70 (dd, 1H), 7.01 (m, 2H), 7.16 (m, 1H), 7.70 (dd, 1H, J=2), 8.69 (s, 1H), 11.62 (bs, 1H). [M$^{+1}$] 341.61 ($C_{14}H_{10}F_3N_3O_4$ requires 341.24).

Example 39

1-(2-oxo-1,3-dihydrobenzimidazol-4-yl)-3-[[2-pyrrolidin-1-yl-6-(trifluoromethyl)-3-pyridyl]methyl]urea

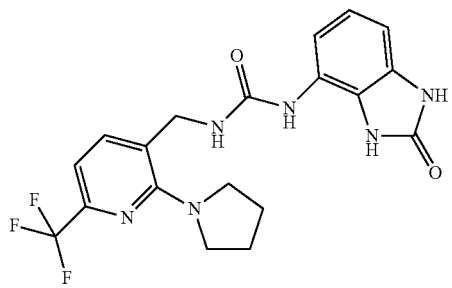 [SMILES: O=C(NCc1ccc(C(F)(F)F)nc1N1CCCC1)Nc1cccc2[nH]c(=O)[nH]c12]

Preparation of 2-(1-pyrrolidin)-6-(trifluoromethyl)-pyridine-3-carbonitrile 28e (Scheme 14)

To 2-chloro-6-trifluoromethyl-nicotinonitrile (0.5 g, 2.4 mmol) was added pyrrolidine (4 mol eq) and the mixture was heated in neat at 90° C. for 3 h. The mixture was concentrated, water was added and the mixture was extracted with EtOAc (3×20 mL). The recombined organic phases were anhydrified and evaporated to dryness to obtain 2-(1-pyrrolidin)-6-(trifluoromethyl)nicotinonitrile as pale yellow oil (0.88 g, quantitative yield). $^1$HNMR (DMSO, 200 MHz) δ 1.44 (m, 4H), 2.10 (m, 4H), 7.25 (d, 1H, J=8), 7.54 (d, 1H).

Preparation of 2-(1-pyrrolidin)-6-(trifluoromethyl)-3-aminomethyl-pyridine 29e

The nitrile 28e (0.88 g) was added in small portion to a mixture of LiAlH$_4$ (0.26 g, 2 mol eq) in Et$_2$O (30 mL) stirred at 0° C. Then the mixture was stirred at room temperature overnight. The excess of LiAlH$_4$ was decomposed by water addition at 0° C., the solid formed was filtered, washed with Et$_2$O and the filtrate was separated. The organic phase was anhydrified over Na$_2$SO$_4$ and evaporated to dryness to obtain 29e as pale yellow oil (0.58 g, 2.3 mmol, 70% Yield) used without further purification.

Preparation of 1-(2-oxo-1,3-dihydrobenzimidazol-4-yl)-3-[[2-pyrrolidin-1-yl-6-(trifluoromethyl)-3-pyridyl]methyl]urea To a solution of 2-(1-pyrrolidinyl)-6-(trifluoromethyl)-3-aminomethyl-pyridine 29e (0.58 g, 2.3 mmol) in THF (25 mL) was added CDI (2.1 mol eq, 0.77 g) and the mixture was heated for 5 h. The reaction mixture was evaporated, water was added and the aqueous phase was extracted with EtOAc (3×20 mL). The recombined organic phases were anhydrified over Na$_2$SO$_4$ and evaporated at reduced pressure. The oil obtained (0.9 g, 2.25 mmol) was dissolved in DMF (20 mL) and the bicyclic amine 1a was added (0.8 mol eq, 0.31 g), then the mixture obtained was heated at 100° C. overnight. The solvent was removed at reduced pressure and the residue was purified by chromatography (9.5:0.5 EtoAc:MeOH) to obtain the product as a pale yellow solid (0.1 g, 0.25 mmol, 12% Yield). $^1$HNMR (DMSO, 400 MHz) δ 1.89 (m, 4H), 3.56 (m, 4H), 4.43 (d, 2H, J=6), 6.60 (dd, 1H), 6.64 (t, 1H), 6.73 (t, 1H), 6.79 (d, 1H), 7.13 (d, 1H, J=6), 7.72 (d, 1H, J=8), 7.95 (s, 1H), 8.31 (s, 1H), 9.97 (bs, 1H), 10.60 (bs, 1H). [M$^{+1}$] 421.10 (C$_{19}$H$_{19}$F$_3$N$_6$O$_2$ requires 420.39).

Example 40

1-[[6-methyl-2-(1-piperidyl)-3-pyridyl]methyl]-3-(2-oxo-1,3-dihydrobenzimidazol-4-yl)urea

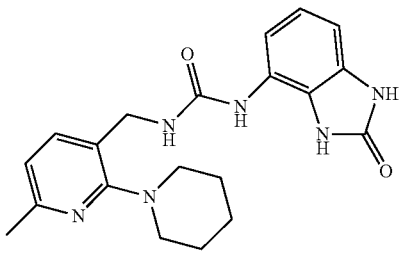 [SMILES: Cc1ccc(CNC(=O)Nc2cccc3[nH]c(=O)[nH]c23)c(N2CCCCC2)n1]

Preparation of 2-(1-piperidyl)-6-methyl-pyridine-3-carbonitrile 32b (Scheme 16)

To 2-chloro-6-methyl-3-pyridine carbonitrile (1 g, 6.5 mmol) was added piperidine (2.56 mL, 4 mol eq) and the mixture was heated in neat at 90° C. for 4 h. The mixture was concentrated, water was added and the mixture was extracted with EtOAc (3×20 mL). The recombined organic phases were anhydrified and evaporated to dryness to obtain 32b as pale yellow oil (1.28 g, quantitative yield). $^1$HNMR (DMSO, 200 MHz) δ 1.54 (m, 6H), 2.16 (m, 4H), 3.11 (s, 3H), 7.28 (d, 1H, J=8), 7.64 (d, 1H).

Preparation of [6-methyl-2-(1-piperidyl)-3-pyridyl]methanamine 33b

The nitrile 32b (1.44 g, 7.1 mmol)) was added in small portion to a mixture of LiAlH$_4$ (0.55 g, 2 mol eq) in Et$_2$O (30 mL) stirred at 0° C. Then the mixture was stirred at room temperature overnight. The excess of LiAlH$_4$ was decomposed by water addition at 0° C., the solid formed was filtered, washed with Et$_2$O and the filtrate was separated. The organic phase was anhydrified over Na$_2$SO$_4$ and evaporated to dryness to obtain 33b as yellow oil (1.06 g, 5.18 mmol, 74% Yield) used without further purification.

Preparation of 1-[[6-methyl-2-(1-piperidyl)-3-pyridyl]methyl]-3-(2-oxo-1,3-dihydrobenzimidazol-4-yl)urea To a solution of 33b (1.06 g, 5.18 mmol) in THF (20 mL) was added CDI (2.1 mol eq, 1.76 g) and the mixture was heated for 6 h. The reaction mixture was evaporated, water was added and the aqueous phase was extracted with EtOAc (3×20 mL). The recombined organic phases were anhydrified over Na$_2$SO$_4$ and evaporated at reduced pressure. The oil obtained (1.04 g, 3.36 mmol) was dissolved in DMF (20 mL) and the bicyclic amine 1a was added (0.8 mol eq, 0.40 g), then the mixture obtained was heated at 100° C. overnight. The solvent was removed at reduced pressure and the residue was purified by chromatography (100% EtoAc)) to obtain the product as a pale yellow solid (0.30 g, 0.78 mmol, 31% Yield). $^1$HNMR (DMSO, 400 MHz) δ 1.63 (m, 6H), 2.34 (s, 3H), 2.95 (m, 4H), 4.26 (d, 2H, J=6), 6.60 (m, 2H), 6.87-6.93 (m, 3H), 7.54 (d, 1H, J=8), 8.28 (s, 1H), 9.99 (bs, 1H), 10.59 (bs, 1H). [M$^{+1}$] 381.5 (C$_{20}$H$_{24}$N$_6$O$_2$ requires 380.44).

Example 41

1-(2-oxo-1,3-dihydrobenzimidazol-4-yl)-3-[[5-(trifluoromethyl)-2-pyridyl]methyl]urea

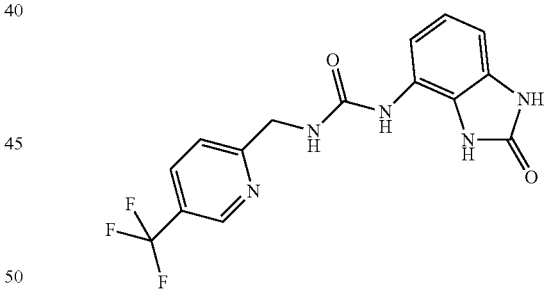

To a solution of triphosgene (0.148 g, 0.37 mol eq) in anh. CH$_2$Cl$_2$ (10 mL) was slowly added the amine 1a (0.2 g, 1.34 mmol) solubilized in CH$_2$Cl$_2$ (10 mL) and DIEA (2.2 mol eq, 0.5 mL). After the addition was completed, the reaction mixture was stirred at room temp. for 15 min. Then the [5-(trifluoromethyl)-2-pyridyl]methanamine (1 mol eq, 0.23 g) solubilized in CH$_2$Cl$_2$ (10 mL) and DIEA (2.2 mol eq, 0.5 mL) was added in one portion. The mixture obtained was stirred at room temp. for 12 h. The solvent was removed at reduced pressure, water was added and the mixture was extracted with EtOAc (3×20 mL). The recombined organic phases were anhydrified over sodium sulfate and evaporated to dryness. The residue was purified by chromatography (9.5: 0.5 EtoAc:MeOH) to obtain the product as yellow solid (0.075 g, 0.22 mmol, 16% Yield). $^1$HNMR (DMSO, 400 MHz) δ 4.35 (d, 2H, J=6), 6.22 (t, 1H, J=4), 6.65 (d, 1H, J=6), 6.88 (m, 2H), 7.63 (d, 1H, J=8), 8.21 (dd, 1H), 8.48 (s, 1H), 8.91 (m, 1H), 9.99 (bs, 1H), 10.60 (bs, 1H). [M$^{+1}$] 351.60 (C$_{15}$H$_{12}$F$_3$N$_5$O$_2$ requires 351.28).

Example 42

1-(4-(trifluoromethyl)benzyl)-3-(3,4-dihydro-3-oxo-2H-benzo[b][1,4]oxazin-5-yl)urea (scheme 1)

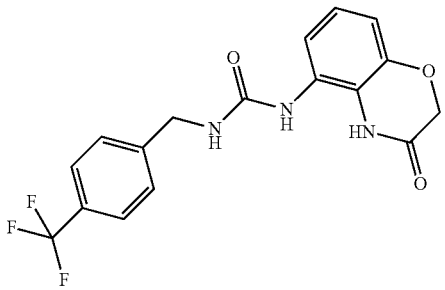 [SMILES: O=C1COc2cccc(NC(=O)NCc3ccc(C(F)(F)F)cc3)c2N1]

Preparation of 5-nitro-2H-benzo[b][1,4]oxazin-3(4H)-one 11 (scheme 5)

To a solution of 2-amino-3-nitrophenol (4.62 g, 30 mmol) in DMF (20 ml) ethylbromoacetate (3.3 ml, 30 mmol) and K$_2$CO$_3$ (4.56 g, 33 mmol) were added and the reaction was stirred at room temperature for 20 hours. The solvent was evaporated and the crude was dissolved in AcOEt (30 ml) and washed with water (1×20 ml) and brine. The organic phase was dried over sodium sulfate and concentrated under vacuum. The purification of the crude residue by crystallization from ether/hexane gave 4.65 g of a yellow solid. Yield: 80%. $^1$HNMR (DMSO, 200 MHz) δ 4.74 (2H, s), 7.15 (1H, t, J=8.4 Hz), 7.41 (1H, dd, J=8.2 Hz, J'=1.6 Hz), 7.77 (1H, dd, J=8.4 Hz, J'=1.2 Hz), 10.38 (1H, bs)

Preparation of 5-amino-2H-benzo[b][1,4]oxazin-3(4H)-one 1e

To compound 11 (2.3 g, 11.85 mmol) dissolved in a mixture of 4/1 MeOH/THF (50 ml) C/Pd 10% (500 mg) was added and the reaction was hydrogenated at 60 psi overnight. (TLC AcOEt 3/petroleum ether 7) The reaction was filtrated through a pad of Celite and the filtrate was evaporated under vacuum. The crude solid was crystallized from ether giving 1.75 g of a beige solid. Yield=90%. $^1$HNMR (DMSO, 200 MHz) δ 4.44 (2H, s), 6.18 (1H, dd, J=8 Hz, J'=1.2 Hz), 6.31 (1H, dd, J=8 Hz, J'=1.2 Hz), 6.64 (1H, t, J=7.8 Hz), 9.96 (1H, bs)

Preparation of 1-(4-(trifluoromethyl)benzyl)-3-(3,4-dihydro-3-oxo-2H-benzo[b][1,4]oxazin-5-yl)urea Commercially available 4-trifluoromethylbenzylamine (1 ml, 7 mmol) was dissolved in 20 ml of AcOEt and at 0° C. triphosgene (2 g, 7 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1e (766 mg, 4.66 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 550 mg of a white solid. Yield=32% $^1$HNMR (DMSO, 400 MHz) δ 4.40 (2H, d, J=5.6 Hz), 4.52 (2H, s), 6.70 (1H, dd, J=8 Hz, J'=1.2 Hz), 6.86 (2H, t, J=8 Hz), 7.16 (1H, dd, J=8 Hz, J'=1.2 Hz), 7.54 (2H, d, J=8 Hz), 7.70 (2H, d, J=8.4 Hz), 8.18 (1H, s), 10.11 (1H, bs); [M$^{+1}$] 366.2 (C$_{17}$H$_{14}$F$_3$N$_3$O$_3$ requires 365.31).

Example 43

1-(4-(trifluoromethyl)-2-(pyrrolidin-1-yl)benzyl)-3-(3,4-dihydro-3-oxo-2H-benzo[b][1,4]oxazin-5-yl)urea (scheme 1)

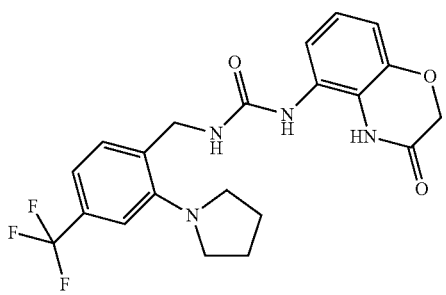 [SMILES: O=C1COc2cccc(NC(=O)NCc3ccc(C(F)(F)F)cc3N3CCCC3)c2N1]

Preparation of 1-(4-(trifluoromethyl)-2-(pyrrolidin-1-yl)benzyl)-3-(3,4-dihydro-3-oxo-2H-benzo[b][1,4]oxazin-5-yl)urea Amine 2b (471 mg, 1.94 mmol) (Scheme 7) was dissolved in 20 ml of AcOEt and at 0° C. triphosgene (576 mg, 1.94 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1e (213 mg, 1.3 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 120 mg of a white solid. Yield=21% $^1$HNMR (DMSO, 400 MHz) δ 1.91 (4H, m), 3.21 (4H, m), 4.48 (2H, d, J=6 Hz), 4.63 (2H, s), 6.64 (2H, dd, J=10.8 Hz, J'=8 Hz), 6.88 (1H, t, J=8 Hz), 7.12 (1H, s), 7.19 (1H, d, J=8.8 Hz), 7.34 (1H, d, J=8 Hz), 8.63 (1H, t), 10.68 (1H, bs), 10.90 (1H, bs); [M$^{+1}$] 435.2 (C$_{21}$H$_{21}$F$_3$N$_4$O$_3$ requires 434.4).

Example 44

1-(4-(trifluoromethyl)-2-(piperidin-1-yl)benzyl)-3-(3,4-dihydro-3-oxo-2H-benzo[b][1,4]oxazin-5-yl)urea (scheme 1)

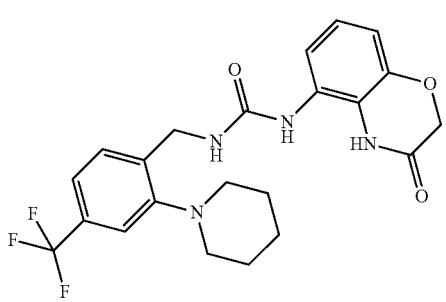 [SMILES: O=C1COc2cccc(NC(=O)NCc3ccc(C(F)(F)F)cc3N3CCCCC3)c2N1]

Preparation of 1-(4-(trifluoromethyl)-2-(piperidin-1-yl)benzyl)-3-(3,4-dihydro-3-oxo-2H-benzo[b][1,4]oxazin-5-yl)urea Amine 2c (1 g, 3.8 mmol) (Scheme 7) was dissolved in 20 ml of AcOEt and at 0° C. triphosgene (1.13 g, 3.8 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1e (425 mg, 2.6 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 530 mg of a white solid. Yield=45% $^1$HNMR (DMSO, 400 MHz) δ 1.56 (2H, bs), 1.69 (4H, bs), 4.55 (2H, d, J=5.6 Hz), 4.64 (2H, s), 6.64 (2H, dd, J=14 Hz, J'=7.6 Hz), 6.88 (1H, t, J=8 Hz), 7.32 (1H, s), 7.39 (2H, s), 8.64 (1H, t), 10.66 (1H, bs), 10.88 (1H, bs); [M$^{+1}$] 449.2 ($C_{22}H_{23}F_3N_4O_3$ requires 448.4).

Example 45

1-(4-(trifluoromethyl)benzyl)-3-(3,4-dihydro-3-oxo-2H-benzo[b][1,4]oxazin-8-yl)urea (scheme 1)

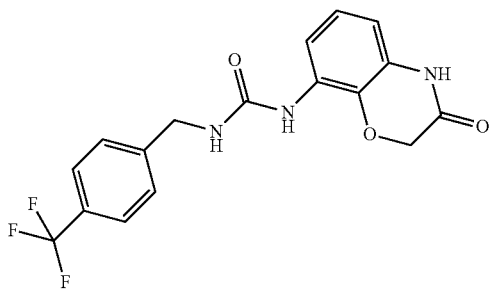 [SMILES: O=C1COc2c(cccc2NC(=O)NCc2ccc(C(F)(F)F)cc2)N1]

Preparation of 6-chloro-8-nitro-2H-benzo[b][1,4]oxazin-3(4H)-one 12 (Scheme 6)

To a solution of 2-amino-4-chloro-6-nitrophenol (5 g, 26.5 mmol) in DMF (20 ml) ethylbromoacetate (3 ml, 26.5 mmol) and $K_2CO_3$ (4 g, 29.15 mmol) were added and the reaction was stirred at room temperature for 20 hours. The solvent was evaporated and the crude was dissolved in AcOEt (30 ml) and washed with NaOH 5%, water and brine. The organic phase was dried over sodium sulfate and concentrated under vacuum. The purification of the crude residue by crystallization from ether/AcOEt gave 1.13 g of a beige solid. Yield: 19%. $^1$HNMR (DMSO, 200 MHz) δ 4.79 (2H, s), 7.15 (1H, d, J=2.6 Hz), 7.66 (1H, d, J=2.8 Hz), 11.21 (1H, bs)

Preparation of 8-amino-2H-benzo[b][1,4]oxazin-3(4H)-one 1f

To compound 12 (1.13 g, 4.92 mmol) dissolved in a mixture of 4/1/1 MeOH/THF/DMF (60 ml) C/Pd 10% (500 mg) was added and the reaction was hydrogenated at 60 psi overnight. (TLC AcOEt 3/petroleum ether 7) The reaction was filtrated through a pad of Celite and the filtrate was evaporated under vacuum. The crude solid was crystallized from ether giving 484 mg of a beige solid. Yield=49%. $^1$HNMR (DMSO, 200 MHz) δ 3.80 (2H, bs), 4.60 (2H, s), 6.63 (1H, dd, J=7.2 Hz, J'=1.4 Hz), 6.83 (2H, m), 10.79 (1H, bs)

Preparation of 1-(4-(trifluoromethyl)benzyl)-3-(3,4-dihydro-3-oxo-2H-benzo[b][1,4]oxazin-8-yl)urea Commercially available 4-trifluoromethylbenzylamine (0.6 ml, 4.2 mmol) was dissolved in 20 ml of AcOEt and at 0° C. triphosgene (1.2 g, 4.2 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1f (460 mg, 2.8 mmol) and the mixture was warmed at 80° C. for 8 hours. (TLC AcOEt). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 250 mg of a white solid. Yield=24% $^1$HNMR (DMSO, 200 MHz) δ 4.31 (2H, d, J=6.2 Hz), 6.46 (1H, dd), 6.70 (2H, t), 6.81 (1H, t), 7.45 (2H, d, J=8 Hz), 7.70 (4H, m), 8.16 (1H, s), 10.72 (1H, bs); [M$^{+1}$] 366.1 ($C_{17}H_{14}F_3N_3O_3$ requires 365.3).

Example 46

1-(2-(dimethylamino)-4-(trifluoromethyl)benzyl)-3-(3,4-dihydro-3-oxo-2H-benzo[b][1,4]oxazin-8-yl)urea (scheme 1)

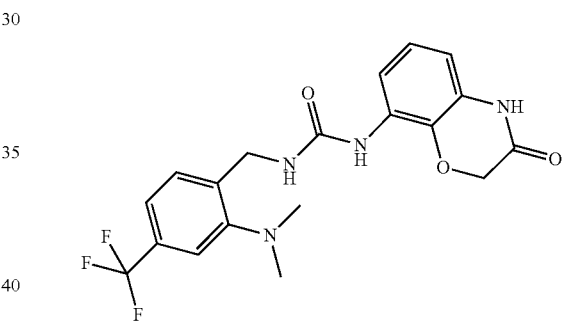

Preparation of 1-(2-(dimethylamino)-4-(trifluoromethyl)benzyl)-3-(3,4-dihydro-3-oxo-2H-benzo[b][1,4]oxazin-8-yl)urea Amine 2a (480 mg, 2.2 mmol) (Scheme 7) was dissolved in 20 ml of AcOEt and at 0° C. triphosgene (653 mg, 2.2 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1f (320 mg, 1.6 mmol) and the mixture was warmed at 80° C. for 8 hours. (TLC AcOEt 1/petroleum ether 1). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 130 mg of a white solid. Yield=19% $^1$HNMR (DMSO, 200 MHz) δ 2.70 (6H, s), 4.39 (2H, d, J=5.2 Hz), 4.62 (2H, s), 6.48 (1H, dd, J=7.8 Hz, J'=1.2 Hz), 6.81 (1H, t), 7.32 (1H, s), 7.42 (3H, m), 7.72 (1H, dd, J'=1.4 Hz), 8.19 (1H, s), 10.65 (1H, bs); [M$^{+1}$] 409.1 ($C_{19}H_{19}F_3N_4O_3$ requires 408.37).

Example 47

1-(4-(trifluoromethyl)-2-(pyrrolidin-1-yl)benzyl)-3-(3,4-dihydro-3-oxo-2H-benzo[b][1,4]oxazin-8-yl) urea (scheme 1)

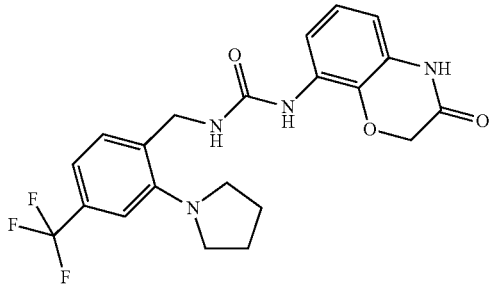 [SMILES: O=C1COc2c(cccc2NC(=O)NCc2ccc(C(F)(F)F)cc2N2CCCC2)N1]

Preparation of 1-(4-(trifluoromethyl)-2-(pyrrolidin-1-yl)benzyl)-3-(3,4-dihydro-3-oxo-2H-benzo[b][1,4]oxazin-8-yl)urea Amine 2b (750 mg, 3.1 mmol) (Scheme 7) was dissolved in 20 ml of AcOEt and at 0° C. triphosgene (920 mg, 3.1 mmol) was added to the solution. The mixture was warmed at 80° C. for 4 hours then evaporated and the residue was dissolved in 5 ml of DMF. The solution of the isocyanate was added dropwise to a solution in DMF (10 ml) of compound 1f (620 mg, 3.1 mmol) and the mixture was warmed at 80° C. for 8 hours. (TLC AcOEt 1/petroleum ether 1). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 120 mg of a white solid. Yield=9% $^1$HNMR (DMSO, 200 MHz) δ 1.89 (4H, m), 3.20 (4H, m), 4.33 (2H, d, J=5.6 Hz), 4.60 (2H, s), 6.45 (1H, dd, J=8 Hz, J'=1.2 Hz), 6.79 (1H, t, J=8.4 Hz), 7.04 (1H, bs), 7.16 (1H, d), 7.23 (1H, t), 7.35 (1H, d), 7.72 (1H, dd, J=8.2 Hz, J'=1.4 Hz), 8.16 (1H, bs), 10.63 (1H, bs); [M$^{+1}$] 435.1 ($C_{21}H_{21}F_3N_4O_3$ requires 434.41).

Example 48

1-(4-(trifluoromethyl)-2-(piperidin-1-yl)benzyl)-3-(3,4-dihydro-3-oxo-2H-benzo[b][1,4]oxazin-8-yl) urea (scheme 1)

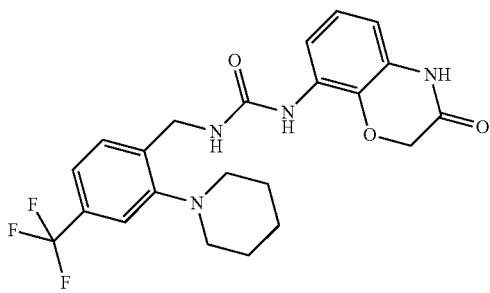 [SMILES: O=C1COc2c(cccc2NC(=O)NCc2ccc(C(F)(F)F)cc2N2CCCCC2)N1]

Preparation of 1-(4-(trifluoromethyl)-2-(piperidin-1-yl)benzyl)-3-(3,4-dihydro-3-oxo-2H-benzo[b][1,4]oxazin-8-yl)urea Amine 2c (420 mg, 1.6 mmol) (Scheme 7) was dissolved in 20 ml of AcOEt and at 0° C. triphosgene (475 mg, 1.6 mmol) was added to the solution. The mixture was warmed at 80° C. for 4 hours then evaporated and dissolved in 5 ml of DMF. The solution of the isocyanate was added drop wise to a solution in DMF (10 ml) of compound 1f (180 mg, 1.1 mmol) and the mixture was warmed at 80° C. for 8 hours. (TLC AcOEt 1/petroleum ether 1). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 160 mg of a white solid. Yield=32% $^1$HNMR (DMSO, 200 MHz) δ 1.57 (2H, bs), 1.68 (4H, bs), 2.85 (4H, m), 4.39 (2H, d, J=5.6 Hz), 4.62 (2H, s), 6.47 (1H, dd, J=7.8 Hz, J'=1.2 Hz), 6.81 (1H, t, J=8 Hz), 7.31 (2H, m), 7.43 (2H, m), 7.74 (1H, dd, J=8.4 Hz, J'=1.2 Hz), 8.18 (1H, bs), 10.65 (1H, bs); [M$^{+1}$] 449.2 ($C_{22}H_{23}F_3N_4O_3$ requires 448.4).

Example 49

1-(4-chlorobenzyl)-3-(3,4-dihydro-3-oxo-2H-benzo[b][1,4]oxazin-8-yl)urea (scheme 1)

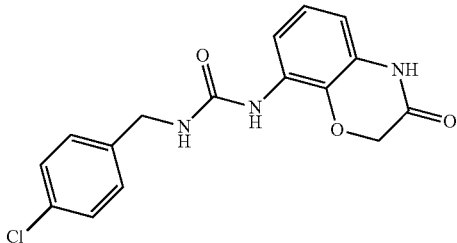 [SMILES: O=C1COc2c(cccc2NC(=O)NCc2ccc(Cl)cc2)N1]

Preparation of 1-(4-chlorobenzyl)-3-(3,4-dihydro-3-oxo-2H-benzo[b][1,4]oxazin-8-yl)urea Commercially available p-chlorobenzylamine (0.98 ml, 8 mmol) was dissolved in 40 ml of AcOEt and at 0° C. triphosgene (2.37 g, 1 equiv.) was added to the solution. The mixture was warmed at 80° C. for 4 hours then evaporated and the residue was dissolved in 20 ml of DMF. The solution of the isocyanate was added dropwise to a solution in DMF (10 ml) of compound 1f (1.42 g, 7.11 mmol) and the mixture was warmed at 80° C. for 8 hours. (TLC AcOEt 1/petroleum ether 1). The solvent was evaporated and to the crude 5% HCl was added. The solid was filtrated, washed with water, MeOH and diethyl ether obtaining 1.6 g of a white product. Yield=68% $^1$HNMR (DMSO, 200 MHz) δ 4.27 (2H, d, J=5.6 Hz), 4.61 (2H, s), 6.47 (1H, dd, J=7.8 Hz, J'=1.2 Hz), 6.81 (1H, t, J=8.2 Hz), 7.35 (5H, m), 7.73 (1H, dd, J=8.2 Hz, J'=1.2 Hz), 8.10 (1H, bs), 10.65 (1H, bs); [M$^{+1}$] 332.4 ($C_{16}H_{14}ClN_3O_3$ requires 331.75).

Example 50

1-(4-chloro-2-(dimethylamino)benzyl)-3-(3,4-dihydro-3-oxo-2H-benzo[b][1,4]oxazin-8-yl)urea
(scheme 1)

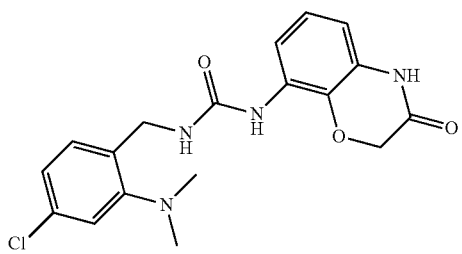 [SMILES: CN(C)c1cc(Cl)ccc1CNC(=O)Nc1cccc2c1OCC(=O)N2]

Preparation of 1-(4-chloro-2-(dimethylamino)benzyl)-3-(3,4-dihydro-3-oxo-2H-benzo[b][1,4]oxazin-8-yl)urea Amine 2af (1 g, 5.5 mmol) (Scheme 8) was dissolved in 20 ml of AcOEt and at 0° C. triphosgene (1.63 g, 1 equiv.) was added to the solution. The mixture was warmed at 80° C. for 4 hours then evaporated and the residue was dissolved in 10 ml of DMF. The solution of the isocyanate was added dropwise to a solution in DMF (10 ml) of compound 1f (860 mg, 4.31 mmol) and the mixture was warmed at 80° C. for 8 hours. (TLC AcOEt 1 petroleum ether 1). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 450 mg of a white solid. Yield=28% $^1$HNMR (DMSO, 200 MHz) δ 2.63 (6H, m), 4.31 (2H, d, J=5.6 Hz), 4.61 (2H, s), 6.47 (1H, dd, J=7.8 Hz, J'=1.6 Hz), 6.81 (1H, t, J=8.4 Hz), 7.07 (2H, m), 7.25 (2H, m), 7.75 (1H, dd, J=8.4 Hz, J'=1.4 Hz), 8.14 (1H, bs), 10.65 (1H, bs); [M$^{+1}$] 374.8 ($C_{17}H_{18}ClN_4O_3$ requires 374.82).

Example 51

1-(4-chloro-2-(pyrrolidin-1-yl)benzyl)-3-(3,4-dihydro-3-oxo-2H-benzo[b][1,4]oxazin-8-yl)urea
(scheme 1)

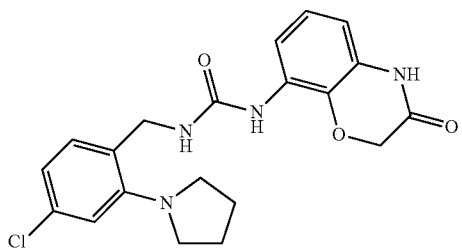 [SMILES: O=C1COc2c(cccc2NC(=O)NCc2ccc(Cl)cc2N2CCCC2)N1]

Preparation of 1-(4-chloro-2-(pyrrolidin-1-yl)benzyl)-3-(3,4-dihydro-3-oxo-2H-benzo[b][1,4]oxazin-8-yl)urea Amine 2ag (1 g, 4.9 mmol) (Scheme 8) was dissolved in 40 ml of AcOEt and at 0° C. triphosgene (1.46 g, 4.9 mmol) was added to the solution. The mixture was warmed at 80° C. for 4 hours then evaporated and dissolved in 5 ml of DMF. The solution of the isocyanate was added dropwise to a solution in DMF (20 ml) of compound 1f (980 mg, 4.9 mmol) and the mixture was warmed at 80° C. for 8 hours. (TLC AcOEt 1/petroleum ether 1). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 250 mg of a white solid. Yield=13% $^1$HNMR (DMSO, 200 MHz) δ 1.89 (4H, m), 3.17 (4H, m), 4.35 (2H, d), 4.61 (2H, s), 6.47 (1H, dd), 6.80 (3H, m), 7.17 (2H, m), 7.82 (1H, dd), 8.15 (1H, bs), 10.75 (1H, bs); [M$^{+1}$] 401.2 ($C_{20}H_{21}ClN_4O_3$ requires 400.86).

Example 52

1-(4-chloro-2-(piperidin-1-yl)benzyl)-3-(3,4-dihydro-3-oxo-2H-benzo[b][1,4]oxazin-8-yl)urea
(scheme 1)

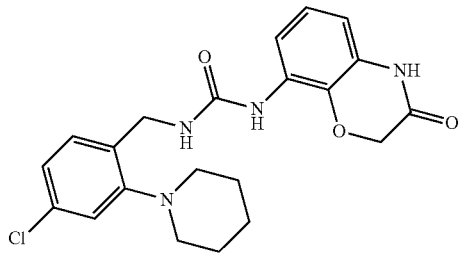 [SMILES: O=C1COc2c(cccc2NC(=O)NCc2ccc(Cl)cc2N2CCCCC2)N1]

Preparation of 1-(4-chloro-2-(piperidin-1-yl)benzyl)-3-(3,4-dihydro-3-oxo-2H-benzo[b][1,4]oxazin-8-yl)urea Amine 2ah (1.7 g, 7.59 mmol) (Scheme 8) was dissolved in 50 ml of AcOEt and at 0° C. triphosgene (2.26 g, 7.59 mmol) was added to the solution. The mixture was warmed at 80° C. for 4 hours then evaporated and dissolved in 5 ml of DMF. The solution of the isocyanate was added dropwise to a solution in DMF (20 ml) of compound 1f (1.5 g, 7.51 mmol) and the mixture was warmed at 80° C. for 8 hours. (TLC AcOEt 1/petroleum ether 1). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 210 mg of a white solid. Yield=7% $^1$HNMR (DMSO, 200 MHz) δ 1.54 (2H, m), 1.66 (4H, m), 2.78 (4H, m), 4.29 (2H, d, J=5.6 Hz), 4.35 (2H, d), 4.61 (2H, s), 6.47 (1H, dd, J=7.8 Hz, J'=1.2 Hz), 6.81 (1H, t, J=8 Hz), 7.13 (4H, m), 7.75 (1H, dd, J=8.2 Hz, J'=1.4 Hz), 8.14 (1H, bs), 10.66 (1H, bs); [M$^{+1}$] 414.9 ($C_{21}H_{23}ClN_4O_3$ requires 414.89).

Example 53

1-(4-methyl-2-(piperidin-1-yl)benzyl)-3-(3,4-dihydro-3-oxo-2H-benzo[b][1,4]oxazin-8-yl)urea (scheme 1)

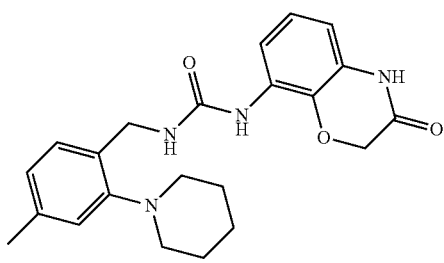 [SMILES: Cc1ccc(CNC(=O)Nc2cccc3c2OCC(=O)N3)c(N2CCCCC2)c1]

Preparation of 1-(4-methyl-2-(piperidin-1-yl)benzyl)-3-(3,4-dihydro-3-oxo-2H-benzo[b][1,4]oxazin-8-yl)urea Amine 2bh (1.08 g, 5.3 mmol) (Scheme 8) was dissolved in 40 ml of AcOEt and at 0° C. triphosgene (1.56 g, 5.4 mmol) was added to the solution. The mixture was warmed at 80° C. for 4 hours then evaporated and the residue was dissolved in 15 ml of DMF. The solution of the isocyanate was added dropwise to a solution in DMF (10 ml) of compound 1f (1 g, 5.46 mmol) and the mixture was warmed at 80° C. for 8 hours. (TLC AcOEt 1/petroleum ether 9). The solvent was evaporated and the crude was dissolved in AcOEt (50 ml) and washed with water (1×30 ml) and brine. The organic phase was dried over sodium sulfate and concentrated under vacuum. The purification of the crude residue by chromatographic column gave 150 mg of a white solid. Yield=7% $^1$HNMR (DMSO, 200 MHz) δ 1.63 (6H, m), 2.25 (3H, s), 2.76 (4H, m), 4.28 (2H, d, J=5.4 Hz), 4.61 (2H, s), 6.46 (1H, dd, J=7.8 Hz, J'=1.4 Hz), 6.81 (3H, m), 7.12 (2H, m), 7.75 (1H, dd, J=8.2 Hz, J'=1.6 Hz), 8.11 (1H, s), 10.66 (1H, bs); [M$^{+1}$] 395.0 ($C_{22}H_{26}N_4O_3$ requires 394.5).

Example 54

1-(((6-chloropyridin-3-yl)methyl)-3-(3,4-dihydro-3-oxo-2H-benzo[b][1,4]oxazin-8-yl)urea (scheme 1)

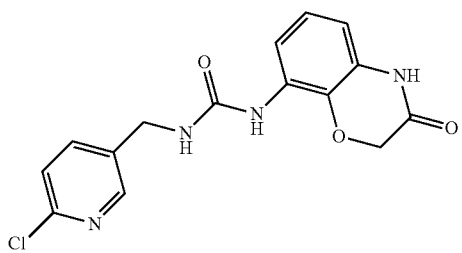 [SMILES: O=C1COc2c(cccc2NC(=O)NCc2ccc(Cl)nc2)N1]

Preparation of 1-((((6-chloropyridin-3-yl)methyl)-3-(3,4-dihydro-3-oxo-2H-benzo[b][1,4]oxazin-8-yl)urea Commercially available (6-chloropyridin-3-yl)methanamine (800 mg, 5.61 mmol) was dissolved in 40 ml of AcOEt and at 0° C. triphosgene (1.54 g, 5.6 mmol) was added to the solution. The mixture was warmed at 80° C. for 4 hours then evaporated and the residue was dissolved in 10 ml of DMF. The solution of the isocyanate was added dropwise to a solution in DMF (10 ml) of compound 1f (900 mg, 4.51 mmol) and the mixture was warmed at 80° C. for 8 hours. (TLC AcOEt 9.5/MeOH 0.5). The solvent was evaporated and the crude was dissolved in AcOEt (80 ml) and washed with water (1×40 ml) and brine. The organic phase was dried over sodium sulfate and concentrated under vacuum. The purification of the crude residue by chromatographic column gave 180 mg of a beige solid. Yield=12% $^1$HNMR (DMSO, 200 MHz) δ 4.31 (2H, d, J=5.6 Hz), 4.60 (2H, s), 6.47 (1H, dd), 6.81 (1H, t), 7.40 (1H, t), 7.50 (1H, d, J=8.2 Hz), 7.72 (2H, m), 8.13 (1H, bs), 8.34 (1H, bs), 10.66 (1H, bs); [M$^{+1}$] 332.8 ($C_{15}H_{13}ClN_4O_3$ requires 332.74).

Example 55

2-(4-(trifluoromethyl)phenyl)-N-(2,3-dihydro-2-oxo-1H-benzo[d]imidazol-4-yl)acetamide (scheme 10)

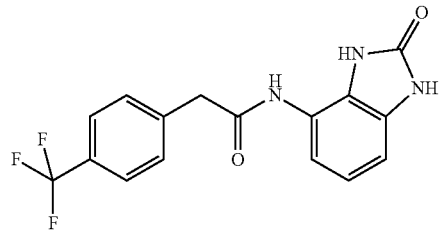 [SMILES: O=C(Cc1ccc(C(F)(F)F)cc1)Nc1cccc2[nH]c(=O)[nH]c12]

Preparation of 2-(4-(trifluoromethyl)phenyl)-N-(2,3-dihydro-2-oxo-1H-benzo[d]imidazol-4-yl)acetamide 4-trifluoromethylphenylacetic acid (300 mg, 1.47 mmol) was dissolved in 20 ml of THF and at 0° C. DEPC (0.28 ml, 1.3 equiv) and amine 1a (260 mg, 1.2 equiv.) were added to the solution. The mixture was warmed at 80° C. overnight, then evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt as eluant gave 150 mg of a white solid. Yield=30% $^1$HNMR (DMSO, 400 MHz) δ 3.78 (2H, s), 6.75 (1H, d), 6.84 (1H, t), 7.05 (1H, d), 7.56 (2H, d, J=8 Hz), 7.70 (2H, d, J=8 Hz), 9.80 (1H, bs), 10.18 (1H, bs), 10.64 (1H, bs); [M$^{+1}$] 336.1 ($C_{16}H_{12}F_3N_3O_2$ requires 335.3).

Example 56

2-(4-(trifluoromethyl)phenyl)-N-(2,3-dihydro-2-oxobenzo[d]oxazol-4-yl)acetamide (scheme 10)

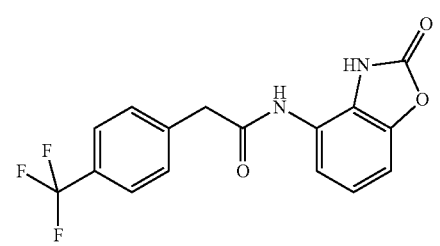 [SMILES: O=C(Cc1ccc(C(F)(F)F)cc1)Nc1cccc2oc(=O)[nH]c12]

Preparation of 2-(4-(trifluoromethyl)phenyl)-N-(2,3-dihydro-2-oxobenzo[d]oxazol-4-yl)acetamide 4-trifluoromethylphenylacetic acid (453 mg, 2.2 mmol) was dissolved in 20 ml of THF and at 0° C. DEPC (0.43 ml, 1.3 equiv) and amine 1b (400 mg, 2.66 mmol) were added to the solution. The mixture was warmed at 80° C. overnight, then evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt as eluant gave 360 mg of a white solid. Yield=48% $^1$HNMR (DMSO, 200 MHz) δ 3.80 (2H, s), 7.10 (3H, m), 7.58 (2H, d, J=8.4 Hz), 7.70 (2H, d, J=8.2 Hz), 10.06 (1H, bs), 11.14 (1H, bs); [M$^{+1}$] 336.9 ($C_{16}H_{11}F_3N_2O_3$ requires 336.3).

Example 57

2-(4-(trifluoromethyl)phenyl)-N-(2,3-dihydro-2-oxobenzo[d]oxazol-7-yl)acetamide (scheme 10)

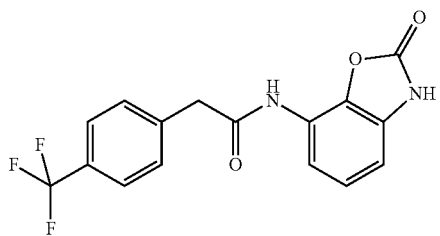 [SMILES: O=C(Cc1ccc(C(F)(F)F)cc1)Nc1cccc2[nH]c(=O)oc12]

Preparation of 2-(4-(trifluoromethyl)phenyl)-N-(2,3-dihydro-2-oxobenzo[d]oxazol-7-yl)acetamide 4-trifluoromethylphenylacetic acid (453 mg, 2.2 mmol) was dissolved in 20 ml of THF and at 0° C. DEPC (0.43 ml, 1.3 equiv) and amine 1c (400 mg, 2.66 mmol) were added to the solution. The mixture was warmed at 80° C. overnight, then evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt 3/petroleum ether 7 as eluant gave 340 mg of a white solid. Yield=46% $^1$HNMR (DMSO, 200 MHz) δ 3.86 (2H, s), 6.86 (1H, d), 7.06 (1H, t), 7.58 (3H, m), 7.70 (2H, d, J=8.4 Hz), 10.32 (1H, bs), 8.73 (1H, bs), 11.80 (1H, bs); [M$^{+1}$] 337.2 ($C_{16}H_{11}F_3N_2O_3$ requires 336.3).

Example 58

2-(4-(trifluoromethyl)phenyl)-N-(3,4-dihydro-3-oxo-2H-benzo[b][1,4]oxazin-5-yl)acetamide (scheme 10)

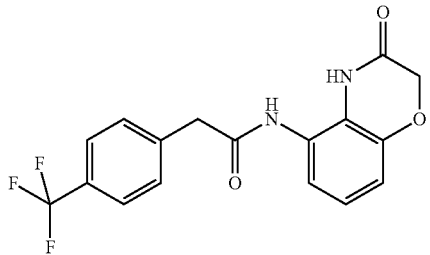 [SMILES: O=C(Cc1ccc(C(F)(F)F)cc1)Nc1cccc2c1NC(=O)CO2]

Preparation of 2-(4-(trifluoromethyl)phenyl)-N-(3,4-dihydro-3-oxo-2H-benzo[b][1,4]oxazin-5-yl)acetamide 4-trifluoromethylphenylacetic acid (408 mg, 2 mmol) was dissolved in 20 ml of THF and at 0° C. DEPC (0.358 ml, 1.2 equiv) and amine 1d (427 mg, 2.6 mmol) were added to the solution. The mixture was warmed at 80° C. overnight, then evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt as eluant gave 550 mg of a white solid. Yield=78.5% $^1$HNMR (DMSO, 200 MHz) δ 3.81 (2H, s), 4.55 (2H, s), 6.87 (2H, m), 7.05 (1H, dd, J=7.6 Hz, J'=6 Hz), 7.56 (2H, d, J=8.2 Hz), 7.70 (2H, d, J=8 Hz), 9.69 (1H, bs), 10.38 (1H, bs); [M$^{+1}$] 351.2 ($C_{17}H_{13}F_3N_2O_3$ requires 350.3).

Example 59

N-(4-(trifluoromethyl)benzyl)-2,3-dihydro-2-oxobenzo[d]oxazole-4-carboxamide (scheme 11)

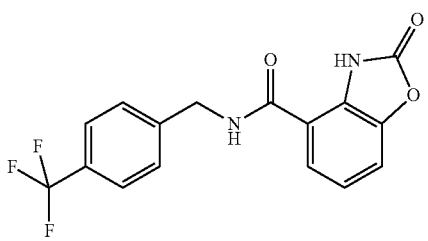 [SMILES: O=C(NCc1ccc(C(F)(F)F)cc1)c1cccc2oc(=O)[nH]c12]

Preparation of 2,3-dihydro-2-oxobenzo[d]oxazole-4-carboxylic acid 21

2-amino-3-hydroxybenzoic acid (1.2 g, 7.8 mmol) was suspended in 20 ml of THF and at 0° C. CDI (1.9 g, 1.5 equiv.) was added. The mixture was warmed at 80° C. for 5 hours. The solvent was evaporated and the crude was dissolved in AcOEt (30 ml) and washed with water (1×20 ml) and brine. The organic phase was dried over sodium sulfate and concentrated under vacuum. The purification of the crude residue by crystallization from EtOAc/ether gave 520 mg of an orange solid. Yield=37% $^1$HNMR (DMSO, 200 MHz) δ 7.45 (3H, m), 10.40 (1H, bs), 12.00 (1H, bs)

Preparation of N-(4-(trifluoromethyl)benzyl)-2,3-dihydro-2-oxobenzo[d]oxazole-4-carboxamide 2,3-dihydro-2-oxobenzo[d]oxazole-4-carboxylic acid 21 (260 mg, 1.45 mmol) was dissolved in 20 ml of THF and at 0° C. DEPC (0.260 ml, 1.2 equiv) and 4-chloro-2-trifluorobenzylamine (0.25 ml, 1.2 equiv.) were added to the solution. The mixture was warmed at 80° C. overnight, then evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt 3/petroleum ether 7 as eluant gave 110 mg of a white solid. Yield=22.5% $^1$HNMR (DMSO, 200 MHz) δ 4.58 (2H, d, J=5.8 Hz), 7.16 (1H, t, J=8 Hz), 7.42 (1H, dd, J=8.2 Hz, J'=1

Hz), 7.55 (2H, d, J=8.2 Hz), 7.65 (3H, m), 9.29 (1H, bt), 11.60 (1H, bs); [M$^{+1}$] 336.9 (C$_{16}$H$_{11}$F$_3$N$_2$O$_3$ requires 336.3).

Example 60

N-(4-(trifluoromethyl)-2-(piperidin-1-yl)benzyl)-2,3-dihydro-2-oxobenzo[d]oxazole-4-carboxamide (scheme 11)

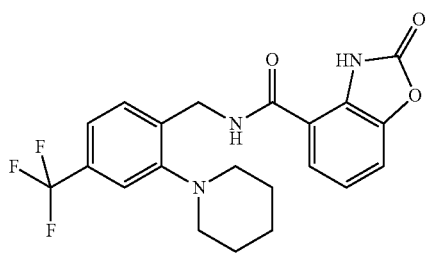 [SMILES: O=C(NCc1ccc(C(F)(F)F)cc1N1CCCCC1)c1cccc2oc(=O)[nH]c12]

Preparation of N-(4-(trifluoromethyl)-2-(piperidin-1-yl)benzyl)-2,3-dihydro-2-oxobenzo[d]oxazole-4-carboxamide 2,3-dihydro-2-oxobenzo[d]oxazole-4-carboxylic acid 21 (560 mg, 3.1 mmol) was dissolved in 20 ml of THF and at 0° C. DEPC (0.55 ml, 1.2 equiv) and amine 2c (964 mg, 1.2 equiv.) were added to the solution. The mixture was warmed at 80° C. overnight, then evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt 4/petroleum ether 6 as eluant gave 250 mg of a pale yellow solid. Yield=19% $^1$HNMR (DMSO, 200 MHz) δ 4.58 (2H, d, J=5.8 Hz), 7.14 (1H, t, J=8 Hz), 7.41 (4H, m), 7.68 (1H, dd, J=8 Hz, J'=0.8 Hz), 9.20 (1H, bt), 11.59 (1H, bs); [M$^{+1}$] 420.2 (C$_{21}$H$_{20}$F$_3$N$_3$O$_3$ requires 419.4).

Example 61

N-(4-(trifluoromethyl)-2-morpholinobenzyl)-2,3-dihydro-2-oxobenzo[d]oxazole-4-carboxamide (scheme 11)

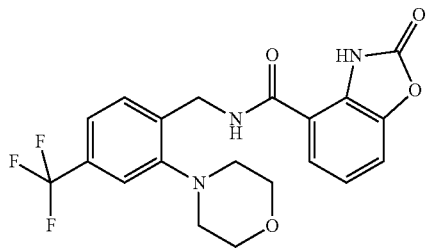 [SMILES: O=C(NCc1ccc(C(F)(F)F)cc1N1CCOCC1)c1cccc2oc(=O)[nH]c12]

Preparation of N-(4-(trifluoromethyl)-2-morpholinobenzyl)-2,3-dihydro-2-oxobenzo[d]oxazole-4-carboxamide 2,3-dihydro-2-oxobenzo[d]oxazole-4-carboxylic acid 21 (240 mg, 1.3 mmol) was dissolved in 20 ml of THF and at 0° C. DEPC (0.23 ml, 1.2 equiv) and amine 2d (420 mg, 1.2 equiv.) were added to the solution. The mixture was warmed at 80° C. overnight, then evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt 4/petroleum ether 6 as eluant gave 100 mg of a white solid. Yield=18% $^1$HNMR (DMSO, 200 MHz) δ 2.94 (4H, bs), 3.78 (4H, bs), 4.64 (2H, d, J=5.6 Hz), 7.18 (1H, t), 7.43 (4H, m), 7.66 (1H, d), 9.35 (1H, bs), 11.60 (1H, bs); [M$^{+1}$] 422.2 (C$_{20}$H$_{18}$F$_3$N$_3$O$_4$ requires 421.37).

Example 62

N-(4-(trifluoromethyl)benzyl)-3,4-dihydro-3-oxo-2H-benzo[b][1,4]oxazine-5-carboxamide (scheme 11)

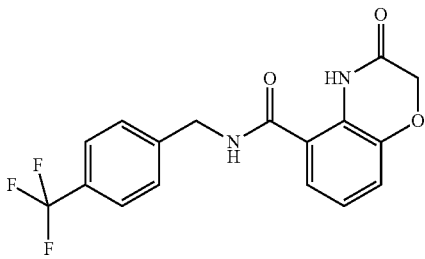 [SMILES: O=C1COc2cccc(C(=O)NCc3ccc(C(F)(F)F)cc3)c2N1]

Preparation of N-(4-(trifluoromethyl)benzyl)-2-amino-3-hydroxybenzamide 22a 2-amino-3-hydroxybenzoic acid (2 g, 13 mmol) was dissolved in 20 ml of DMF and at 0° C. EDCI (2.7 g, 1.2 equiv.), hydroxybenzotriazole (1.9 g, 1.2 equiv.) and 4-trifluoromethylbenzylamine (2 ml, 1.2 equiv.) were added. The mixture was stirred at rt for 20 hours. The solvent was evaporated and the crude was dissolved in AcOEt (30 ml) and washed with water (1×20 ml) and brine. The organic phase was dried over sodium sulfate and concentrated under vacuum. The purification of the crude residue by crystallization from EtOAc/ether gave 3.5 g of a beige solid. Yield=86% $^1$HNMR (DMSO, 200 MHz) δ 4.49 (2H, d, J=5.6 Hz), 6.00 (2H, bs), 6.41 (1H, t, J=8 Hz), 6.76 (1H, d, J=7.6 Hz), 7.11 (1H, d, J=8.2 Hz), 7.51 (2H, d, J=8 Hz), 7.69 (2H, d, J=8 Hz), 8.81 (1H, bt), 9.58 (1H, bs); [M$^{+1}$] 311.1 (C$_{15}$H$_{13}$F$_3$N$_2$O$_2$ requires 310.27).

Preparation of N-(4-(trifluoromethyl)benzyl)-3,4-dihydro-3-oxo-2H-benzo[b][1,4]oxazine-5-carboxamide N-(4-(trifluoromethyl)benzyl)-2-amino-3-hydroxybenzamide 22a (1 g, 3.2 mmol) was dissolved in 20 ml of DMF and at 0° C. TEA (0.9 ml, 2 equiv.) and chloroacetyl chloride (0.3 ml, 1.2 equiv.) were added. The mixture was stirred at rt for 2 hours. K$_2$CO$_3$ (885 mg, 2 equiv.) was added and the reaction was stirred at rt for 20 hours. The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt 1/petroleum ether 1 as eluant gave 500 mg of a white solid. Yield=44% $^1$HNMR (DMSO, 200 MHz) δ 4.56 (2H, d, J=5.4 Hz), 4.65 (2H, s), 7.04 (2H, t), 7.17 (1H, d, J=7.8 Hz), 7.55 (2H, d, J=8 Hz), 7.71 (2H, d, J=8.2 Hz), 9.52 (1H, bs), 10.96 (1H, bs); [M$^{+1}$] 351.1 (C$_{17}$H$_{13}$F$_3$N$_2$O$_3$ requires 350.3).

Example 63

N-(4-(trifluoromethyl)-2-(piperidin-1-yl)benzyl)-3,4-dihydro-3-oxo-2H-benzo[b][1,4]oxazine-5-carboxamide (scheme 11)

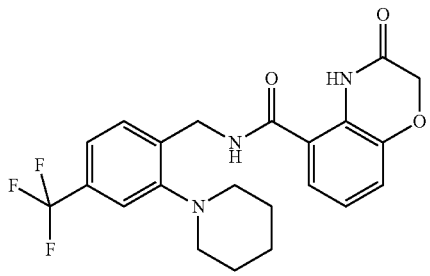 [SMILES: O=C1COc2cccc(C(=O)NCc3ccc(C(F)(F)F)cc3N3CCCCC3)c2N1]

Preparation of N-(4-(trifluoromethyl)-2-(piperidin-1-yl)benzyl)-2-amino-3-hydroxybenzamide 22b 2-amino-3-hydroxybenzoic acid (1 g, 6.5 mmol) was dissolved in 20 ml of DMF and at 0° C. EDCI (1.4 g, 1.2 equiv.), hydroxybenzotriazole (1 g, 1.2 equiv.) and amine 2c (2 g, 1.2 equiv.) were added. The mixture was stirred at rt for 20 hours. The solvent was evaporated and the crude was dissolved in AcOEt (30 ml) and washed with water (1×20 ml) and brine. The organic phase was dried over sodium sulfate and concentrated under vacuum. The purification of the crude residue by crystallization from EtOAc/ether gave 1.6 g of a beige solid. Yield=62.5% [M$^{+1}$] 393.4 (C$_{20}$H$_{22}$F$_3$N$_3$O$_2$ requires 393.4).

Preparation of N-(4-(trifluoromethyl)-2-(piperidin-1-yl)benzyl)-3,4-dihydro-3-oxo-2H-benzo[b][1,4]oxazine-5-carboxamide N-(4-(trifluoromethyl)-2-(piperidin-1-yl)benzyl)-2-amino-3-hydroxybenzamide 22b (2.5 g, 6.4 mmol) was dissolved in 20 ml of DMF and at 0° C. TEA (1.8 ml, 2 equiv.) and chloroacetyl chloride (0.6 ml, 1.2 equiv.) were added. The mixture was stirred at rt for 2 hours. K$_2$CO$_3$ (1.77 g, 2 equiv.) was added and the reaction was stirred at rt for 20 hours. The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt 1/petroleum ether 1 as eluant gave 1 g of a white solid. Yield=36% $^1$HNMR (DMSO, 200 MHz) δ 1.57 (2H, bs), 1.69 (4H, bs), 2.82 (4H, m), 4.60 (2H, d, J=5.4 Hz), 4.67 (2H, s), 7.09 (1H, t, J=7.8 Hz), 7.20 (1H, dd, J=8 Hz, J'=1.2 Hz), 7.33 (1H, m), 7.41 (2H, m), 7.57 (1H, m), 9.38 (1H, bt), 11.02 (1H, bs); [M$^{+1}$] 434.3 (C$_{22}$H$_{22}$F$_3$N$_3$O$_3$ requires 433.4).

Example 64

N-(4-(trifluoromethyl)-2-(piperidin-1-yl)benzyl)-3,4-dihydro-3-oxo-2H-benzo[b][1,4]oxazine-8-carboxamide (scheme 11)

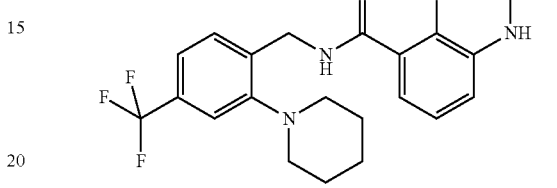

Preparation of N-(4-(trifluoromethyl)-2-(piperidin-1-yl)benzyl)-3-amino-2-hydroxybenzamide 24b 3-amino-2-hydroxybenzoic acid (1 g, 6.5 mmol) was dissolved in 20 ml of DMF and at 0° C. EDCI (1.4 g, 1.2 equiv.), hydroxybenzotriazole (1 g, 1.2 equiv.) and amine 2c (2 g, 1.2 equiv.) were added. The mixture was stirred at rt for 20 hours. The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt 1/petroleum ether 9 as eluant gave 1.3 g of a beige solid. Yield=51% [M$^{+1}$] 393.4 (C$_{20}$H$_{22}$F$_3$N$_3$O$_2$ requires 393.4).

Preparation of N-(4-(trifluoromethyl)-2-(piperidin-1-yl)benzyl)-3,4-dihydro-3-oxo-2H-benzo[b][1,4]oxazine-8-carboxamide N-(4-(trifluoromethyl)-2-(piperidin-1-yl)benzyl)-3-amino-2-hydroxybenzamide 24b (830 mg, 2.1 mmol) was dissolved in 10 ml of DMF and at 0° C. TEA (0.58 ml, 2 equiv.) and chloroacetyl chloride (0.2 ml, 1.2 equiv.) were added. The mixture was stirred at rt for 2 hours. K$_2$CO$_3$ (580 mg, 2 equiv.) was added and the reaction was stirred at rt for 20 hours. The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column using AcOEt 1/petroleum ether 1 as eluant gave 460 mg of a white solid. Yield=50% $^1$HNMR (DMSO, 200 MHz) δ 1.57 (2H, bs), 1.69 (4H, bs), 2.84 (4H, m), 4.58 (2H, d, J=5.2 Hz), 4.69 (2H, s), 7.03 (2H, m), 7.30 (2H, m), 7.45 (2H, m), 8.70 (1H, bt), 10.85 (1H, bs); [M$^{+1}$] 434.1 (C$_{22}$H$_{22}$F$_3$N$_3$O$_3$ requires 433.4).

Example 65

3,4-dihydro-3-oxo-2H-benzo[b][1,4]oxazin-5-yl 4-(trifluoromethyl)benzylcarbamate (scheme 12)

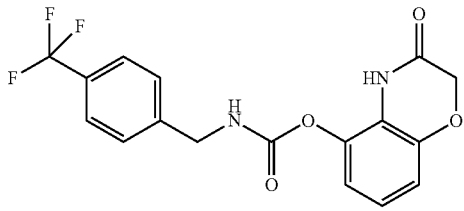 [SMILES: O=C1COc2cccc(OC(=O)NCc3ccc(C(F)(F)F)cc3)c2N1]

Preparation of 5-hydroxy-2H-benzo[b][1,4]oxazin-3(4H)-one 25

TEA (3.34 ml, 2 equiv.) and after chloroacetyl chloride (1.15 ml, 1.2 equiv.) were added dropwise to a solution of commercially available 2-aminobenzene-1,3-diol (1.5 g, 11.99 mmol) in 20 ml of DMF. After one hours of stirring at room temperature, $K_2CO_3$ (3.3 g, 2 equiv.) was added and the reaction was stirred at room temperature overnight. The solvent was evaporated and to the residue water was added. After filtration, the solid material was washed with MeOH and diethyl ether giving 410 mg of a grey solid. Yield=21% $^1$HNMR (DMSO, 200 MHz) δ 3.47 (1H, bs), 4.47 (2H, s), 6.44 (2H, m), 6.72 (1H, t, J=8 Hz)

Preparation of 3,4-dihydro-3-oxo-2H-benzo[b][1,4]oxazin-5-yl 4-(trifluoromethyl)benzylcarbamate 4-trifluoromethylbenzylamine (0.52 ml, 3.6 mmol) was dissolved in 20 ml of AcOEt and at 0° C. triphosgene (1 g, 3.6 mmol) was added to the solution. The mixture was warmed at 80° C. for 4 hours then evaporated and the residue was dissolved in 5 ml of DMF. The solution of the isocyanate was added dropwise in DMF (10 ml) of compound 25 (400 mg, 2.42 mmol) and TEA (0.34 ml, 1 equiv.) and the mixture was stirred at rt for 8 hours. (TLC AcOEt 1/petroleum ether 1). The solvent was evaporated and the crude was dissolved in AcOEt (30 ml) and washed with water (1×20 ml) and brine. The organic phase was dried over sodium sulfate and concentrated under vacuum. The purification of the crude residue by chromatographic column gave 400 mg of a white solid. Yield=45% $^1$HNMR (DMSO, 200 MHz) δ 4.38 (2H, d, J=6.4 Hz), 4.57 (2H, s), 6.85 (3H, m), 7.59 (2H, d, J=8.2 Hz), 7.72 (2H, d, J=8.4 Hz), 8.15 (1H, bt), 10.61 (1H, bs); [M$^{+1}$] 367.1 ($C_{17}H_{13}F_3N_2O_4$ requires 366.3).

Example 66

1-(2-oxo-1,3-dihydrobenzimidazol-4-yl)-3-[[6-(trifluoromethyl)-3-pyridyl]methyl]urea

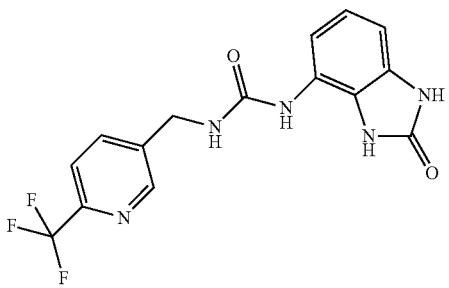 [SMILES: O=C(NCc1ccc(C(F)(F)F)nc1)Nc1cccc2[nH]c(=O)[nH]c12]

Preparation of 1-(2-oxo-1,3-dihydrobenzimidazol-4-yl)-3-[[6-(trifluoromethyl)-3-pyridyl]methyl]urea To a solution of 3-aminomethyl-6-trifluoromethylpyridine (1 g, 4.7 mmol) in THF (30 mL) was added CDI (2.1 mol eq) and the mixture was heated at 70° C. overnight. The reaction mixture was evaporated, water was added and the aqueous phase was extracted with EtOAc (3×20 mL). The recombined organic phases were anhydrified over $Na_2SO_4$ and evaporated at reduced pressure. The oil obtained (0.96 g, 3.5 mmol) was dissolved in DMF (20 mL) and the bicyclic amine 1a was added (0.8 mol eq), then the mixture obtained was heated at 100° C. overnight. The solvent was removed at reduced pressure and the residue was purified by crystallization from a mixture of MeOH/EtOAc to obtain the product as a pale yellow solid (0.42 g, 1.2 mmol, 34% Yield). $^1$HNMR (DMSO, 400 MHz) δ 4.43 (bs, 2H), 6.64 (d, 1H, J=6), 6.83 (t, 1H, J=8), 6.96 (d, 2H, J=8), 7.89 (d, 1H), 8.03 (d, 1H), 8.42 (bs, 1H), 8.72 (s, 1H), 10.07 (bs, 1H), 10.59 (bs, 1H). [M$^{+1}$] 351.80 ($C_{15}H_{12}F_3N_5O_2$ requires 351.28).

Example 67

1-[[2-isopropoxy-4-(trifluoromethyl)phenyl]methyl]-3-(2-oxo-1,3-dihydrobenzimidazol-4-yl)urea

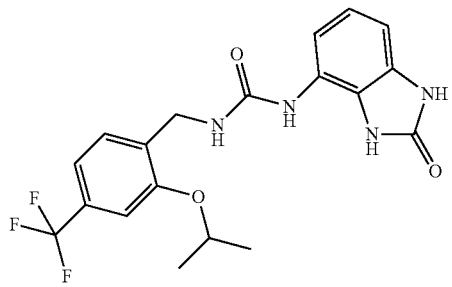 [SMILES: CC(C)Oc1cc(C(F)(F)F)ccc1CNC(=O)Nc1cccc2[nH]c(=O)[nH]c12]

Preparation of 2-isopropoxy-4-(trifluoromethyl)benzonitrile 26a (Scheme 13)

The 2-fluoro-4-(trifluoromethyl)-benzonitrile (0.5 mL, 3.59 mmol) was added in small portion to a mixture of NaH 60% (4 mol eq) in isopropanol (10 mL). The reaction mixture was heated at 50° C. overnight. The solvent was distilled and water was added to the residue. The aqueous solution was extracted with EtOAc (3×25 mL) and the organic phases were evaporated at reduced pressure to give e as a white solid (0.84 g, quantitative yield). $^1$HNMR (DMSO, 200 MHz) δ 1.23 (s, 3H), 1.34 (s, 3H), 4.99 (m, 1H), 7.44 (m, 2H), 8.01 (d, 1H, J=8).

Preparation of [2-isopropoxy-4-(trifluoromethyl)phenyl]methanamine 27a

The nitrile 26a (0.84 g, 3.66 mmol)) was added in small portion to a mixture of $LiAlH_4$ (0.28 g, 2 mol eq) in $Et_2O$ (30 mL) stirred at 0° C. Then the mixture was stirred at room temperature overnight. The excess of $LiAlH_4$ was decomposed by water addition at 0° C., the solid formed was filtered, washed with $Et_2O$ and the filtrate was separated. The organic phase was anhydrified over $Na_2SO_4$ and evaporated to dryness to obtain 27a as yellow oil (0.80 g, 3.64 mmol, 96% Yield).

Preparation of 1-[[2-isopropoxy-4-(trifluoromethyl)phenyl]methyl]-3-(2-oxo-1,3-dihydrobenzimidazol-4-yl)urea To a solution of 27a (0.85 g, 3.6 mmol) in THF (30 mL) was added CDI (2.1 mol eq, 1.24 g) and the mixture was heated at 70° C. overnight. The reaction mixture was evaporated, water was added and the aqueous phase was extracted with EtOAc (3×20 mL). The recombined organic phases were anhydrified over $Na_2SO_4$ and evaporated at reduced pressure (pale yellow oil, 1.25 g, quantitative yield). The oil obtained (0.59 g) was dissolved in DMF (20 mL) and the bicyclic amine 1a was added (0.8 mol eq, 0.21 g), then the mixture obtained was heated at 100° C. overnight. The solvent was removed at reduced pressure and the residue was purified by chromatography (100% EtOAc) to obtain the product as a white crystal solid (0.15 g, 0.4 mmol, 36% Yield). $^1$HNMR (DMSO, 400 MHz) δ 1.29 (s, 3H), 1.32 (s, 3H), 4.32 (d, 2H, J=6), 4.79 (m, 1H), 6.60 (m, 2H), 6.79-6.96 (m, 2H), 7.28 (d, 2H), 7.46 (d, 1H, J=6), 8.37 (s, 1H), 10.0 (bs, 1H), 10.60 (bs, 1H). [M$^{+1}$] 409.1 ($C_{19}H_{19}F_3N_4O_3$ requires 408.37).

Preparation of 1-[[2-isopropoxy-6-(trifluoromethyl)-3-pyridyl]methyl]-3-(2-oxo-1,3-dihydrobenzimidazol-4-yl)urea To a solution of 29a (0.42 g, 1.8 mmol) in THF (25 mL) was added CDI (2.1 mol eq, 0.61 g) and the mixture was heated at 70° C. overnight. The reaction mixture was evaporated, water was added and the aqueous phase was extracted with EtOAc (3×20 mL). The recombined organic phases were anhydrified over $Na_2SO_4$ and evaporated at reduced pressure (pale yellow oil, 0.52 g, quantitative yield). The oil obtained (0.25 g) was dissolved in DMF (15 mL) and the bicyclic amine 1a was added (0.8 mol eq, 0.09 g), then the mixture obtained was heated at 100° C. overnight. The solvent was removed at reduced pressure and the residue was purified by chromatography (100% EtOAc) to obtain the product as a pale yellow solid (0.08 g, 0.4 mmol, 27% Yield). $^1$HNMR (DMSO, 400 MHz) δ 1.33 (s, 3H), 1.36 (s, 3H), 4.28 (d, 2H, J=6), 5.28 (m, 1H), 6.64 (m, 2H), 6.87-6.93 (m, 2H), 7.46 (d, 1H, J=8), 7.78 (d, 1H), 8.41 (s, 1H), 9.99 (bs, 1H), 10.62 (bs, 1H). [M$^{+1}$] 409.7 ($C_{18}H_{18}F_3N_5O_3$ requires 409.36).

Example 68

1-[[2-isopropoxy-6-(trifluoromethyl)-3-pyridyl]methyl]-3-(2-oxo-1,3-dihydrobenzimidazol-4-yl)urea

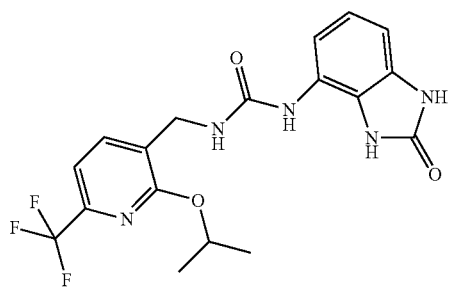 [SMILES: CC(C)Oc1nc(C(F)(F)F)ccc1CNC(=O)Nc1cccc2[nH]c(=O)[nH]c12]

Example 69

1-[[2-dimethylamino-6-(trifluoromethyl)-3-pyridyl]methyl]-3-(2-oxo-1,3-dihydrobenzimidazol-4-yl)urea

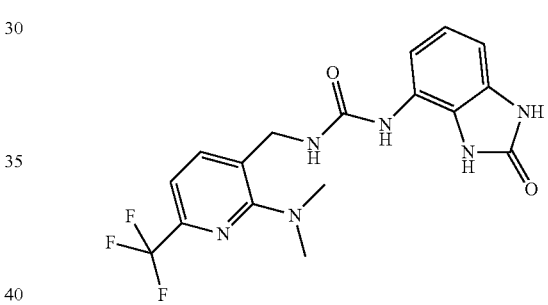

Preparation of 2-isopropoxy-6-(trifluoromethyl)pyridine-3-carbonitrile 28a (Scheme 14)

The 2-chloro-6-trifluoromethyl-nicotinonitrile (0.5 g, 2.4 mmol) was added in small portion to a mixture of NaH 60% (4 mol eq) in isopropanol (20 mL). The reaction mixture was heated at 50° C. overnight. The solvent was distilled and water was added to the residue. The aqueous solution was extracted with EtOAc (3×25 mL) and the organic phases were evaporated at reduced pressure to give e as a yellow solid (0.45 g, 82% Yield, 1.96 mmol). $^1$HNMR (DMSO, 200 MHz) δ 1.35 (s, 3H), 1.38 (s, 3H), 5.33 (m, 1H), 7.55 (d, 1H, J=6), 8.26 (d, 1H, J=6).

Preparation of [2-isopropoxy-6-(trifluoromethyl)-3-pyridyl]methanamine 29a

The nitrile 28a (0.45 g, 1.96 mmol)) was added in small portion to a mixture of LiAlH$_4$ (0.15 g, 2 mol eq) in Et$_2$O (30 mL) stirred at 0° C. Then the mixture was stirred at room temperature overnight. The excess of LiAlH$_4$ was decomposed by water addition at 0° C., the solid formed was filtered, washed with Et$_2$O and the filtrate was separated. The organic phase was anhydrified over Na$_2$SO$_4$ and evaporated to dryness to obtain 29a as yellow oil (0.42 g, 1.79 mmol, 94% Yield) used for the next reaction without further purification.

Preparation of 2-dimethylamino-6-(trifluoromethyl)pyridine-3-carbonitrile 28d (Scheme 14)

To 2-chloro-6-(trifluoromethyl)nicotinonitrile (0.8 g, 3.8 mmol) was added hexamethylphosphoramide (6 mol eq, 4.16 mL) and the mixture was heated at 150° C. for 48 h. The reaction mixture was cooled at room temperature, water and brine were added and the mixture was extracted with EtOAc (4×35 mL). The recombined organic phases were dried over sodium sulfate and evaporated to dryness to obtain 28d as yellow oil (1.01 g, quantitative yield). $^1$HNMR (DMSO, 200 MHz) δ 1.33 (s, 3H), 1.38 (s, 3H), 7.41 (d, 1H, J=6), 7.55 (d, 1H, J=6).

Preparation of 3-(aminomethyl)-N,N-dimethyl-6-(trifluoromethyl)pyridin-2-amine 29d The nitrile 28d (1 g, 4.6 mmol)) was added in small portion to a mixture of LiAlH$_4$ (0.5 g, 2 mol eq) in Et$_2$O (30 mL) stirred at 0° C. Then the mixture was stirred at room temperature overnight. The excess of LiAlH$_4$ was decomposed by water addition at 0° C., the solid formed was filtered, washed with Et$_2$O and the filtrate was separated. The organic phase was anhydrified over Na$_2$SO$_4$ and evaporated to dryness to obtain 29d as yellow oil (0.78 g, 3.5 mmol, 76% Yield) used without further purifications.

Preparation of 1-[[2-dimethylamino-6-(trifluoromethyl)-3-pyridyl]methyl]-3-(2-oxo-1,3-dihydrobenzimidazol-4-yl)urea To a solution of 29d (0.78 g, 3.5 mmol) in THF (35 mL) was added CDI (2.1 mol eq, 1.21 g) and the mixture was heated at 70° C. overnight. The reaction mixture was evaporated, water was added and the aqueous phase was extracted with EtOAc (3×25 mL). The recombined organic phases were anhydrified over $Na_2SO_4$ and evaporated at reduced pressure (pale orange oil, quantitative yield). The oil obtained (0.7 g, 2.4 mmol) was dissolved in DMF (30 mL) and the bicyclic amine 1a was added (0.8 mol eq, 0.26 g), then the mixture obtained was heated at 100° C. overnight. The solvent was removed at reduced pressure and the residue was purified by chromatography (9.5:0.5 EtOAc:MeOH) to obtain the product as a pale yellow solid (0.08 g, 0.2 mmol, 20% Yield). $^1$HNMR (DMSO, 400 MHz) δ 2.84 (s, 6H), 4.38 (d, 2H, J=6), 6.60 (dd, 1H), 6.79 (m, 2H), 6.99 (m, 1H), 7.37 (d, 1H, J=6), 7.84 (d, 1H, J=8), 8.37 (s, 1H), 10.0 (bs, 1H), 10.60 (bs, 1H). [$M^{+1}$] 394.9 ($C_{17}H_{17}F_3N_6O_2$ requires 394.35).

Example 70

1-[(4-tert-butylphenyl)methyl]-3-(2-oxo-1,3-dihydrobenzimidazol-4-yl)urea

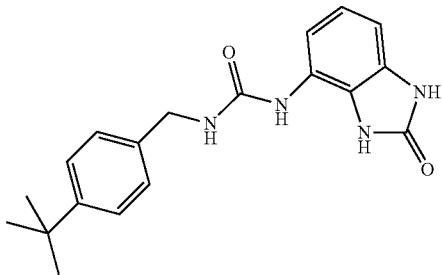 [SMILES: CC(C)(C)c1ccc(CNC(=O)Nc2cccc3[nH]c(=O)[nH]c23)cc1]

To a solution of 4-tert-butylbenzylamine (2 mL, 11.36 mmol) in THF (30 mL) was added CDI (2.1 mol eq, 3.86 g) and the mixture was heated at 70° C. overnight. The reaction mixture was evaporated, water was added and the aqueous phase was extracted with EtOAc (3×30 mL). The recombined organic phases were anhydrified over $Na_2SO_4$ and evaporated at reduced pressure (pale yellow oil, quantitative yield). The oil obtained (1.6 g, 6.2 mmol)) was dissolved in DMF (25 mL) and the bicyclic amine 1a was added (0.8 mol eq, 0.74 g), then the mixture obtained was heated at 100° C. overnight. The solvent was removed at reduced pressure and the residue was purified by crystallization from MeOH to obtain the product as a white solid (0.54 g, 1.59 mmol, 26% Yield). $^1$HNMR (DMSO, 400 MHz) δ 1.26 (s, 9H), 4.28 (d, 2H, J=6), 6.34 (dd, 1H), 6.36 (t, 1H), 6.83-6.91 (m, 2H), 7.26 (d, 2H, J=8), 7.37 (d, 2H, J=8), 8.20 (s, 1H9, 9.89 (bs, 1H), 10.61 (bs, 1H). [$M^{+1}$] 338.82 ($C_{19}H_{22}N_4O_2$ requires 338.40).

Example 71

1-(2-oxo-1,3-dihydrobenzimidazol-4-yl)-3-[[2-(1-piperidyl)-6-(trifluoromethyl)-3-pyridyl]methyl]urea

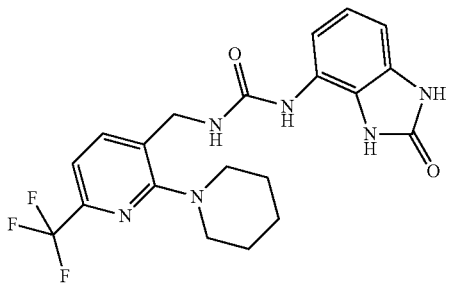 [SMILES: O=C(NCc1ccc(C(F)(F)F)nc1N1CCCCC1)Nc1cccc2[nH]c(=O)[nH]c12]

Preparation of 2-(1-piperidyl)-6-(trifluoromethyl)-pyridine-3-carbonitrile 28f (Scheme 14)

To 2-chloro-6-trifluoromethyl-nicotinonitrile (0.5 g, 2.42 mmol) in EtOH abs (20 mL) was added piperidine (4 mol eq, 1 mL) and the mixture was heated at 90° C. for 3 h. The mixture was concentrated, water was added and the mixture was extracted with EtOAc (3×20 mL). The recombined organic phases were anhydrified and evaporated to dryness to obtain 2-(1-piperidyl)-6-trifluoromethyl)-pyridine-3-carbonitrile as pale yellow oil (0.67 g, quantitative yield). $^1$HNMR (DMSO, 200 MHz) δ 3.33 (m, 4H), 3.56 (m, 4H), 7.25 (d, 1H), 7.36 (d, 1H, J=6).

Preparation of 2-(1-piperidyl)-6-(trifluoromethyl)-3-aminomethyl-pyridine 29f

The nitrile 28f (0.67 g, 2.66 mmol) solubilized in $Et_2O$ (20 mL) was added in small portion to a mixture of $LiAlH_4$ (0.202 g, 2 mol eq) in $Et_2O$ (25 mL) stirred at 0° C. Then the mixture was stirred at room temperature overnight. The excess of $LiAlH_4$ was decomposed by water addition at 0° C., the solid formed was filtered, washed with $Et_2O$ and the filtrate was separated. The organic phase was anhydrified over $Na_2SO_4$ and evaporated to dryness to obtain 29f as yellow oil (0.48 g, 1.85 mmol, 69% Yield) used without further purifications.

Preparation of 1-(2-oxo-1,3-dihydrobenzimidazol-4-yl)-3-[[2-piperidyl-1-yl-6-(trifluoromethyl)-3-pyridyl]methyl]urea To a solution of 29f (0.48 g, 1.85 mmol) in THF (20 mL) was added CDI (2.1 mol eq, 0.63 g) and the mixture was heated for 5 h. The reaction mixture was evaporated, water was added and the aqueous phase was extracted with EtOAc (3×20 mL). The recombined organic phases were anhydrified over $Na_2SO_4$ and evaporated at reduced pressure. The oil obtained (0.78 g, quantitative yield) was dissolved in DMF (20 mL) and the bicyclic amine 1a was added (0.8 mol eq, 0.26 g), then the mixture obtained was heated at 100° C. overnight. The solvent was removed at reduced pressure and the residue was purified by chromatography (9.5:0.5 EtoAc:MeOH) to obtain the product as a pale yellow solid (0.14 g, 0.32 mmol, 15% Yield). $^1$HNMR (DMSO, 400 MHz) δ 1.63 (m, 6H), 3.09 (m, 4H), 4.36 (d, 2H, J=6), 6.61 (d, 1H, J=8), 6.84 (t, 2H), 6.95 (d, 1H, J=6), 7.42 (d, 1H, J=8), 7.87 (d, 1H, J=6), 8.37 (s, 1H), 10.01 (bs, 1H), 10.59 (bs, 1H). [M$^{+1}$] 434.91 ($C_{20}H_{21}F_3N_6O_2$ requires 434.41).

Example 72

1-[[2-(2-dimethylaminoethoxy)-6-(trifluoromethyl)-3-pyridyl]methyl]-3-(2-oxo-1,3-dihydrobenzimidazol-4-yl)urea

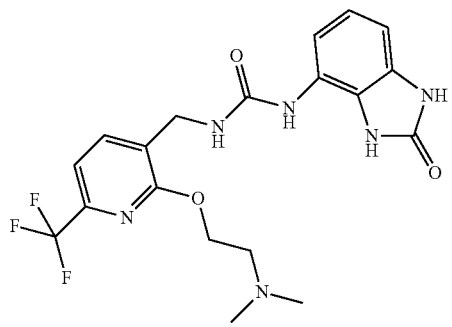 [SMILES: CN(C)CCOc1nc(C(F)(F)F)ccc1CNC(=O)Nc1cccc2[nH]c(=O)[nH]c12]

Preparation of 2-(2-dimethylaminoethoxy)-6-(trifluoromethyl)pyridine-3-carbonitrile 28b (Scheme 14)

To N,N-dimethylaminoethanol (25 mL) at 0° C. was added in small portion NaH 60% (4 mol eq, 0.465 g, 11.62 mmol) and after 10 min 2-chloro-6-trifluoromethyl-nicotinonitrile (0.6 g, 2.90 mmol) was slowly added. The mixture was heated at 65° C. for 4 h. Then the solvent was removed at reduced pressure, water was added and the aqueous phase was extracted with EtOAc (3×30 mL). The recombined organic phases were washed with brine, anhydrified over $Na_2SO_4$ and evaporated at reduced pressure to obtain a pale yellow oil (0.69 g, 2.66 mmol, 92% Yield) used for the next step of reaction without further purification.

Preparation of 2-[[3-(aminomethyl)-6-(trifluoromethyl)-2-pyridyl]oxy]-N,N-dimethyl-ethanamine 29b The nitrile 28b (2.66 mmol) was dissolved in EtOH abs (30 mL), C/Pd 10% (0.25 mg) was added and the mixture was hydrogenated at 70 psi overnight. The reaction mixture was filtered through a celite pad and the filtrate was evaporated at reduced pressure to give 29b as brown oil (0.6 g, 2.28 mmol, 86% Yield) $^1$HNMR (DMSO, 200 MHz) δ 2.20 (s, 6H), 2.65 (t, 2H), 3.23 (m, 2H), 4.01 (m, 2H), 7.60 (d, 1H), 7.99 (bs, 2H), 8.38 (d, 1H, J=8).

Preparation of 1-[[2-(2-dimethylaminoethoxy)-6-(trifluoromethyl)-3-pyridyl]methyl]-3-(2-oxo-1,3-dihydrobenzimidazol-4-yl)urea To a solution of 29b (0.6 g, 2.28 mmol) in THF (20 mL) was added CDI (2.1 mol eq, 0.78 g) and the mixture was heated at 70° C. for 6 h. The reaction mixture was evaporated, water was added and the aqueous phase was extracted with EtOAc (3×25 mL). The recombined organic phases were anhydrified over $Na_2SO_4$ and evaporated at reduced pressure (yellow oil, 0.72 g, 88% yield). The oil obtained was dissolved in DMF (20 mL) and the bicyclic amine 1a was added (0.8 mol eq, 0.24 g), then the mixture obtained was heated at 100° C. overnight. The solvent was removed at reduced pressure and the residue was purified by chromatography (8:2 EtOAc: MeOH) to obtain the product as a pale yellow solid (0.088 g, 0.158 mmol, 10% Yield). $^1$HNMR (DMSO, 400 MHz) δ 2.27 (s, 6H), 2.73 (t, 2H), 4.25 (d, 2H, J=6), 4.46 (t, 2H), 6.60 (d, 1H), 6.83 (m, 2H), 7.01 (d, 1H), 7.43 (d, 1H), 7.80 (d, 1H), 8.60 (s, 1H), 10.02 (bs, 1H), 10.62 (bs, 1H). [M$^{+1}$] 439.02 ($C_{19}H_{21}F_3N_6O_3$ requires 438.40).

Example 73

1-[[2-(2-dimethylaminoethoxy)-4-(trifluoromethyl) phenyl]methyl]-3-(2-oxo-1,3-dihydrobenzimidazol-4-yl)urea (Scheme 13)

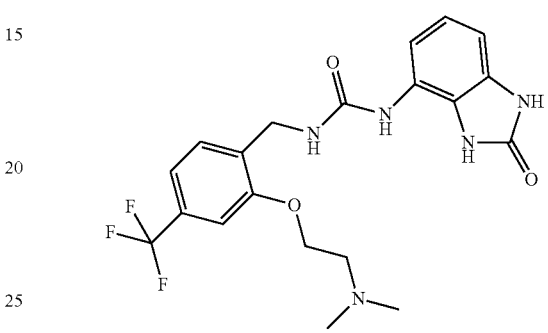

Preparation of 2-(2-dimethylaminoethoxy)-4-(trifluoromethyl)benzonitrile 26b

To N,N-dimethylaminoethanol (15 mL) cooled at 0° C. was added NaH 60% (1.15 g, 4 mol eq) and then 2-fluoro-4-trifluoromethyl-benzonitrile (1 mL, 7.18 mmol). The mixture was heated at 60° C. for 4 h then the solvent was removed at reduced pressure and water was added to the residue. The aqueous phase was extracted with EtOAc (3×30 mL), the organic phases were dried over sodium sulfate and evaporated to dryness to give 26b as pale yellow oil (2.1 g, quantitative yield). $^1$HNMR (DMSO, 200 MHz) δ 1.21 (s, 3H), 1.31 (s, 3H), 2.21 (t, 2H, J=8), 2.48 (t, 2H, J=8), 6.54 (dd, 1H, J=2), 6.82 (m, 2H).

Preparation of 2-[2-(aminomethyl)-5-(trifluoromethyl)phenoxy]-N,N-dimethyl-ethanamine 27b The nitrile 26b (2.15 g, 8.33 mmol) solubilized in $Et_2O$ (20 mL) was added in small portion to a mixture of $LiAlH_4$ (0.63 g, 2 mol eq) in $Et_2O$ (25 mL) stirred at 0° C. Then the mixture was stirred at room temperature overnight. The excess of $LiAlH_4$ was decomposed by water addition at 0° C., the solid formed was filtered, washed with $Et_2O$ and the filtrate was separated. The organic phase was anhydrified over $Na_2SO_4$ and evaporated to dryness to obtain 27b as yellow oil (1.48 g, 5.64 mmol, 67% Yield) used without further purifications.

Preparation of 1-[[2-(2-dimethylaminoethoxy)-4-(trifluoromethyl)phenyl]methyl]-3-(2-oxo-1,3-dihydrobenzimidazol-4-yl)urea To a solution of 27b (1.48 g, 5.64 mmol) in THF (25 mL) was added CDI (2.1 mol eq, 1.92 g) and the mixture was heated at 70° C. overnight. The reaction mixture was evaporated, water was added and the aqueous phase was extracted with EtOAc (3×30 mL). The recombined organic phases were anhydrified over $Na_2SO_4$ and evaporated at reduced pressure (pale yellow oil, 1.91 g, 95% yield). The oil obtained (0.95 g, 2.68 mmol) was dissolved in DMF (20 mL) and the bicyclic amine 1a was added (0.8 mol eq, 0.32 g), then the mixture obtained was heated at 100° C. overnight. The solvent was removed at reduced pressure and the residue was purified by chromatography (8:2 EtOAc:MeOH) to obtain the product as a white solid (0.17 g, 20% Yield). $^1$HNMR (DMSO, 400 MHz) δ 2.24 (s, 6H), 2.68 (t, 2H, J=6), 4.19 (t, 2H, J=6), 4.32 (d, 2H, J=6), 6.60 (m, 2H), 6.67 (t, 1H), 6.93 (d, 1H, J=4), 7.28 (m, 2H), 7.43 (d, 1H), 8.40 (s, 1H), 9.98 (s, 1H), 10.60 (s, 1H). [M$^{+1}$] 438.01 ($C_{20}H_{22}F_3N_5O_3$ requires 437.42).

Example 74

1-[(4-tert-butyl-2-chloro-phenyl)methyl]-3-(2-oxo-1,3-dihydrobenzimidazol-4-yl)urea

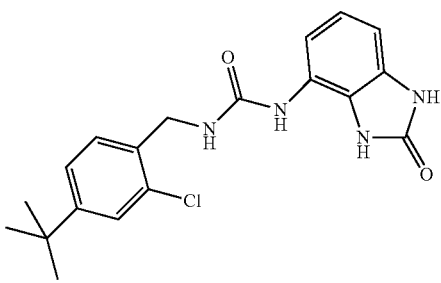 [SMILES: CC(C)(C)c1ccc(CNC(=O)Nc2cccc3[nH]c(=O)[nH]c23)c(Cl)c1]

Preparation of 4-tert-butyl-2-chloro-benzonitrile 9 (Multi-steps reaction) (Scheme 4)

To a solution of 4-tert-butylacetanilide 7 (5 g, 26.1 mmol) in DMF (30 mL) was added at 0° C. NCS (1.5 mol eq, 5.23 g) and the mixture was stirred at room temperature overnight. Water was added and the solid formed was filtered off to furnish 8 as pale yellow solid (quantitative yield, 5.8 g).

The acetyl 8 was deprotected by treatment with aqueous HCl 20% overnight to furnish the aniline derivative as red oil (75% Yield).

The aniline derivative of 8 (5 g, 5.43 mmol) was solubilized in 10:6 HOAc:water (35 mL). To this solution was added conc. $H_2SO_4$ (4.5 mL) and this solution was cooled at 10° C. and treated with a solution of $NaNO_2$ (2.1 g, 1.1 mol eq) in water (5 mL). After this addition was completed the reaction mixture was stirred at 10° C. for 1 h. During this time a solution of tetra-butylammonium cyanide (36.4 g, 5 mol eq) in water (25 mL) was added to a cold stirred solution of $CuSO_4 \cdot 5H_2O$ (8.2 g, 1.2 mol eq) in water (25 mL). To this mixture was added $NaHCO_3$ (18.15 g) and toluene (50 mL) and the resulting mixture was heated at 55° C. to dissolve the solid formed. To this solution was added drop wise the solution of the diazonium salt under $N_2$ at 55° C. The reaction mixture was kept for 30 min. at 55° C. and then was cooled and extracted three times with toluene. The combined organic extracts were washed with 1N NaOH and brine, then dried and evaporated to dryness to obtain a red-brown oil purified by chromatography (9.5:0.5 petroleum ether:EtOAc) to furnish the nitrile 9 as a red oil (2.2 g, 43% Yield). $^1$HNMR (DMSO, 200 MHz) δ 1.28 (s, 9H), 7.54 (dd, 1H, J=2), 7.71 (d, 1H, J=2), 7.96 (d, 1H, J=8).

Preparation of (4-tert-butyl-2-chloro-phenyl)-methanamine 11c

The nitrile 9 (0.97 g, 4 mmol) solubilized in Et$_2$O (30 mL) was added in small portion to a mixture of LiAlH$_4$ (0.3 g, 2 mol eq) in Et$_2$O (25 mL) stirred at 0° C. Then the mixture was stirred at room temperature overnight. The excess of LiAlH$_4$ was decomposed by water addition at 0° C., the solid formed was filtered, washed with Et$_2$O and the filtrate was separated. The organic phase was anhydrified over Na$_2$SO$_4$ and evaporated to dryness to obtain 11c as orange oil (1 g, quantitative Yield), used for the next step of reaction without further purification.

Preparation of 1-[(4-tert-butyl-2-chloro-phenyl)methyl]-3-(2-oxo-1,3-dihydrobenzimidazol-4-yl)urea To a solution of 11c (1 g, 4.6 mmol) in THF (40 mL) was added CDI (2.1 mol eq, 1.4 g) and the mixture was heated at 70° C. overnight. The reaction mixture was evaporated, water was added and the aqueous phase was extracted with EtOAc (3×30 mL). The recombined organic phases were anhydrified over Na$_2$SO$_4$ and evaporated at reduced pressure (red oil, 1.36 g, 98% yield). The oil obtained (1.36 g, 3.99 mmol) was dissolved in DMF (20 mL) and the bicyclic amine 1a was added (0.8 mol eq, 0.47 g), then the mixture obtained was heated at 100° C. overnight. The solvent was removed at reduced pressure and the residue was purified by chromatography (100% EtOAc) to obtain the product as a white solid (0.29 g, 21% Yield). $^1$HNMR (DMSO, 200 MHz) δ 1.26 (s, 9H), 4.35 (d, 2H, J=6), 6.64 (d, 1H, J=8), 6.87 (m, 3H), 7.40 (m, 3H), 8.31 (s, 1H), 9.94 (bs, 1H), 10.59 (bs, 1H). [M$^{+1}$] 373.05 ($C_{19}H_{21}ClN_4O_2$ requires 372.85).

Example 75

1-[(4-tert-butyl-2-pyrrolidin-1-yl-phenyl)methyl]-3-(2-oxo-1,3-dihydrobenzimidazol-4-yl)urea

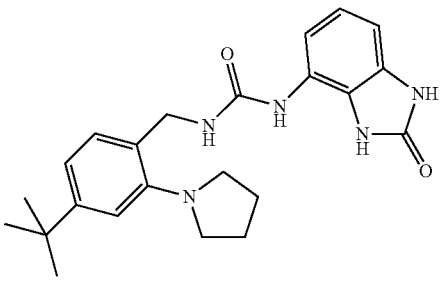 [SMILES: CC(C)(C)c1ccc(CNC(=O)Nc2cccc3[nH]c(=O)[nH]c23)c(N2CCCC2)c1]

Preparation of 4-tert-butyl-2-pyrrolidin-1-yl-benzonitrile 10a (Multi-steps reaction) (Scheme 4)

The nitrile 9 (2.2 g, 11.3 mmol) was heated in a steel-bomb with pyrrolidine (3.75 mL, 4 mol eq) at 200° C. for 12 h. The reaction mixture was concentrated, water and brine was added and the mixture was extracted three times with EtOAc. The recombined organic phases were dried under sodium sulfate and evaporated to dryness to furnish 10a as a red oil (2.6 g, quantitative yield), used for the next step of reaction without further purifications.

Preparation of (4-tert-butyl-2-pyrrolidin-1-yl-phenyl)methanamine 11a

The nitrile 10a (2.6 g, 11.4 mmol) solubilized in Et$_2$O (30 mL) was added in small portion to a mixture of LiAlH$_4$ (0.87 g, 2 mol eq) in Et$_2$O (25 mL) stirred at 0° C. Then the mixture was stirred at room temperature overnight. The excess of LiAlH$_4$ was decomposed by water addition at 0° C., the solid formed was filtered, washed with Et₂O and the filtrate was separated. The organic phase was anhydrified over Na₂SO₄ and evaporated to dryness to obtain 11a as orange oil (2.7 g, quantitative Yield). ¹HNMR (DMSO, 200 MHz) δ 1.25 (s, 9H), 1.82 (m, 4H), 2.49 (m, 4H), 3.09 (m, 2H), 3.67 (m, 2H), 6.86 (dd, 1H), 7.35 (m, 2H).

Preparation of 1-[(4-tert-butyl-2-pyrrolidin-1-yl-phenyl)methyl]-3-(2-oxo-1,3-dihydrobenzimidazol-4-yl)urea To a solution of 11a (2.7 g, 11.6 mmol) in THF (40 mL) was added CDI (2.1 mol eq, 3.96 g) and the mixture was heated at 70° C. overnight. The reaction mixture was evaporated, water was added and the aqueous phase was extracted with EtOAc (3×30 mL). The recombined organic phases were anhydrified over Na₂SO₄ and evaporated at reduced pressure (red oil, 3.6 g, 95% yield). The oil obtained (1.8 g, 5.52 mmol) was dissolved in DMF (20 mL) and the bicyclic amine 1a was added (0.8 mol eq, 0.65 g), then the mixture obtained was heated at 100° C. overnight. The solvent was removed at reduced pressure and the residue was purified by chromatography (100% EtOAc) to obtain the product as a white solid (0.17 g, 20% Yield). ¹HNMR (DMSO, 200 MHz) δ 1.26 (s, 9H), 1.88 (m, 4H), 3.13 (m, 4H), 4.31 (d, 2H, J=6), 6.52 (bt, 1H), 6.59 (d, 1H, J=8), 6.93 (m, 4H), 7.19 (d, 1H, J=8), 8.26 (s, 1H), 9.93 (bs, 1H), 10.59 (bs, 1H). [M⁺¹] 408.03 (C₂₃H₂₉N₅O₂ requires 407.51).

Example 76

1-(3-oxo-4H-1,4-benzoxazin-8-yl)-3-[[5-(trifluoromethyl)-2-furyl]methyl]urea

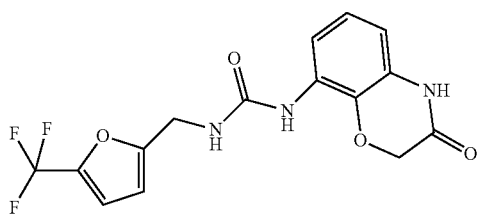 [SMILES: O=C1COc2c(cccc2NC(=O)NCc2ccc(C(F)(F)F)o2)N1]

Preparation of 1-(3-oxo-4H-1,4-benzoxazin-8-yl)-3-[[5-(trifluoromethyl)-2-furyl]methyl]urea To a solution of [5-(trifluoromethyl)-2-furyl]methanamine (0.48 g, 2.91 mmol) in THF (20 mL) was added CDI (2.1 mol eq, 0.99 g) and the mixture was heated at 70° C. overnight. The reaction mixture was evaporated, water was added and the aqueous phase was extracted with EtOAc (3×25 mL). The recombined organic phases were anhydrified over Na₂SO₄ and evaporated at reduced pressure (yellow oil, 1.68 g, quantitative yield). The oil obtained was dissolved in DMF (20 mL) and the bicyclic amine 1f was added (0.8 mol eq, 0.57 g), then the mixture obtained was heated at 100° C. overnight. The solvent was removed at reduced pressure and the residue was purified by crystallization from a mixture of MeOH/EtOAc to afford the product as a pale yellow solid (0.088 g, 10% Yield). ¹HNMR (DMSO, 400 MHz) δ 4.37 (d, 2H, J=6), 4.60 (s, 2H), 6.46 (m, 2H), 6.77 (t, 1H, J=8), 7.16 (m, 1H), 7.37 (t, 1H), 7.72 (dd, 1H, J=2), 8.16 (s, 1H), 10.64 (bs, 1H).

Example 77

1-(3-oxo-4H-1,4-benzoxazin-8-yl)-3-[[6-(trifluoromethyl)-3-pyridyl]methyl]urea

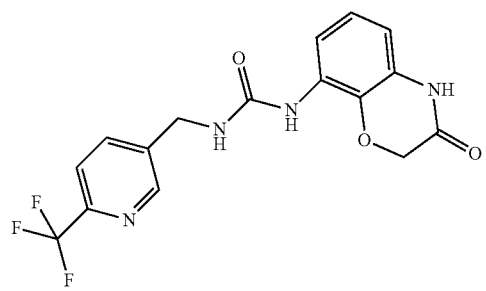 [SMILES: O=C1COc2c(cccc2NC(=O)NCc2ccc(C(F)(F)F)nc2)N1]

To a solution of 3-aminomethyl-6-trifluoromethylpyridine (1 g, 4.7 mmol) in THF (30 mL) was added CDI (2.1 mol eq) and the mixture was heated at 70° C. overnight. The reaction mixture was evaporated, water was added and the aqueous phase was extracted with EtOAc (3×20 mL). The recombined organic phases were anhydrified over Na₂SO₄ and evaporated at reduced pressure. The oil obtained (0.8 g, 2.96 mmol) was dissolved in DMF (20 mL) and the bicyclic amine 1f was added (0.8 mol eq, 0.47 g), then the mixture obtained was heated at 100° C. overnight. The solvent was removed at reduced pressure and the residue was purified by chromatography (100% EtOAc) to obtain the product as a pale yellow solid (0.37 g, 42% Yield). ¹HNMR (DMSO, 200 MHz) δ 4.39 (d, 2H, J=6), 4.61 (s, 2H), 6.46 (dd, 1H, J=2), 6.81 (t, 1H, J=8), 7.43 (t, 1H), 7.68 (dd, 1H, J=2), 7.90 (m, 2H), 8.18 (s, 1H), 8.69 (s, 1H), 10.66 (s, 1H). [M⁺¹] 355.88 (C₁₅H₁₃F₃N₃O₃ requires 355.27).

Example 78

1-(3-oxo-4H-1,4-benzoxazin-8-yl)-3-[[2-(1-piperidyl)-6-(trifluoromethyl)-3-pyridyl]methyl]urea (Scheme 14)

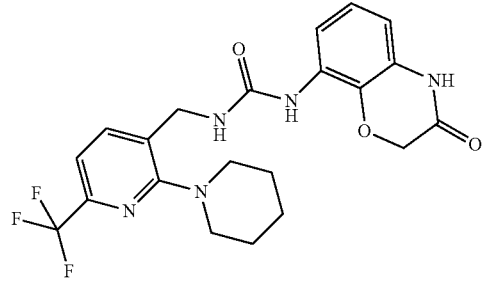 [SMILES: O=C1COc2c(cccc2NC(=O)NCc2ccc(C(F)(F)F)nc2N2CCCCC2)N1]

To a solution of 29f (0.48 g, 1.85 mmol) in THF (20 mL) was added CDI (2.1 mol eq, 0.63 g) and the mixture was heated for 5 h. The reaction mixture was evaporated, water was added and the aqueous phase was extracted with EtOAc (3×20 mL). The recombined organic phases were anhydrified over Na₂SO₄ and evaporated at reduced pressure. The oil obtained (0.78 g, quantitative yield) was dissolved in DMF (20 mL) and the bicyclic amine 1f was added (0.8 mol eq, 0.23 g), then the mixture obtained was heated at 100° C. overnight. The solvent was removed at reduced pressure and the residue was purified by chromatography (1:1 EtOAc:petroleum ether) to obtain the product as a pale yellow solid (0.067 g, 13%

Yield). ¹HNMR (DMSO, 400 MHz) δ 1.62 (m, 6H), 3.09 (m, 4H), 4.33 (d, 2H, J=6), 4.62 (s, 2H), 6.46 (dd, 1H, J=2), 6.81 (t, 1H, J=8), 7.42 (bt, 1H), 4.46 (d, 1H, J=8), 7.74 (m, 2H), 8.20 (s, 1H), 10.66 (s, 1H). [M⁺¹] 450.02 (C₂₁H₂₂F₃N₅O₃ requires 449.43).

Example 79

1-(3-oxo-4H-1,4-benzoxazin-8-yl)-3-(p-tolylmethyl)urea

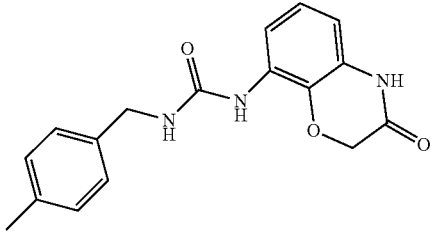 [SMILES: Cc1ccc(CNC(=O)Nc2cccc3c2OCC(=O)N3)cc1]

To a solution of 4-methylbenzylamine (1.5 mL, 11.8 mmol) in THF (30 mL) was added CDI (2.1 mol eq, 3.8 g) and the mixture was heated at 70° C. overnight. The reaction mixture was evaporated, water was added and the aqueous phase was extracted with EtOAc (3×30 mL). The recombined organic phases were anhydrified over Na₂SO₄ and evaporated at reduced pressure to give a white solid (11.78 mmol, 2.53 g, quantitative yield). The solid obtained (0.83 g, 3.88 mmol) was dissolved in DMF (20 mL) and the bicyclic amine 1f was added (0.8 mol eq, 0.62 g), then the mixture obtained was heated at 100° C. overnight. The solvent was removed at reduced pressure and the residue was purified by crystallization from hot MeOH to give the product as pale yellow solid (0.078 g, 8% Yield). ¹HNMR (DMSO, 200 MHz) δ 2.27 (s, 3H), 4.24 (d, 2H, J=6), 4.59 (s, 2H), 6.28 (t, 1H), 4.47 (dd, 1H), 6.80 (t, 1H, J=8), 7.11-7.21 (m, 4H), 7.77 (dd, 1H, J=2), 8.07 (s, 1H), 10.63 (bs, 1H). [M⁺¹] 311.99 (C₁₇H₁₇N₃O₃ requires 311.34).

Example 80

1-[[6-methyl-2-(1-piperidyl)-3-pyridyl]methyl]-3-(3-oxo-4H-1,4-benzoxazin-8-yl)urea (Scheme 16)

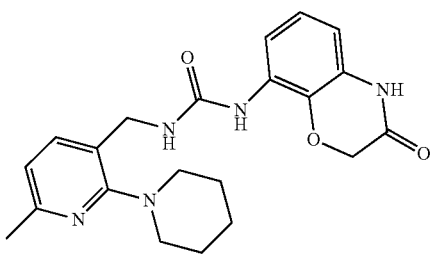 [SMILES: Cc1ccc(CNC(=O)Nc2cccc3c2OCC(=O)N3)c(N2CCCCC2)n1]

To a solution of 33b (1.06 g, 5.18 mmol) in THF (20 mL) was added CDI (2.1 mol eq, 1.76 g) and the mixture was heated for 6 h. The reaction mixture was evaporated, water was added and the aqueous phase was extracted with EtOAc (3×20 mL). The recombined organic phases were anhydrified over Na₂SO₄ and evaporated at reduced pressure to give an oil (1.04 g, 3.36 mmol). One portion (0.5 g, 1.67 mmol) was dissolved in DMF (20 mL) and the bicyclic amine 1f was added (0.8 mol eq, 0.25 g), then the mixture obtained was heated at 100° C. overnight. The solvent was removed at reduced pressure and the residue was purified by chromatography (1:1 EtOAc:petroleum ether) to obtain the product as a white solid (0.13 g, 28% Yield). ¹HNMR (DMSO, 400 MHz) δ 1.63 (m, 6H), 2.48 (s, 3H), 2.94 (m, 4H), 4.24 (d, 2H, J=6), 4.61 (s, 2H), 6.45 (dd, 1H, J=2), 6.83 (m, 2H), 7.21 (bt, 1H), 7.48 (d, 1H, J=8), 7.76 (dd, 1H, J=2), 8.12 (s, 1H), 10.65 (s, 1H). [M⁺¹] 396.03 (C₂₁H₂₅N₅O₃ requires 395.45).

Example 81

1-[[2-isopropoxy-4-(trifluoromethyl)phenyl]methyl]-3-(3-oxo-4H-1,4-benzoxazin-8-yl)urea (Scheme 13)

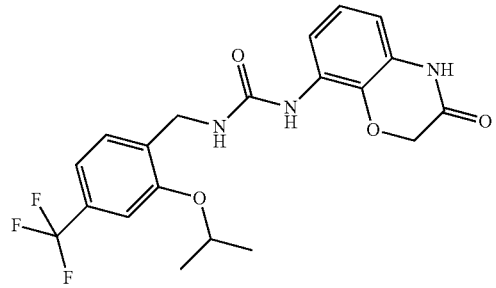 [SMILES: CC(C)Oc1cc(C(F)(F)F)ccc1CNC(=O)Nc1cccc2c1OCC(=O)N2]

To a solution of 27a (0.85 g, 3.6 mmol) in THF (30 mL) was added CDI (2.1 mol eq, 1.24 g) and the mixture was heated at 70° C. overnight. The reaction mixture was evaporated, water was added and the aqueous phase was extracted with EtOAc (3×20 mL). The recombined organic phases were anhydrified over Na₂SO₄ and evaporated at reduced pressure (pale yellow oil, 1.25 g, quantitative yield). The oil obtained (0.6 g, 1.82 mmol) was dissolved in DMF (20 mL) and the bicyclic amine 1f was added (0.8 mol eq, 0.29 g), then the mixture obtained was heated at 100° C. overnight. The solvent was removed at reduced pressure and the residue was purified by chromatography (1:1 EtOAc:petroleum ether) to obtain the product as a white solid (0.121 g, 0.29 mmol, 16% Yield). ¹HNMR (DMSO, 400 MHz) δ 1.29 (s, 3H), 1.32 (s, 3H), 4.28 (d, 2H, J=6), 4.62 (s, 2H), 4.79 (m, 1H), 6.49 (dd, 1H, J=2), 6.80 (t, 1H, J=8), 7.25 (m, 4H), 7.71 (dd, 1H), 8.21 (s, 1H), 10.65 (s, 1H). [M⁺¹] 423.97 (C₂₀H₂₀F₃N₃O₄ requires 423.38).

Example 82

1-[[2-methoxy-6-(trifluoromethyl)-3-pyridyl]methyl]-3-(3-oxo-4H-1,4-benzoxazin-8-yl)urea (Scheme 14)

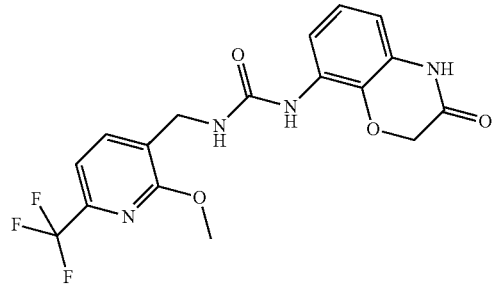 [SMILES: COc1nc(C(F)(F)F)ccc1CNC(=O)Nc1cccc2c1OCC(=O)N2]

Preparation of 2-methoxy-6-(trifluoromethyl)pyridine-3-carbonitrile 28c

To 2-chloro-6-trifluoromethyl-nicotinonitrile (0.5 g, 2.4 mmol) in methanol (30 mL) was added sodium methylate in small portion (2 mol eq, 0.26 g). The reaction mixture was heated at 60° C. overnight. The solvent was distilled under reduced pressure and water was added to the residue. The aqueous solution was extracted with EtOAc (3×25 mL) and the organic phases were evaporated at reduced pressure to give 28c as a pale yellow oil (0.48 g, 2.33 mmol, 97% Yield). $^1$HNMR (DMSO, 200 MHz) δ 4.04 (s, 3H), 7.71 (d, 1H, J=6), 8.59 (d, 1H, J=6).

Preparation of [2-methoxy-6-(trifluoromethyl)-3-pyridyl]methanamine 29c

The nitrile 28c (0.48 g, 2.33 mmol) was solubilized in MeOH (30 mL) and to the solution was added Pd/C 10% (0.3 g). The mixture was hydrogenated at 70 psi overnight. The reaction mixture was filtered through a celite pad, the filtrate was evaporated at reduce pressure to furnish 29c as yellow oil (0.38 g, 1.84 mmol, 79% Yield) used without further purification.

Preparation of 1-[[2-methoxy-6-(trifluoromethyl)-3-pyridyl]methyl]-3-(3-oxo-4H-1,4-benzoxazin-8-yl)urea To a solution of 29c (0.38 g, 1.84 mmol) in THF (15 mL) was added CDI (2.1 mol eq, 0.63 g) and the mixture was heated at 70° C. overnight. The reaction mixture was evaporated, water was added and the aqueous phase was extracted with EtOAc (3×25 mL). The recombined organic phases were anhydrified over Na$_2$SO$_4$ and evaporated at reduced pressure (yellow oil, 0.62 g, quantitative yield). The oil obtained was dissolved in DMF (20 mL) and the bicyclic amine 1f was added (0.8 mol eq, 0.21 g), then the mixture obtained was heated at 100° C. overnight. The solvent was removed at reduced pressure and the residue was purified by chromatography (1:1 EtOAc:petroleum ether) to afford the product as a white solid (0.1 g, 14% Yield). $^1$HNMR (DMSO, 400 MHz) δ 3.96 (s, 3H), 4.29 (d, 2H, J=6), 4.62 (s, 2H), 6.46 (dd, 1H, J=2), 6.80 (t, 1H, J=8), 7.34 (bt, 1H), 7.51 (d, 1H, J=8), 7.72 (m, 2H), 8.24 (s, 1H), 10.66 (s, 1H). [M$^{+1}$] 396.99 (C$_{17}$H$_{15}$F$_3$N$_4$O$_4$ requires 396.32).

Example 83

1-(3-oxo-4H-1,4-benzoxazin-8-yl)-3-[[5-(trifluoromethyl)-2-pyridyl]methyl]urea

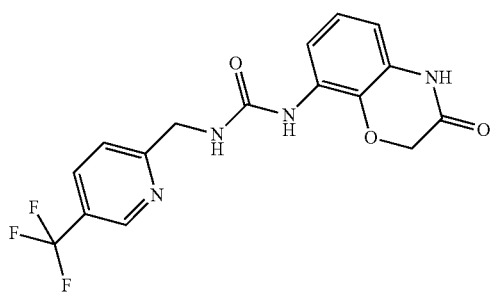

To a solution of triphosgene (0.07 g, 0.37 mol eq) in anh. CH$_2$Cl$_2$ (10 mL) was slowly added the amine 1f (0.2 g, 1 mmol) solubilized in CH$_2$Cl$_2$ (10 mL) and DIEA (2.2 mol eq, 0.4 mL). After the addition was completed, the reaction mixture was stirred at room temp. for 15 min. Then the [5-(trifluoromethyl)-2-pyridyl]methanamine (1 mol eq, 0.18 g) solubilized in CH$_2$Cl$_2$ (10 mL) and DIEA (2.2 mol eq, 0.4 mL) was added in one portion. The mixture obtained was stirred at room temp. for 12 h. The solvent was removed at reduced pressure, water was added and the mixture was extracted with EtOAc (3×20 mL). The recombined organic phases were anhydrified over sodium sulfate and evaporated to dryness. The residue was purified by crystallization from EtOAc to obtain the product as yellow solid (0.132 g, 37% Yield). $^1$HNMR (DMSO, 400 MHz) δ 4.47 (d, 2H, J=6), 4.63 (s, 2H), 6.46 (dd, 1H, J=2), 6.80 (t, 1H, J=8), 7.57 m, 2H), 7.72 (dd, 1H, J=2), 8.18 (dd, 1H, J=2), 8.22 (s, 1H), 8.90 (m, 1H), 10.66 (s, 1H). [M$^{+1}$] 366.94 (C$_{16}$H$_{13}$F$_3$N$_4$O$_3$ requires 366.29).

Example 84

1-[(2-isopropoxy-4-methyl-phenyl)methyl]-3-(3-oxo-4H-1,4-benzoxazin-8-yl)urea (Scheme 15)

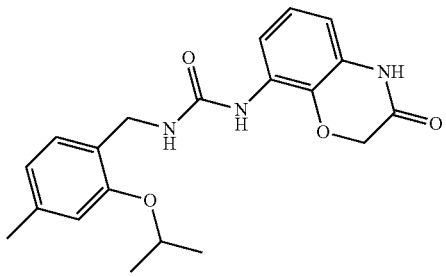 [SMILES: Cc1ccc(CNC(=O)Nc2cccc3c2OCC(=O)N3)c(OC(C)C)c1]

Preparation of 2-isopropoxy-4-methyl-benzonitrile 30a

The 2-fluoro-4-methyl-benzonitrile (0.8 g, 3.99 mmol) was added in small portion to a mixture of NaH 60% (4 mol eq, 0.61 g) in isopropanol (30 mL). The reaction mixture was heated at 50° C. overnight. The solvent was distilled and water was added to the residue. The aqueous solution was extracted with EtOAc (3×25 mL) and the organic phases were evaporated at reduced pressure to give 30a as a deliquescent white solid (1.09 g, 6.22 mmol). $^1$HNMR (DMSO, 200 MHz) δ 1.21 (s, 3H), 1.28 (s, 3H), 2.10 (s, 3H), 4.89 (m, 1H), 7.41 (d, 1H), 7.55 (s, 1H), 7.89 (m, 1H).

Preparation of [2-isopropoxy-4-(trifluoromethyl)phenyl]methanamine 31a

The nitrile 30a (1.09 g, 6.22 mmol) was added in small portion to a mixture of LiAlH$_4$ (0.47 g, 2 mol eq) in Et$_2$O (40 mL) stirred at 0° C. Then the mixture was stirred at room temperature overnight. The excess of LiAlH$_4$ was decomposed by water addition at 0° C., the solid formed was filtered, washed with Et$_2$O and the filtrate was separated. The organic phase was anhydrified over Na$_2$SO$_4$ and evaporated to dryness to obtain 31a as yellow oil (0.95 g, 85% Yield) used without further purification.

Preparation of 1-[(2-isopropoxy-4-methyl-phenyl)methyl]-3-(3-oxo-4H-1,4-benzoxazin-8-yl)urea To a solution of 31a (0.95 g, 5.20 mmol) in THF (20 mL) was added CDI (2.1 mol eq, 1.80 g) and the mixture was heated at 70° C. for 6 h. The reaction mixture was evaporated, water was added and the aqueous phase was extracted with EtOAc (3×35 mL). The recombined organic phases were anhydrified over $Na_2SO_4$ and evaporated at reduced pressure (yellow oil, 1.4 g, 97% yield). The oil obtained (0.7 g, 2.56 mmol) was dissolved in DMF (20 mL) and the bicyclic amine 1f was added (0.8 mol eq, 0.24 g), then the mixture obtained was heated at 100° C. overnight. The solvent was removed at reduced pressure and the residue was purified by chromatography (1:1 EtOAc:Petroleum ether) to obtain the product as a white solid (0.104 g, 24% Yield). $^1$HNMR (DMSO, 400 MHz) δ 1.26 (s, 3H), 1.29 (s, 3H), 2.26 (s, 3H), 4.18 (d, 2H, J=6), 4.60 (m, 3H), 6.44 (dd, 1H), 6.76 (m, 2H), 6.99 (m, 3H), 7.76 (dd, 1H), 8.13 (s, 1H), 10.64 (s, 1H). [$M^{+1}$] 370.00 ($C_{20}H_{23}N_3O_4$ requires 369.41).

Example 85

1-[(2-isopropoxy-6-methyl-3-pyridyl)methyl]-3-(3-oxo-4H-1,4-benzoxazin-8-yl)urea (Scheme 16)

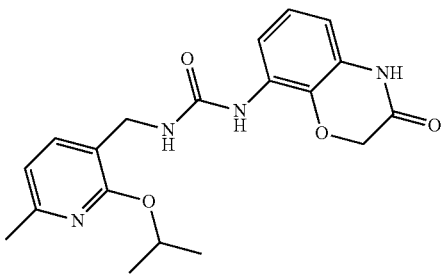 [SMILES: Cc1ccc(CNC(=O)Nc2cccc3c2OCC(=O)N3)c(OC(C)C)n1]

Preparation of 2-isopropoxy-6-methyl-pyridine-3-carbonitrile 32a

The 2-chloro-6-methyl-nicotinonitrile (0.8 g, 5.2 mmol) was added in small portion to a mixture of NaH 60% (4 mol eq, 0.8 g) in isopropanol (30 mL). The reaction mixture was heated at 50° C. overnight. The solvent was distilled and water was added to the residue. The aqueous solution was extracted with EtOAc (3×30 mL) and the organic phases were evaporated at reduced pressure to give 32a as a pale yellow deliquescent solid (1.25 g, quantitative yield). $^1$HNMR (DMSO, 200 MHz) δ 1.24 (s, 3H), 1.32 (s, 3H), 2.25 (s, 3H), 5.02 (m, 1H), 7.31 (d, 1H), 7.69 (m, 1H).

Preparation of [2-isopropoxy-6-methyl-3-pyridyl]methanamine 33a

The nitrile 32a (1.25 g, 7.12 mmol) solubilized in $Et_2O$ (20 mL) and THF (10 mL) was added in small portion to a mixture of $LiAlH_4$ (0.54 g, 2 mol eq) in $Et_2O$ (50 mL) stirred at 0° C. Then the mixture was stirred at room temperature overnight. The excess of $LiAlH_4$ was decomposed by water addition at 0° C., the solid formed was filtered, washed with $Et_2O$ and the filtrate was separated. The organic phase was anhydrified over $Na_2SO_4$ and evaporated to dryness to obtain 33a as yellow oil (1.14 g, 6.35 mmol, 89% Yield) used without further purification.

Preparation of 1-[(2-isopropoxy-6-methyl-3-pyridyl)methyl]-3-(3-oxo-4H-1,4-benzoxazin-8-yl)urea To a solution of 33a (1.14 g, 6.35 mmol) in THF (30 mL) was added CDI (2.1 mol eq, 2.16 g) and the mixture was heated at 70° C. for 6 h. The reaction mixture was evaporated, water was added and the aqueous phase was extracted with EtOAc (3×35 mL). The recombined organic phases were anhydrified over $Na_2SO_4$ and evaporated at reduced pressure (yellow oil, 1.61 g, 93% yield). The oil obtained (0.34 g, 1.25 mmol) was dissolved in DMF (20 mL) and the bicyclic amine 1f was added (0.8 mol eq, 0.20 g), then the mixture obtained was heated at 100° C. overnight. The solvent was removed at reduced pressure and the residue was purified by chromatography (1:1 EtOAc:Petroleum ether) to obtain the product as a white solid (0.07 g, 21% Yield). $^1$HNMR (DMSO, 400 MHz) δ 1.28 (s, 3H), 1.31 (s, 3H), 2.34 (s, 3H), 4.14 (d, 2H, J=6), 4.60 (s, 2H), 5.25 (m, 1H), 6.48 (dd, 1H), 6.77 (m, 2H), 7.11 (t, 1H), 7.44 (d, 1H, J=8), 7.71 (dd, 1H), 8.16 (s, 1H), 10.64 (bs, 1H). [$M^{+1}$] 370.95 ($C_{19}H_{22}N_4O_4$ requires 370.40).

Example 86

1-[[2-dimethylamino-6-(trifluoromethyl)-3-pyridyl]methyl]-3-(3-oxo-4H-1,4-benzoxazin-8-yl)urea (Scheme 14)

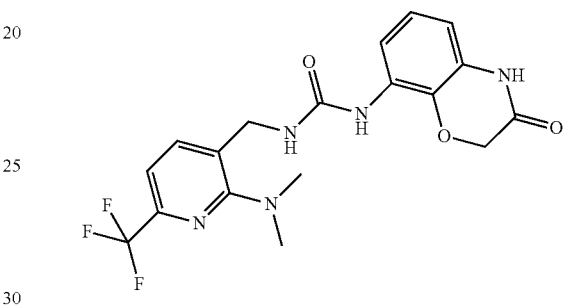

To a solution of 29d (0.78 g, 3.5 mmol) in THF (35 mL) was added CDI (2.1 mol eq, 1.21 g) and the mixture was heated at 70° C. overnight. The reaction mixture was evaporated, water was added and the aqueous phase was extracted with EtOAc (3×25 mL). The recombined organic phases were anhydrified over $Na_2SO_4$ and evaporated at reduced pressure (pale orange oil, quantitative yield). The oil obtained (0.46 g) was dissolved in DMF (25 mL) and the bicyclic amine 1f was added (0.8 mol eq, 0.2 g), then the mixture obtained was heated at 100° C. overnight. The solvent was removed at reduced pressure and the residue was purified by chromatography (7:3 EtOAc:petroleum ether) to obtain the product as a pale yellow solid (0.12 g, 21% Yield). $^1$HNMR (DMSO, 400 MHz) δ 2.84 (s, 6H), 4.36 (d, 2H, J=6), 4.62 (s, 2H), 6.49 (dd, 1H), 6.80 (t, 1H), 7.36 (m, 2H), 7.73 (m, 2H), 8.20 (s, 1H), 10.66 (bs, 1H). [$M^{+1}$] 410.02 ($C_{18}H_{18}F_3N_5O_3$ requires 409.36).

Example 87

1-(3-oxo-4H-1,4-benzoxazin-8-yl)-3-[[2-pyrrolidin-1-yl-6-(trifluoromethyl)-3-pyridyl]methyl]urea (Scheme 14)

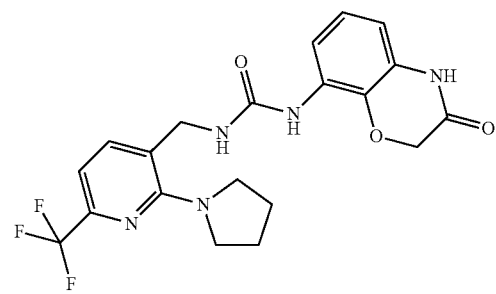 [SMILES: O=C1COc2c(cccc2NC(=O)NCc2ccc(C(F)(F)F)nc2N2CCCC2)N1]

To a solution of 2-(1-pyrrolidinyl)-6-(trifluoromethyl)-3-aminomethyl-pyridine 29e (0.58 g, 2.3 mmol) in THF (25 mL) was added CDI (2.1 mol eq, 0.77 g) and the mixture was heated for 5 h. The reaction mixture was evaporated, water was added and the aqueous phase was extracted with EtOAc (3×20 mL). The recombined organic phases were anhydrified over $Na_2SO_4$ and evaporated at reduced pressure. The oil obtained (0.51 g, 1.52 mmol) was dissolved in DMF (20 mL) and the bicyclic amine 1f was added (0.8 mol eq, 0.20 g), then the mixture obtained was heated at 100° C. overnight. The solvent was removed at reduced pressure and the residue was purified by chromatography (1:1 EtoAc:Petroleum ether) to obtain the product as a white solid (0.12 g, 24% Yield). $^1$HNMR (DMSO, 400 MHz) δ 1.89 (m, 4H), 3.56 (m, 4H), 4.41 (d, 2H, J=6), 4.61 8s, 2H), 6.46 (dd, 1H, J=2), 6.80 (t, 1H, J=8), 7.12 (d, 1H, J=8), 7.25 (t, 1H), 7.70 (m, 2H), 8.17 (bs, 1H), 10.66 (bs, 1H). [M$^{+1}$] 436.03 ($C_{20}H_{20}F_3N_5O_3$ requires 435.40).

Example 88

1-[[2-(imidazol-1-yl)-4-(trifluoromethyl)phenyl]methyl]-3-(3-oxo-4H-1,4-benzoxazin-8-yl)urea

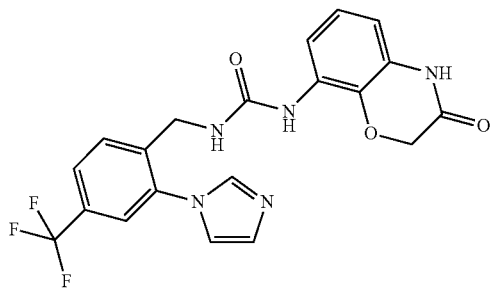 [SMILES: O=C1COc2c(cccc2NC(=O)NCc2ccc(C(F)(F)F)cc2-n2ccnc2)N1]

Preparation of 2-imidazol-1-yl-4-(trifluoromethyl)benzonitrile

To a suspension of NaH 60% (0.09 g, 3.97 mmol) in DMF (20 mL) at 0° C. was added in one portion 1H-imidazole (2.5 mol eq, 0.61 g). After 10 min 2-chloro-4-(trifluoromethyl)-benzonitrile (0.5 mL, 3.61 mmol) was added and the reaction mixture was heated at 100° C. for 2 h. The reaction was cooled at room temperature, water was added and the aqueous solution was extracted with EtOAc (3×25 mL). The recombined organic phases were dried over sodium sulfate and evaporated to dryness to give the 2-imidazol-1-yl-4-(trifluoromethyl)benzonitrile as pale yellow oil (0.63 g, 73% Yield) used for the reduction without further purification.

Preparation of [2-(imidazol-1-yl)-4-(trifluoromethyl)]benzenemethanamine

The nitrile above described (0.63 g, 2.66 mmol) solubilized in $Et_2O$ (20 mL) was added in small portion to a mixture of $LiAlH_4$ (0.202 g, 2 mol eq) in $Et_2O$ (20 mL) stirred at 0° C. Then the mixture was stirred at room temperature overnight. The excess of $LiAlH_4$ was decomposed by water addition at 0° C., the solid formed was filtered, washed with $Et_2O$ and the filtrate was separated. The organic phase was anhydrified over $Na_2SO_4$ and evaporated to dryness to obtain [2-(imidazol-1-yl)-4-(trifluoromethyl)]benzenemethanamine as orange oil (0.53 g, 83% Yield). $^1$HNMR (DMSO, 200 MHz) δ 4.32 (bs, 2H), 7.23 (s, 1H), 7.89 (s, 1H), 8.21 (d, 1H, J=8), 8.41 (m, 1H), 8.94 (dd, 1H, J=2).

Preparation of 1-[[2-imidazol-1-yl-4-(trifluoromethyl)phenyl]methyl]-3-(3-oxo-4H-1,4-benzoxazin-8-yl)urea To a solution of [2-(imidazol-1-yl)-4-trifluoromethyl)]benzenemethanamine (0.53 g, 2.2 mmol) in THF (35 mL) was added CDI (2.1 mol eq, 0.75 g) and the mixture was heated at 70° C. overnight. The reaction mixture was evaporated, water was added and the aqueous phase was extracted with EtOAc (3×25 mL). The recombined organic phases were anhydrified over $Na_2SO_4$ and evaporated at reduced pressure (pale orange oil, quantitative yield). The oil obtained (0.51 g, 1.52 mmol)) was dissolved in DMF (20 mL) and the bicyclic amine 1f was added (0.8 mol eq, 0.2 g), then the mixture obtained was heated at 100° C. overnight. The solvent was removed at reduced pressure and the residue was purified by chromatography (100% EtOAc) to obtain the product as a white solid (0.14 g, 28% Yield). $^1$HNMR (DMSO, 400 MHz) δ 4.20 (d, 2H, J=6), 4.62 (s, 2H), 6.46 (dd, 1H, J=2), 6.79 (t, 1H, J=8), 7.15 (s, 1H), 7.38 (t, 1H), 7.55 (s, 1H), 7.69 (m, 3H), 7.87 (m, 2H), 8.20 (bs, 1H), 10.66 (bs, 1H). [M$^{+1}$] 432.01 ($C_{20}H_{16}F_3N_5O_3$ requires 431.37).

Example 89

1-[(4-tert-butylphenyl)methyl]-3-(3-oxo-4H-1,4-benzoxazin-8-yl)urea

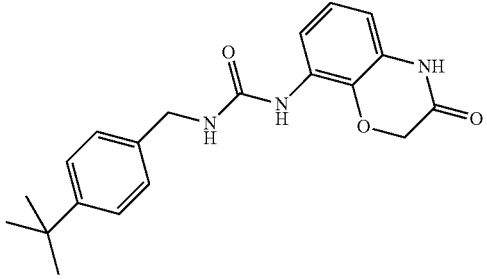 [SMILES: CC(C)(C)c1ccc(CNC(=O)Nc2cccc3c2OCC(=O)N3)cc1]

To a solution of 4-tert-butylbenzylamine (2 mL, 11.36 mmol) in THF (30 mL) was added CDI (2.1 mol eq, 3.86 g) and the mixture was heated at 70° C. overnight. The reaction mixture was evaporated, water was added and the aqueous phase was extracted with EtOAc (3×30 mL). The recombined organic phases were anhydrified over $Na_2SO_4$ and evaporated at reduced pressure (pale yellow oil, quantitative yield). The oil obtained (0.58 g, 2.28 mmol) was dissolved in DMF (20 mL) and the bicyclic amine 1f was added (0.8 mol eq, 0.30 g), then the mixture obtained was heated at 100° C. overnight. The solvent was removed at reduced pressure and the residue was purified by chromatography (1:1 EtOAc:petroleum ether) to obtain the product as a white solid (0.17 g, 27% Yield). $^1$HNMR (DMSO, 400 MHz) δ 1.26 (s, 9H), 4.24 (d, 2H, J=6), 4.60 (s, 2H), 4.45 (dd, 1H, J=2), 6.81 (t, 1H, J=10), 7.18 (d, 2H, J=8), 7.36 (d, 2H, J=8), 7.76 (dd, 1H), 8.06 (bs, 1H), 10.64 (bs, 1H). [M$^{+1}$] 353.98 ($C_{20}H_{23}N_3O_3$ requires 353.41).

Example 90

1-[(4-methyl-2-pyrrolidin-1-yl-phenyl)methyl]-3-(3-oxo-4H-1,4-benzoxazin-8-yl)urea (Scheme 15)

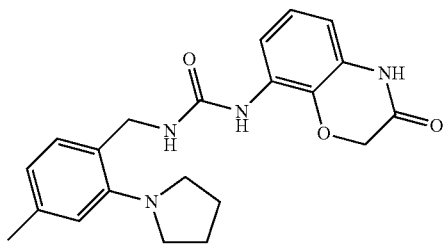 [SMILES: Cc1ccc(CNC(=O)Nc2cccc3c2OCC(=O)N3)c(N2CCCC2)c1]

Preparation of 4-methyl-2-(pyrrolidin-1-yl)-benzonitrile 30b (Scheme 15)

To 2-fluoro-4-methyl-benzonitrile (1.5 g, 11.1 mmol) was added pyrrolidine (3.67 mL, 4 mol eq) and the mixture was heated in neat at 90° C. overnight. The mixture was concentrated, water was added and the mixture was extracted with EtOAc (3×30 mL). The recombined organic phases were anhydrified and evaporated to dryness to obtain 30b as pale yellow crystals (2.03 g, 98% yield). $^1$HNMR (DMSO, 200 MHz) δ 1.21 (m, 4H), 2.10 (m, 4H), 3.89 (s, 3H), 7.31 (d, 1H), 7.45 (s, 1H), 7.79 (m, 1H).

Preparation of (4-methyl-2-pyrrolidin-1-yl-phenyl)-methanamine 31b

The nitrile 30b (2.03 g, 10.9 mmol) solubilized in $Et_2O$ (25 mL) was added in small portion to a mixture of $LiAlH_4$ (0.83 g, 2 mol eq) in $Et_2O$ (30 mL) stirred at 0° C. Then the mixture was stirred at room temperature overnight. The excess of $LiAlH_4$ was decomposed by water addition at 0° C., the solid formed was filtered, washed with $Et_2O$ and the filtrate was separated. The organic phase was anhydrified over $Na_2SO_4$ and evaporated to dryness to obtain 31b as a pale yellow oil (2.12, quantitative Yield) used without further purification.

Preparation of 1-[(4-methyl-2-pyrrolidin-1-yl-phenyl)methyl]-3-(3-oxo-4H-1,4-benzoxazin-8-yl)urea To a solution of 31b (2.1 g, 11 mmol) in THF (50 mL) was added CDI (2.1 mol eq, 3.79 g) and the mixture was heated for 5 h. The reaction mixture was evaporated, water was added and the aqueous phase was extracted with EtOAc (3×30 mL). The recombined organic phases were anhydrified over $Na_2SO_4$ and evaporated at reduced pressure to obtain a pale yellow oil (3.5 g). One portion of this oil (0.7 g, 2.46 mmol) was dissolved in DMF (20 mL) and the bicyclic amine 1f was added (0.8 mol eq, 0.25 g), then the mixture obtained was heated at 100° C. overnight. The solvent was removed at reduced pressure and the residue was purified by chromatography (1:1 EtOAc:petroleum ether) to obtain the product as a pale yellow solid (0.30 g, 0.78 mmol, 31% Yield). $^1$HNMR (DMSO, 400 MHz) δ 1.87 (m, 4H), 2.23 (s, 3H), 3.10 (m, 4H), 4.26 (d, 2H, J=6), 4.60 (s, 2H), 6.44 (dd, 1H), 6.76 (m, 3H), 7.1 (d, 2H), 7.74 (dd, 1H), 8.13 (s, 1H), 10.64 (bs, 1H).

Example 91

1-[[2-(2-dimethylaminoethoxy)-6-(trifluoromethyl)-3-pyridyl]methyl]-3-(3-oxo-4H-1,4-benzoxazin-8-yl) urea (Scheme 14)

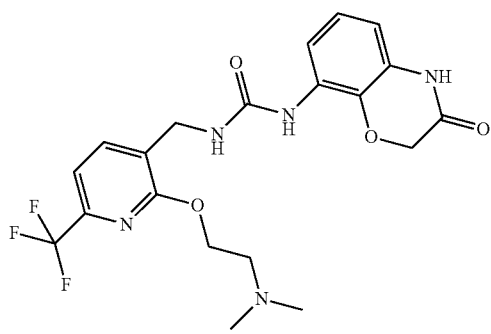 [SMILES: CN(C)CCOc1nc(C(F)(F)F)ccc1CNC(=O)Nc1cccc2c1OCC(=O)N2]

To a solution of 29b (1.21 g, 4.6 mmol) in THF (25 mL) was added CDI (2.1 mol eq, 1.6 g) and the mixture was heated at 70° C. for 6 h. The reaction mixture was evaporated, water was added and the aqueous phase was extracted with EtOAc (3×30 mL). The recombined organic phases were anhydrified over $Na_2SO_4$ and evaporated at reduced pressure (yellow oil, 1.17 g, 71% yield). The oil obtained was dissolved in DMF (20 mL) and the bicyclic amine 1a was added (0.8 mol eq, 0.35 g), then the mixture obtained was heated at 100° C. overnight. The solvent was removed at reduced pressure and the residue was purified by chromatography (8:2 EtOAc:MeOH) to obtain the product as a pale yellow solid (0.23 g, 24% Yield). $^1$HNMR (DMSO, 400 MHz) δ 2.33 (s, 6H), 2.83 (t, 2H), 4.30 (d, 2H, J=6), 4.45 (t, 2H, J=6), 4.61 (s, 2H), 6.46 (dd, 1H), 6.80 (t, 1H, J=8), 7.36 (t, 1H), 7.47 (d, 1H, J=8), 7.76 (m, 2H), 8.25 (s, 1H), 10.67 (bs, 1H).

$[M^{+1}]$ 454.02 ($C_{20}H_{22}F_3N_5O_4$ requires 453.41).

Example 92

1-[[2-(2-dimethylaminoethoxy)-4-(trifluoromethyl) phenyl]methyl]-3-(3-oxo-4H-1,4-benzoxazin-8-yl) urea (Scheme 13)

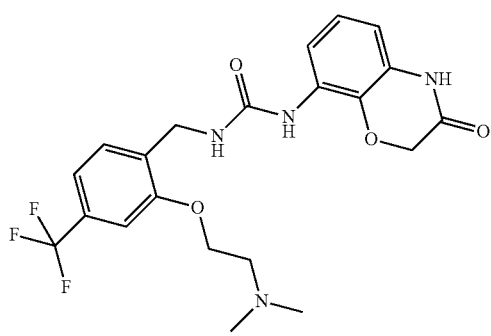 [SMILES: CN(C)CCOc1cc(C(F)(F)F)ccc1CNC(=O)Nc1cccc2c1OCC(=O)N2]

To a solution of 27b (1.48 g, 5.64 mmol) in THF (25 mL) was added CDI (2.1 mol eq, 1.92 g) and the mixture was heated at 70° C. overnight. The reaction mixture was evaporated, water was added and the aqueous phase was extracted with EtOAc (3×30 mL). The recombined organic phases were anhydrified over Na$_2$SO$_4$ and evaporated at reduced pressure (pale yellow oil, 1.91 g, 95% yield). The oil obtained (0.95 g, 2.68 mmol) was dissolved in DMF (20 mL) and the bicyclic amine 1f was added (0.8 mol eq, 0.35 g), then the mixture obtained was heated at 100° C. overnight. The solvent was removed at reduced pressure and the residue was purified by chromatography (8:2 EtOAc:MeOH) to obtain the product as a white solid (0.33 g, 35% Yield). $^1$HNMR (DMSO, 400 MHz) δ 2.27 (s, 6H), 2.71 (t, 2H), 4.20 (t, 2H), 4.32 (d, 2H, J=6), 4.62 (s, 2H), 6.50 (dd, 1H), 6.80 (t, 1H), 7.29 (m, 3H), 7.40 (d, 1H), 7.70 (dd, 1H), 8.18 (s, 1H), 10.65 (bs, 1H). [M$^{+1}$] 452.91 (C$_{21}$H$_{23}$F$_3$N$_4$O$_4$ requires 452.43).

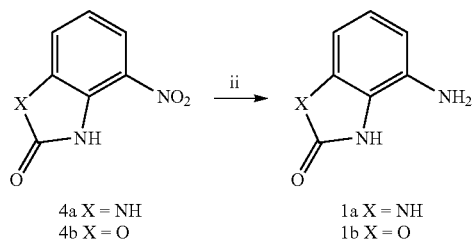

4a X = NH
4b X = O

1a X = NH
1b X = O

Reagents: i) DCI, THF, Rfx, 2 or 4 hrs; ii) H$_2$, C/Pd 10%, MeOH/THF, 60 psi, overnight Scheme 1

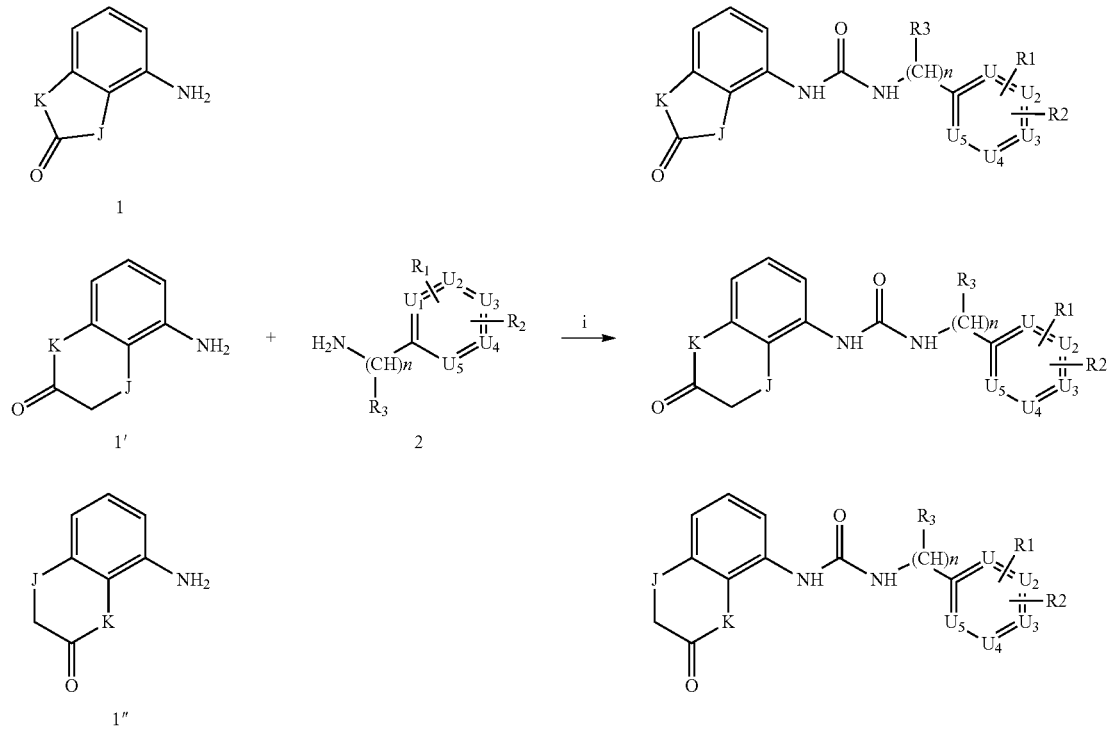

Reagents: i) isocyanate freshly prepared from amine 2 or sometimes alternatively from amine 1, 1′ or 1″ triphosgene in AcOEt at 80° C. for 4 hrs, DMF, 80° C., 8 hr Scheme 2

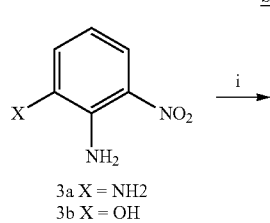

3a X = NH2
3b X = OH

Scheme 3

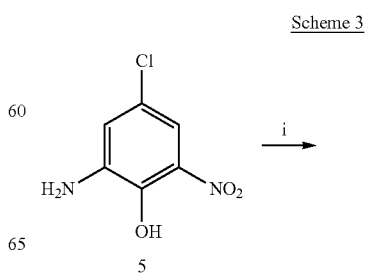

5

87
-continued

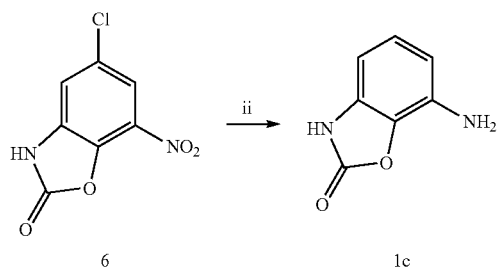

Reagents: i) DCI, AcOEt, rt; 2 hrs; ii) H$_2$, C/Pd 10%, TEA, MeOH/THF, 60 psi, overnight Scheme 4

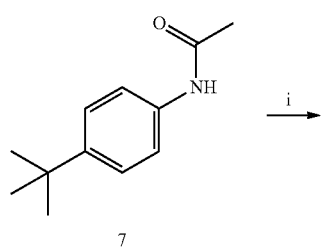

88

Scheme 5

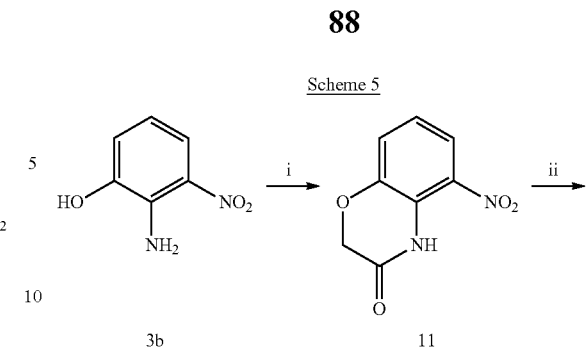

Reagents: i) K$_2$CO$_3$, ethylbromoacetate, DMF, rt, 24 h; ii) C/Pd 10%, CH$_3$OH/THF, 60 psi, overnight Scheme 6

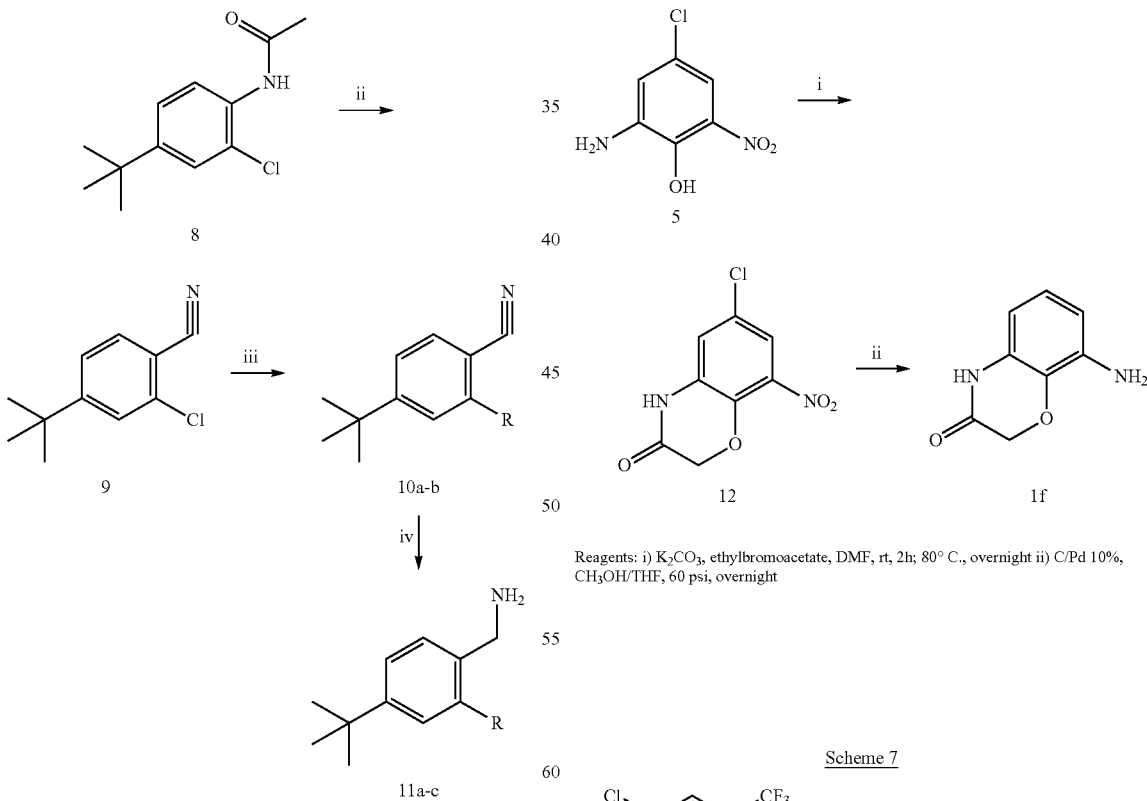

Reagents: i) K$_2$CO$_3$, ethylbromoacetate, DMF, rt, 2h; 80° C., overnight ii) C/Pd 10%, CH$_3$OH/THF, 60 psi, overnight Scheme 7

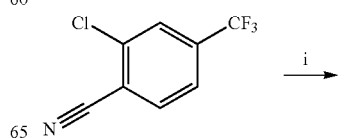

R = pyrrolidinyl (a); piperidinyl (b); chloro (c).
Reagents: (i) NCS, DMF, rt; (ii) HCl 20%, 100° C., Overnight; H$_2$SO$_4$ 98%, NaNO$_2$, Tetrabutylammonium cyanide, CH$_3$CO$_2$H:H$_2$O (10:6); (iii) amine, steel-bomb, 200° C., Overnight; (iv) LiAlH$_4$, Et$_2$O, Overnight, rt.

89

-continued

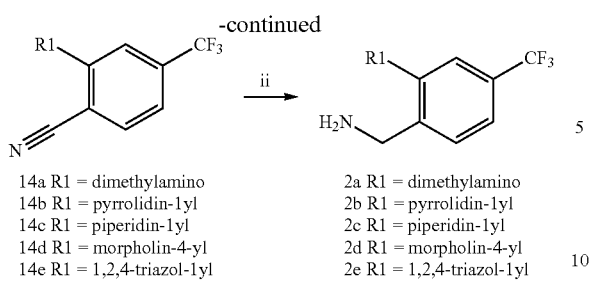

14a R1 = dimethylamino
14b R1 = pyrrolidin-1yl
14c R1 = piperidin-1yl
14d R1 = morpholin-4-yl
14e R1 = 1,2,4-triazol-1yl 2a R1 = dimethylamino
2b R1 = pyrrolidin-1yl
2c R1 = piperidin-1yl
2d R1 = morpholin-4-yl
2e R1 = 1,2,4-triazol-1yl Compounds 2 wherein R2 = CF3, R3 = H, n = 1
Reagents: i) R1, 80° C., 4h; ii) LiAlH4, diethylether, rt, overnight

90

-continued

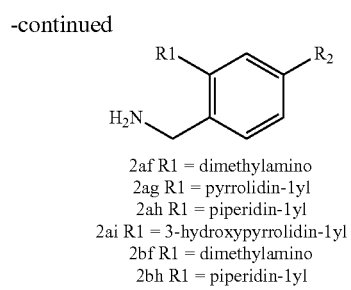

2af R1 = dimethylamino
2ag R1 = pyrrolidin-1yl
2ah R1 = piperidin-1yl
2ai R1 = 3-hydroxypyrrolidin-1yl
2bf R1 = dimethylamino
2bh R1 = piperidin-1yl Compounds 2 wherein R2 = Cl or CH3, R3 = H, n = 1
Reagents: i) R1, 80° C., overnight; ii) LiAlH4, diethylether, rt, overnight

Scheme 8

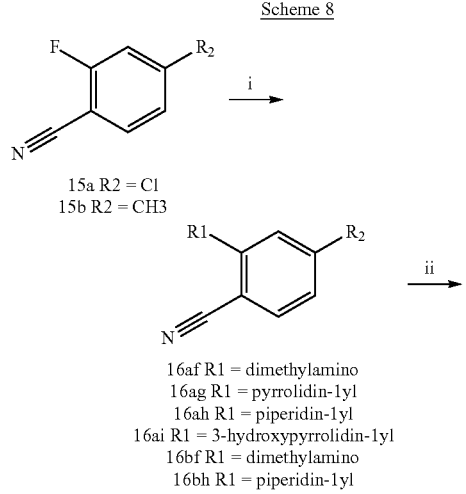

15a R2 = Cl
15b R2 = CH3

16af R1 = dimethylamino
16ag R1 = pyrrolidin-1yl
16ah R1 = piperidin-1yl
16ai R1 = 3-hydroxypyrrolidin-1yl
16bf R1 = dimethylamino
16bh R1 = piperidin-1yl

Scheme 9

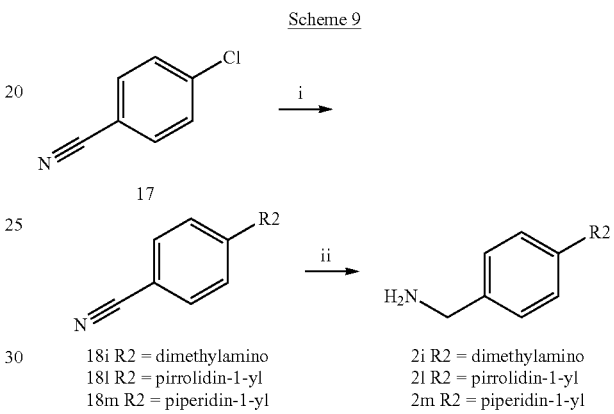

17

18i R2 = dimethylamino
18l R2 = pirrolidin-1-yl
18m R2 = piperidin-1-yl

2i R2 = dimethylamino
2l R2 = pirrolidin-1-yl
2m R2 = piperidin-1-yl

Compounds 2 wherein R1 = R3 = H, n = 1
Reagents: i) R2, 100° C., 36 hrs ii) LiAlH4, diethylether, rt, overnight

Scheme 10

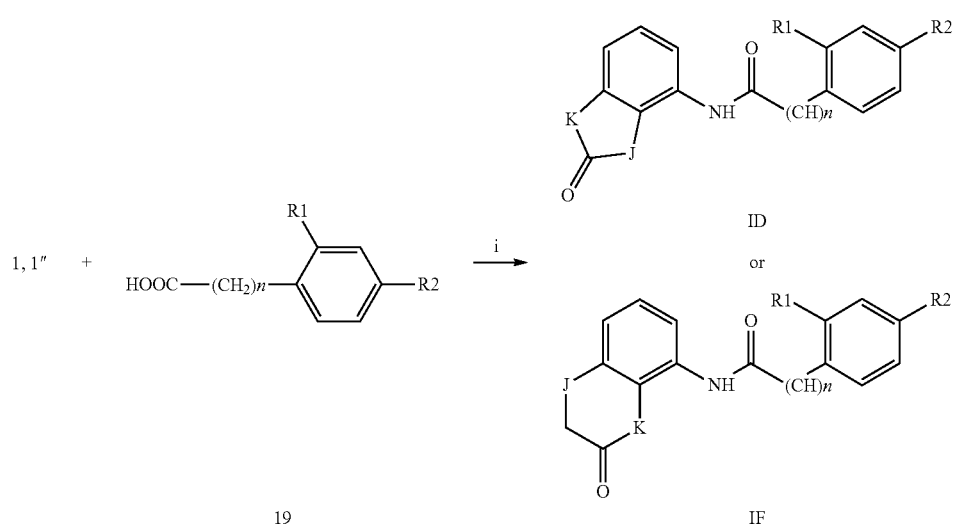

19

Reagents: i) DEPC, THF, 80° C., overnight

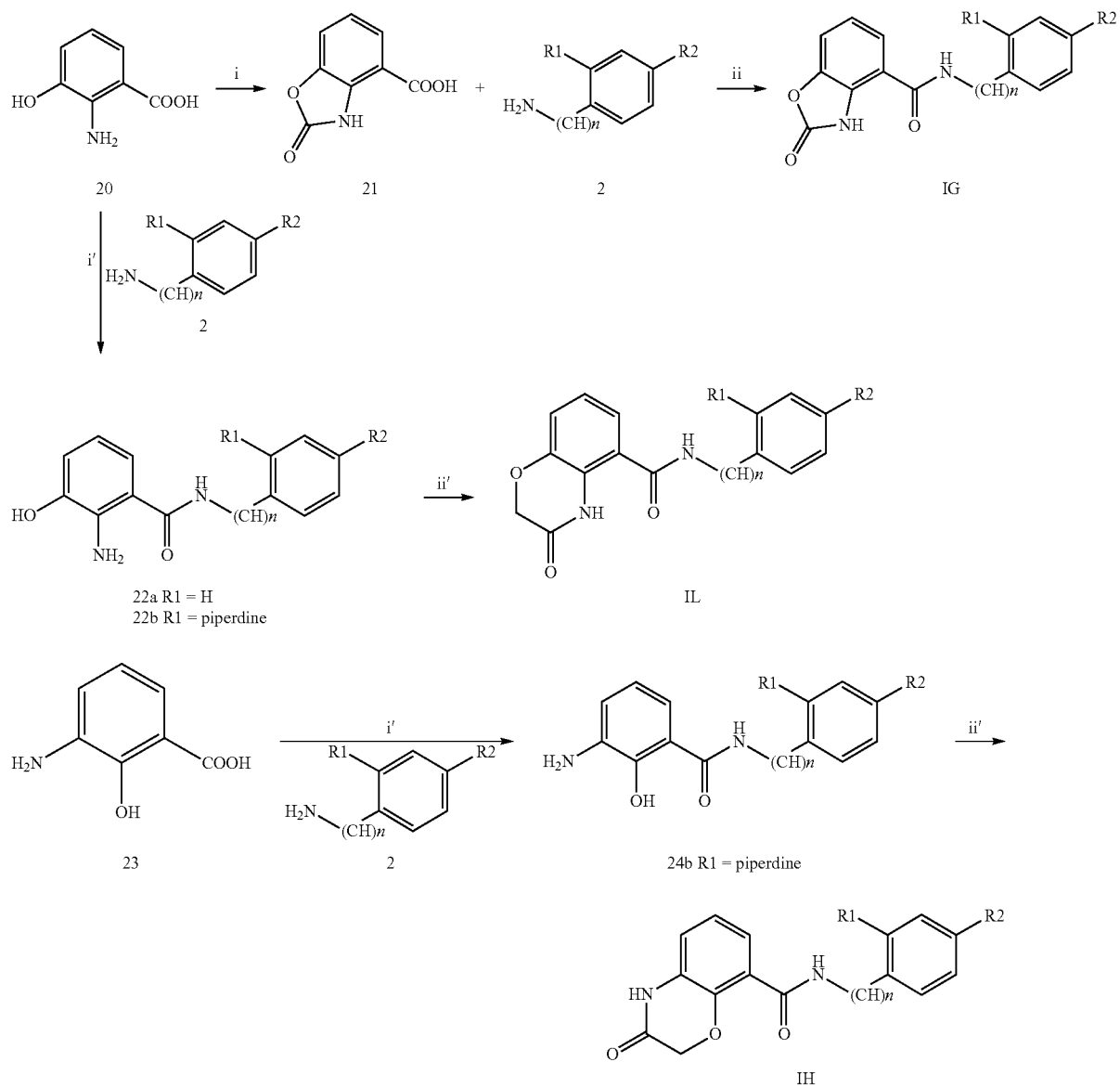
Reagents: i) CDI, THF, Reflux; ii) DEPC, THF, rfx, overnight; i') EDCI, HOBT, DMF, rt, overnight; ii') chloroacetyl chloride, TEA, 4h, rt, K₂CO₃, 20 h, rt
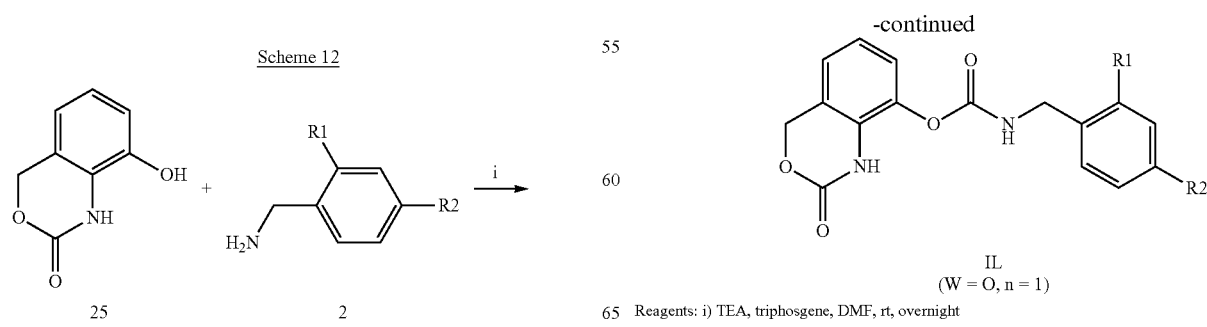
Reagents: i) TEA, triphosgene, DMF, rt, overnight Scheme 13

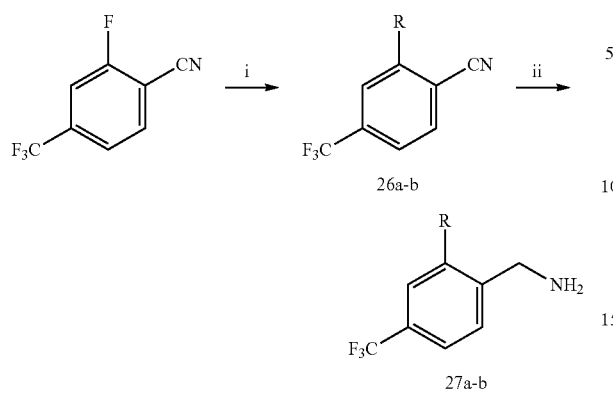

26a-b 27a-b

R = isopropyloxy (a), N,N'-dimethylaminoethoxy (b)
Reagents: i) isopropanol, NaH 60%, 50° C.; ii) LiAlH$_4$, diethylether, rt, overnight Scheme 14

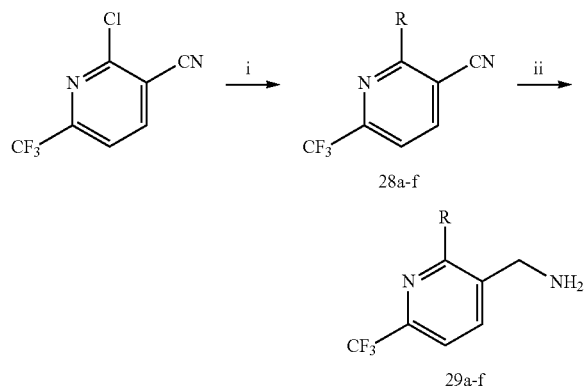

28a-f 29a-f

R = isopropyloxy (a), N,N'-dimethylaminoethoxy (b), methoxy (c), N,N-dimethylamino (d), pyrrolidinyl (e), piperidinyl (f).
Reagents: i) alchol or amine (Ra-f), 90° C.; ii) LiaLH$_4$, diethylether, rt, overnight or Pd/C 10%, 70 psi.

Scheme 15

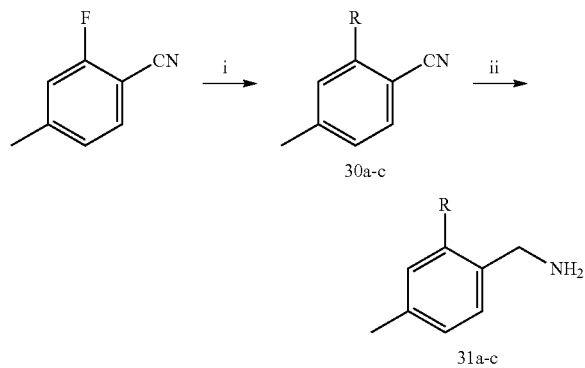

30a-c 31a-c

R = isopropyloxy (a), pyrrolidinyl (b), N,N'-dimethylamino (c)
Reagents: i) alchol or amine (Ra-c), 90° C. or NaH 60%, 50° C.; ii) LiAlH$_4$, diethylether, rt, overnight Scheme 16

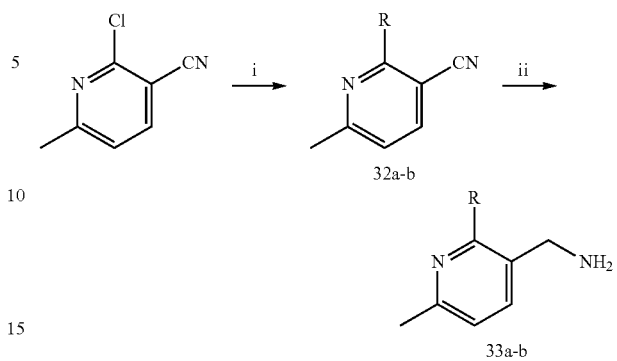

32a-b 33a-b

R = isopropyloxy (a), piperidinyl (b)
Reagents: i) alchol or amine (Ra-b), 90° C. or NaH 60%, 50° C.; ii) LiAlH$_4$, diethylether, rt, overnight.

Pharmacology

Drugs and reagents were obtained from the indicated companies: capsaicin, ionomycin, laminin, poly-L-lysine, collagenase, trypsin, L-glutamine, penicillin/streptomycin, DMEM, HBSS, mouse-NGF-7S, ARA-C, HEPES, Tween80, Complete Freund's Adjuvant (CFA) and BSA (Sigma, Italy); FBS and HS (Gibco, Italy); Fura-2-AM-ester (Vinci-Biochem, Italy) and Methylcellulose (Fluka, Switzerland). The stock concentration (10 mM) of capsaicin, Fura-2-AM-ester, ionomycin and all tested compounds were prepared in 100% DMSO.

$Ca^{2+}$ Fluorescence Measurements in Cultured Rat Dorsal Root

Male SD rats (~50 g, Charles River, Italy) were terminally anaesthetized and decapitated. Dorsal root ganglia were removed and placed in cold Hank's balanced salt solution (HBSS) before being transferred to collagenase (2 mg/ml) and trypsin (1 mg/ml) for 35 min at 37° C. The ganglia, placed in cold DMEM supplemented with 10% fetal bovine serum, 10% horse serum, 2 mM L-glutamine, 100 U/ml penicillin and 100 μg/ml streptomycin, were dissociated in single cells by several passages through a series of syringe needles (23G down to 25G). The medium and the ganglia were filtered to remove debris, topped up with 4 ml of DMEM medium and centrifuged (1100 rpm for 6 min). The final cell pellet was re-suspended in DMEM medium [supplemented with 100 ng/ml mouse Nerve Growth Factor (mouse-NGF-7S) and cytosine-β-D-arabinofuranoside free base (ARA-C) 2.5 μM]. The cells were plated on poly-L-lysine (8.3 μM)- and laminin (5 μM)-coated 25 mm glass cover slips and kept for 2 days at 37° C. in a humidified incubator gassed with 5% $CO_2$ and air, then treated with Fura-2-AM-ester (5 μM) in a $Ca^{2+}$ buffer solution having the following composition (mM): $CaCl_2$ 1.4, KCl 5.4, $MgSO_4$ 0.4, NaCl 135, D-glucose 5, HEPES 10 with BSA (0.1%), at pH 7.4, for 40 min at 37° C. The cells were then washed twice with the $Ca^{2+}$ buffer solution and transferred to a chamber on the stage of a Nikon eclipse TE300 microscope. Fura-2-AM-ester was excited at 340 nM and 380 nM to indicate relative $[Ca^{2+}]_i$ changes by the $F_{340}/F_{380}$ ratio recorded with a dynamic image analysis system (Laboratory Automation 2.0, RCS, Florence, Italy) and the cells were allowed (at least 10 min) to attain a stable fluorescence before beginning the experiment. A calibration curve was set up using buffer containing Fura-2-AM-ester and determinant concentrations of free $Ca^{2+}$. This curve was then used to convert the data obtained from the $F_{340}/F_{380}$ ratio to $[Ca^{2+}]_i$ (nM).

All exemplified compounds were tested at the concentration of 300 nM against the calcium uptake induced by 30 nM capsaicin. For selected molecules, the $IC_{50}$ value was calculated.

CFA-Induced Thermal Hyperalgesia in Rats

This method was used for the determination of acute nociceptive thermal threshold and combines a chemical stimulus and heat for measuring pain sensitivity. Male SD rats (Charles River, Italy) weighing 100 to 250 gr. were used. Anti-hyperalgesic effects were investigated by using the Hargreaves' test. Complete Freund's Adjuvant (CFA; Sigma, USA) was used to induce thermal hyperalgesia. CFA contains killed *Mycobacterium tuberculosis* and is designed to provide continuous release of antigens necessary for stimulating a strong, persistent immune response. This effect causes the reduction of the hind paw withdrawal response latency induced by heat during the Hargreaves' test. Thermal stimulation was performed 30, 60, 120 and 180 (240 min only if needed) minutes after the oral administration of the antagonists. During the CFA-induced thermal hyperalgesia experiments two different solubilization protocols were used: when items presented an amino group, a pH=2 aqueous solution of HCl and 2.5% Tween80 was used; otherwise molecules were suspended in 0.5% Methocel and 2.5% Tween80. Compounds were orally administrated (30 µmol/kg/10 ml) to rats 24 hours after the CFA treatment. CFA was injected into the plantar surface of a rat's hind paw at a fixed dose of 50 µl by the use of a micro syringe.

CFA-Induced Tactile Allodynia in Rats

Male SD rats (Charles River, Italy) weighing 100 to 250 g were put into a clean plastic cage on an elevated glass plate for 30 min before the test. This lets the animals accommodate to their new environment before testing. Complete Freund's adjuvant (CFA, 50 µl) was injected into the plantar surface of the right hind paw. Tactile stimulation was performed with von Frey filaments (from 0.07 to 26 g). All antagonists were orally administered 22 hours after to the CFA administration. Von Frey filaments were applied 30, 60, 120, 180, 240, 300 and 360 min after compound administrations. Median 50% ($EG_{50}$) threshold of von Frey filaments was calculated by using the up-down method as previously described. All tested compounds were suspended in 0.5% Methocel and 2.5% Tween80 and orally administrated (30 µmol/kg/10 ml) to rats by gavage 24 hours after the CFA treatment. CFA was injected into the plantar surface of a rat's hind paw at a fixed dose of 50 µl by the use of a micro syringe.

Rectal Temperature Measurements in Rats

Body temperature was measured by a digital thermometer inserted at a depth of approximately 3 cm into the rectum of each animal (male SD rats, Charles River, Italy, 100 to 250 g). A pre-dose value of body temperature was measured prior to the administration of the test substance or vehicles. Animals were distributed among groups by the manual method to achieve the almost same mean values of body temperature of the groups based on the pre-dose value. All compounds were dissolved in 6% DMSO/6% Tween80 and then intraperitoneally (10 µmol/Kg/5 ml) administrated to rats.

CCI-Induced Mechanical Hyperalgesia

Male SD rats (Charles River, Italy) weighing 250 g were anaesthetized with sodium pentobarbital (60 mg/kg, intraperitoneal (i.p.), 0.1 ml/10 g) and, under a dissecting microscope, the right common sciatic nerve was exposed at the level of the mid thigh and, proximal to the trifurcation of the nerve; four ligatures (4/0 chromic silk, Ethicon) were loosely tied around it, at about 0.5 mm spacing, until they elicited a brief twitch in the respective hind, taking care to preserve epineural circulation. Sham-operated animals (sciatic exposure without ligation) were used as controls. 14 days after the surgery, mechanical hyperalgesia was assessed using an analgesimeter (Ugo Basile, Italy, Randall-Selitto analgesic apparatus). This device generated a mechanical force on the affected paw and the nociceptive threshold was defined as the force (in g) at which the rat withdraws the paw (with a cut-off of 450 g). Two baseline measurement values were obtained 75 and 45 min before the actual test. After the second baseline measurement, animals were randomly allocated to the different treatment groups. Paw pressure test was performed 0, 75, 120, 165, 210 and 300 min after the oral administration of the compounds. All tested compounds were orally administrated (30 µmol/kg/10 ml) to rats by gavage.

RESULTS $Ca^{2+}$ Fluorescence Measurements in Cultured Rat Dorsal Root Ganglia Neurons Capsaicin (0.3 µM) caused an increase in $[Ca^{2+}]$ in the vast majority (95%) of dorsal root ganglia neurons, which were thereby identified as TRPV1 expressing neurons. All synthesized derivatives were tested and all were able to inhibit the calcium uptake and several compounds exhibited more than 80% inhibition, e.g. compounds of Examples 1, 3, 4, 5, 6, 10, 11, 12, 13, 16, 19, 23, 31, 32, 35, 36, 39, 41, 45, 46, 47, 48, 51, 53, 67, 68, 69, 70, 71, 74, 75, 78, 80, 81, 82, 86, 87 and 89. Among them, derivatives such as compounds of Examples 4, 5, 6, 13, 19, 31, 36, 39, 45, 46, 47, 48, 51, 52, 53, 67, 70, 71, 74, 75, 78, 80, 81, 86 and 87, appeared the most potent TRPV1 antagonists exhibiting a complete abolition of capsaicin response (around 100%) at 300 nM.

The $IC_{50}$ values of the compounds of Examples 4, 5, 6, 12, 13, 31, 46, 47, 48, 51, 73, 75 and 78 calculated against capsaicin-evoked $[Ca^{2+}]_i$ mobilization were 4.07 nM, 1 nM, 0.51 nM, 6 nM, 1.8 nM, 1.9 nM, 3 nM, 0.7 nM, 0.13 nM, 1.8, 0.1 nM, 0.84 nM and 0.61, respectively.

Tables 1, 2 and 3 describe the calcium assay data for all exemplified compounds of formula IA-C, ID-E and IF-H, respectively.

TABLE 1

| Compound of Example | % inhibition at 300 nM | IC50 (nM) |
| --- | --- | --- |
| Example 1 | 84 | |
| Example 2 | 28 | |
| Example 3 | 93 | |
| Example 4 | 100 | 4.07 |
| Example 5 | 100 | 1 |
| Example 6 | 95 | 0.51 |
| Example 7 | 33 | |
| Example 8 | 2 | |
| Example 9 | 18 | |
| Example 10 | 89 | 79 |
| Example 11 | 82 | 12 |
| Example 12 | 88 | 6 |
| Example 13 | 96 | 1.8 |
| Example 14 | 32 | |
| Example 15 | 54 | |
| Example 16 | 86 | |
| Example 17 | 44 | |
| Example 18 | 54 | |
| Example 19 | 99 | |
| Example 20 | 18 | |
| Example 21 | 79 | |
| Example 22 | 48 | |
| Example 23 | 82 | 108 |
| Example 24 | 40 | |
| Example 25 | 40 | |
| Example 26 | 55 | |
| Example 27 | 45 | |
| Example 28 | 40 | |
| Example 29 | 8 | |
| Example 30 | 44 | |
| Example 31 | 100 | 1.9 |
| Example 32 | 93 | |
| Example 33 | 16 | |
| Example 34 | 19 | |
| Example 35 | 90 | |
| Example 36 | 100 | |
| Example 39 | 98 | 9.5 |
| Example 40 | 52 | |

TABLE 1-continued

| Compound of Example | % inhibition at 300 nM | IC50 (nM) |
|---|---|---|
| Example 41 | 88 | |
| Example 42 | 30 | |
| Example 43 | 23 | |
| Example 44 | 47 | |
| Example 45 | 100 | |
| Example 46 | 94 | 3 |
| Example 47 | 100 | 0.7 |
| Example 48 | 100 | 0.13 |
| Example 49 | 68 | |
| Example 50 | 52 | |
| Example 51 | 100 | 0.1 |
| Example 52 | 98 | |
| Example 53 | 90 | |
| Example 54 | 55 | |
| Example 66 | 71 | |
| Example 67 | 100 | 20 |
| Example 68 | 93 | |
| Example 69 | 80 | 92 |
| Example 70 | 98 | |
| Example 71 | 100 | 12 |
| Example 72 | 40 | 6 |
| Example 73 | 25 | 1.8 |
| Example 74 | 100 | |
| Example 75 | 100 | 0.84 |
| Example 76 | 40 | |
| Example 77 | 71 | |
| Example 78 | 100 | 0.61 |
| Example 79 | 54 | |
| Example 80 | 95 | |
| Example 81 | 100 | |
| Example 82 | 90 | 54 |
| Example 83 | 57 | |
| Example 84 | 61 | |
| Example 85 | 79 | |
| Example 86 | 100 | 17 |
| Example 87 | 100 | 9 |
| Example 88 | 75 | |
| Example 89 | 92 | 19.8 |
| Example 90 | 47 | |
| Example 91 | 40 | |
| Example 92 | 12 | |

TABLE 2

| Compound of Example | % inhibition at 300 nM |
|---|---|
| Example 55 | 10 |
| Example 56 | 31 |
| Example 57 | 7 |
| Example 58 | 43 |

TABLE 3

| Compound of Example | % inhibition at 300 nM |
|---|---|
| Example 59 | 5 |
| Example 60 | 8 |
| Example 61 | 15 |
| Example 62 | 8 |
| Example 63 | 79 |
| Example 64 | 65 |
| Example 65 | 4 |

CFA-Induced Thermal Hyperalgesia in Rats

The more potent antagonists were orally administered at 30 μmol/kg. The compound of Example 51 was able to counteract the CFA effects producing a maximal reversal activity of 30%. In contrast, the compounds of Examples 5, 12, 13, 23, 31, 46, 47, 48, 49 produced a sustained anti-hyperalgesic effect showing 53%, 65%, 60%, 46%, 47%, 50%, 46%, 45% and 52% of reversion respectively.

CFA-Induced Tactile Allodynia in Rats

The compound of Example 5 (30 μmol/kg, oral) significantly reversed CFA-induced tactile allodynia (60% of reversal) up to 240 min post-treatment while the same dose of the compound of Example 51 provoked 61% of reversal but showed a shorter duration. The compound of Example 12 produced a statistically significant anti-hyperalgesic effect up to 300 min post-treatment. (62% of reversal). The compound of example 49 joined 72% of reversal.

Rectal Temperature Measurement in Rats

None of the more potent compounds affected rectal rat body temperature apart from the compound of Example 31 which induced hypothermia (−1.5° C.), and the compound of Example 46 which caused hyperthermia. (+0.8° C.).

CCI-Induced Mechanical Hyperalgesia

All selected compounds exhibited a significant anti-hyperalgesic effect. Particularly, derivatives the compounds of Examples 1, 5, 6, 31, 13, 46 and 49 induced relevant and long lasting anti-hyperalgesic activity. Moreover, all the above mentioned compounds produced at least 80% reversal of hyperalgesia within the first 2 hours of experimentation.

REFERENCES (1) Cortright, D. N. and Szallasi, A. TRP channels and pain Current Pharmaceutical Design 2009, 15, 1736-1749.
(2) Gunthorpe M. J. and Szallasi, A. Peripheral TRPV1 receptors as targets for drug development: new molecules and mechanisms Current Pharmaceutical Design 2008, 14, 32-41.
(3) Nachman R. J. 1,1-carbonyldiimidazole Journal of Heterocyclic Chemistry 1982, 19, 1545-1547.
(4) Eijgendaal, I.; Klein, G.; Terhorst-Van Amstel, M. J. L.; Zwier, K.; Bruins, N.; Rigter, H. T.; Gout, E.; Boon, C.; De Vries, M. H. Stable crystalline form of bifeprunox mesylate, dosage forms thereof and therapeutic uses for CNS disorders. WO 2006087369 Solvay Pharmaceuticals B.V.
(5) Kath, J. C.; Luzzio, M. J. Pyrimidine derivatives for the treatment of abnormal cell growth, their preparation and pharmaceutical compositions. US 2005256125 Pfizer Inc.
(6) Singh, J.; Gurney, M.; Hategan, G.; Yu, P.; Zembower, D.; Zhou, N.; Polozov, A.; Zeller, W. Carboxylic acid peri-substituted bicyclics and their preparation, pharmaceutical compositions, and prostanoid EP3 receptor binding activity for treatment of occlusive artery disease. WO 2006044415 Decode Chemistry, Inc.
(7) Ceccarelli, S. M.; Jaeschke, G.; Buettelmann, B.; Huwyler, J.; Kolczewski, S.; Peters, J.-U.; Prinssen, E.; Porte, R.; Spooren, W. and Vieira, E. Rational design, synthesis, and structure-activity relationship of benzoxazolones: new potent mglu5 receptor antagonists based on the fenobam structure Bioorganic & Medicinal Chemistry Letters 2007, 17, 1302-1306.
(8) Hossain, N.; Ivanova, S.; Mensonides-Harsema, M. Preparation of spiroheterocyclic-piperidine or -pyrrolidine derivatives as chemokine receptor modulators. WO 2005054249 Astrazeneca AB.
(9) Kudo, Y.; Ozaki, K.; Miyakawa, A.; Amano, T.; Ogura, A. Monitoring of intracellular Ca2+ elevation in a single neural cell using a fluorescence microscope/video-camera system. Japanese Journal of Pharmacology 1986, 41, 345-351.
(10) Hargreaves, K.; Dubner, R.; Brown, F.; Flores, C.; Joris, J. A new and sensitive method for measuring thermal nociception in cutaneous hyperalgesia. Pain 1988, 32, 77-88.
(11) Galbraith, J. A.; Mrosko, B. J.; Myers, R. R. A system to measure thermal nociception. Journal of Neuroscience Methods 1993, 49, 63-68.

(12) Chaplan, S. R.; Bach, F. W.; Pogrel, J. W.; Chung, J. M.; Yaksh, T. L. Quantitative assessment of tactile allodynia in the rat paw. Journal of Neuroscience Methods. 1994, 53, 55-63.

(13) Leighton, G. E.; Rodriguez, R. E.; Hill, R. G.; Hughes, J. kappa-Opioid agonists produce antinociception after i.v. and i.c.v. but not intrathecal administration in the rat. British Journal of Pharmacology 1988, 93, 553-560.

The invention claimed is:

1. A compound selected from the group consisting of:
1-(4-(trifluoromethyl)benzyl)-3-(3,4-dihydro-3-oxo-2H-benzo[b][1,4]oxazin-5-yl)urea,
1-(4-(trifluoromethyl)-2-(pyrrolidin-1-yl)benzyl)-3-(3,4-dihydro-3-oxo-2H-benzo [b][1,4] oxazin-5-yl)urea,
1-(4-(trifluoromethyl)-2-(piperidin-1-yl)benzyl)-3-(3,4-dihydro-3-oxo-2H-benzo [b][1,4]oxazin-5-yl)urea,
1-(4-(trifluoromethyl)benzyl)-3-(3,4-dihydro-3-oxo-2H-benzo [b][1,4]oxazin-8-yl)urea,
1-(2-(dimethylamino)-4-(trifluoromethyl)benzyl)-3-(3,4-dihydro-3-oxo-2H-benzo [b][1,4]oxazin-8-yl)urea,
1-(4-(trifluoromethyl)-2-(pyrrolidin-1-yl)benzyl)-3-(3,4-dihydro-3-oxo-2H-benzo [b][1,4]oxazin-8-yl)urea,
1-(4-(trifluoromethyl)-2-(piperidin-1-yl)benzyl)-3-(3,4-dihydro-3-oxo-2H-benzo [b][1,4]oxazin-8-yl)urea,
1-(4-chlorobenzyl)-3-(3,4-dihydro-3-oxo-2H-benzo[b][1,4]oxazin-8-yl)urea,
1-(4-chloro-2-(dimethylamino)benzyl)-3-(3,4-dihydro-3-oxo-2H-benzo[b][1,4]oxazin-8-yl)urea,
1-(4-chloro-2-(pyrrolidin-1-yl)benzyl)-3-(3,4-dihydro-3-oxo-2H-benzo [b][1,4] oxazin-8-yl)urea,
1-(4-chloro-2-(piperidin-1-yl)benzyl)-3-(3,4-dihydro-3-oxo-2H-benzo [b][1,4]oxazin-8-yl)urea,
1-(4-methyl-2-(piperidin-1-yl)benzyl)-3-(3,4-dihydro-3-oxo-2H-benzo [b][1,4] oxazin-8-yl)urea,
1-(6-chloropyridin-3-yl)methyl)-3-(3,4-dihydro-3-oxo-2H-benzo [b][1,4]oxazin-8-yl)urea,
1-(3-oxo-4H-1,4-benzoxazin-8-yl)-3-[[5-(trifluoromethyl)-2-furyl]methyl]urea,
1-(3-oxo-4H-1,4-benzoxazin-8-yl)-3-[[6-(trifluoromethyl)-3-pyridyl]methyl]urea,
1-(3-oxo-4H-1,4-benzoxazin-8-yl)-3-[[2-(1-piperidyl)-6-(trifluoromethyl)-3-pyridyl]methylurea,
1-(3-oxo-4H-1,4-benzoxazin-8-yl)-3-(p-tolylmethyl)urea,
1-[[6-methyl-2-(1-piperidyl)-3-pyridyl]methyl]-3-(3-oxo-4H-1,4-benzoxazin-8-yl)urea,
1-[[2-isopropoxy-4-(trifluoromethyl)phenyl]methyl]-3-(3-oxo-4H-1,4-benzoxazin-8-yl)urea,
1-[[2-methoxy-6-(trifluoromethyl)-3-pyridyl]methyl]-3-(3-oxo-4H-1,4-benzoxazin-8-yl)urea,
1-(3-oxo-4H-1,4-benzoxazin-8-yl)-3-[[5-(trifluoromethyl)-2-pyridyl]methyl]urea,
1-[(2-isopropoxy-4-methyl-phenyl)methyl]-3-(3-oxo-4H-1,4-benzoxazin-8-yl)urea,
1-[(2-isopropoxy-6-methyl-3-pyridyl)methyl]-3-(3-oxo-4H-1,4-benzoxazin-8-yl)urea,
1-[[2-dimethylamino-6-(trifluoromethyl)-3-pyridyl]methyl]-3-(3-oxo-4H-1,4-benzoxazin-8-yl)urea,
1-(3-oxo-4H-1,4-benzoxazin-8-yl)-3-[[2-pyrrolidin-1-yl-6-(trifluoromethyl)-3-pyridyl]methyl]urea,
1-[[2-(imidazol-1-yl)-4-(trifluoromethyl)phenyl]methyl]-3-(3-oxo-4H-1,4-benzoxazin-8-yl)urea,
1-[(4-tert-butylphenyl)methyl]-3-(3-oxo-4H-1,4-benzoxazin-8-yl)urea,
1-[(4-methyl-2-pyrrolidin-1-yl-phenyl)methyl]-3-(3-oxo-4H-1,4-benzoxazin-8-yl)urea,
1-[[2-(2-dimethylaminoethoxy)-6-(trifluoromethyl)-3-pyridyl]methyl]-3-(3-oxo-4H-1,4-benzoxazin-8-yl) urea, and
1-[[2-(2-dimethylaminoethoxy)-4-(trifluoromethyl)phenyl]methyl]-3-(3-oxo-4H-1,4-benzoxazin-8-yl)urea.

2. A composition comprising the compound of claim 1; and a pharmaceutically acceptable carrier.

3. A method of treating a disease or condition ameliorated by inhibition of the vanilloid receptor TRPV1 selected from: pain associated with burns, post-operative pain, osteoarthritis, rheumatoid arthritis, headaches, dental pain, pelvic pain, migraine, mastalgia, visceral pain, neuropathy, irritable bowel syndrome, gastro-esophageal reflux disease, Crohn's disease, asthma, chronic obstructive pulmonary disease, cough, urinary incontinence, urinary bladder hypersensitiveness, psoriasis, dermatitis, myocardial ischemia, hirsutism, alopecia, rhinitis, pancreatitis, vulvodynia, dry eye, anxiety or obesity, the method comprising administering an effective amount of a compound of claim 1, to a subject in need thereof.

4. A method of treating Dry Eye comprising administering an effective amount of a compound of claim 1, to a subject in need thereof.

5. The method of claim 3, wherein said effective amount comprises from about 0.1 mg to 2000 mg/day.

6. The method of claim 3, wherein said effective amount comprises from about 5 mg to 100 mg/day.

7. A compound having the following structure:

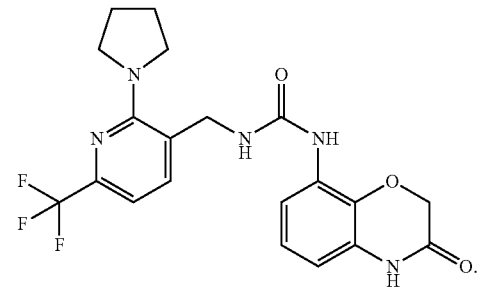 [SMILES: O=C1COc2c(cccc2NC(=O)NCc2ccc(C(F)(F)F)nc2N2CCCC2)N1]

* * * * *